United States Patent
Hsu

(10) Patent No.: US 7,223,733 B2
(45) Date of Patent: May 29, 2007

(54) MODULATION OF TRIP-BR FUNCTION AND METHOD OF TREATING PROLIFERATIVE DISORDERS

(75) Inventor: Stephen I-Hong Hsu, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 11/095,870

(22) Filed: Mar. 31, 2005

(65) Prior Publication Data

US 2005/0222034 A1 Oct. 6, 2005

Related U.S. Application Data

(60) Provisional application No. 60/557,697, filed on Mar. 31, 2004.

(51) Int. Cl.
*A61K 38/04* (2006.01)
(52) U.S. Cl. .................................. 514/13; 530/326
(58) Field of Classification Search ............ None
See application file for complete search history.

(56) References Cited

U.S. PATENT DOCUMENTS 6,372,720 B1 4/2002 Longmuir et al.
2003/0108597 A1 6/2003 Chancellor et al.

OTHER PUBLICATIONS

Sim, et al., Journal of American Society of Nephrology, 2002, 13, 33A.*
Hsu, et al., The EMBO Journal, 2001, 20, 2273-2285.*
Aasland, R., et al. The PHD finger: Implications for chromatin-mediated transcriptional regulation. Trends Biochem Sci. 1995. pp. 56-59. vol. 20.
Bandera, L.R., et al. Apoptosis induced in mammalian cells by peptides that functionally antagonize the Rb-regulated E2F transcription factor. Nature Biotech. 1997. pp. 896-901. vol. 15.
Capili, A.D., et al. Solution structure of the PHD domain from the KAP-1 corepressor: structural determinants for PHD, RING and LIM zinc-binding domains. EMBO. 2001. pp. 165-177. vol. 20.
Derossi, D., et al. The third helix of the Antennapedia Homeodomain translocates through biological membranes. J. Biol. Chem. 1994. pp. 10444-10459. vol. 269.
Diffley, J.F. and Labib, K. The chromosome replication cycle. J. Cell Sci. 2002. pp. 869-872. vol. 115.
Dyson, N. The regulation of E2F by pRB-family proteins. Genes & Development, 1998. pp. 2245-2262. vol. 12.
Elbashir, et al. Functional anatomy of siRNAs for mediating efficient RNAi in Drosophila melanogaster. EMBO J. 2001. pp. 6877-6888. vol. 20.
Frick, D.N. and Richardson, C.C. DNA primases. Annu Rev Biochem. 2001. pp. 39-80 vol. 70.
Harbour, J.W., et al. Cdk Phosphorylation Triggers Sequential Intramolecular Interactions that Progressively Block Rb Functions as Cells Move through G1. Cell. 1999. pp. 859-869. vol. 98.
Harbour, J.W. and Dean, D.C. The Rb/E2F pathway: expanding roles and emerging paradigms. Genes Dev. 2000. pp. 2393-2409. vol. 14.
Haynes, S., et al. The bromodomain: a conserved sequences found in human, Drosophila and yeast protein. Nucl Acids Res. 1992. pp. 2603. vol. 20.
Helin, K. Regulation of cell proliferation by the E2F transcription factors. Curr Opin Genet Dev. 1998. pp. 28-35. vol. 8.
Hsu, S.I.H., et al. TRIP-Br: A novel family of PHD zinc finger and bromodomain interacting proteins that regulate the transcriptional activity of E2F-1/DP-1. EMBO J. 2001. pp. 2273-2285. vol. 20.
Kalkhoven, E., et al. The PHD type zinc finger is an integral part of the CBP acetyltransferase domain. Mol Cell Biol. 2002. pp. 1961-1970. vol. 22.
Keyomarsi, K. and Herliczek, T.W. Prog Cell Cycle Res. 1997. pp. 171-191. vol. 3.
Kim, S.-S., et al. A novel member of the RING finger family, KRIP-1, associates with the KRAB-A transcriptional repressor domain of zinc finger proteins. Proc Natl Acad Sci USA. 1996. pp. 15299-15304. vol. 93.
Koepp, D.M., et al. How the cyclin became a cyclin: regulated proteolysis in the cell cycle. Cell. 1999. pp. 431-434. vol. 97.
Koepp, D.M., et al. Phosphorylation-dependent ubiquitination of cyclin E by the SCFFbw7 ubiquitin ligase. Science. 2001. pp. 177. vol. 294.
Koken, M.H.M., et al. A C4HC3 zinc finger motif. C R Acad Sci III. 1995. pp. 733-739. vol. 318.
Lam, E., et al. DP and E2F proteins: coordinating transcription with cell cycle progression. Curr Opin Cell Biol. 1994. pp. 859-866. vol. 6.
LE Douarin, B., et al. A possible involvement of TIF1a and TIF1b in the epigenetic control of transcription by nuclear receptors. EMBO J. 1996. pp. 6701-6715. vol. 15.
Lomazzi, M., et al. Suppression of the p53- or pRB-mediated G1 checkpoint is required for E2F-induced S-phase entry. Nat Gen. 2002. pp. 190-194. vol. 31.
Marmorstein, R.a.B., S.L. Structure and function of bromodomains in chromatin-regulating complexes. Gene. 2001. pp. 1-9. vol. 272.
Martin, K., et al. ,Stimulation of E2F-1/DP-1 transcriptional activity by MDM oncoprotein. Nature. 1995. pp. 691-694. vol. 375.
McGarry, T.J. and Kirschner, M.W. Geminin, an inhibitor of DNA replication, is degraded during mitosis. Cell. 1998. pp. 1043-1053. vol. 93.
Miller, G.P. and Benkovic, S.J. Stretching exercises-flexibility in dihydrofolate reductase catalysis. Chem Biol. 1998. pp. 105-113. vol. 5.
Moosmann, P. et al. Transcriptional repression by RING finger protein TIF1b that interacts with the KRAB repressor domain of KOX1. Nucl Acids Res. 1996. pp. 4859-4867. vol. 24.
Muller, H., et al. E2Fs regulate the expression of genes involved in differentiation, development, proliferation, and apoptosis. Genes Dev. 2001. pp. 267-285. vol. 15.

(Continued)

*Primary Examiner*—Anish Gupta
*Assistant Examiner*—Satyanarayana R. Gudibande
(74) *Attorney, Agent, or Firm*—Klarquist Sparkman LLP

(57) ABSTRACT

Methods for modulating TRIP-Br function and activity in a proliferating cell are provided, as well as methods for treating a proliferative disorder by modulating TRIP-Br function in a proliferating cell.

11 Claims, 23 Drawing Sheets

OTHER PUBLICATIONS

Nahle, Z., et al. Direct coupling of the cell cycle and cell death machinery by E2F. Nat Cell Biol. 2002. pp. 859-864. vol. 11.

Ohtsubo. M. and Roberts, J.M. Cyclin-dependent regulation of G1 in mammalian fibroblasts. Science. 1993. pp. 1908-1912. vol. 259.

Ohtsubo, M., et al. Human cyclin E, a nuclear protein essential for the G1-to-S phase transition. Mol Cell Biol. 1995. pp. 2612-2624. vol. 15.

Patel, T., et al. The role of proteases during apoptosis. FASEB. 1996. pp. 587-597. vol. 10.

Philips, A.C. and Vousden, K.H. E2F-1 induced apoptosis. Apoptosis. 2001. pp. 173-182. vol. 6.

Rajagopalan, H., et al. Inactivation of hCDC4 can cause chromosomal instability. Nature. 2004. pp. 77-81. vol. 428.

Rosenblatt, J., et al. Human cyclin-dependent kinase 2 is activated during the S and G2 phases of the cell cycle and associates with cyclin A. Proc. Natl Acad Sci USA. 1992. pp. 2824-2828.. vol. 89.

Roy, L.M., et al. Activation of p34cdc2 kinase by cyclin A. J Cell Biol. 1991. pp. 507-514. vol. 113.

Santiago, F.S., et al. New DNA enzyme targeting Egr-1 mRNA inhibits vascular smooth muscle proliferation and regrowth after injury. Nat Med. 1999. pp. 1264-1269. vol. 5.

Schultz, D.C., et al. Targeting histone deacetylase complexes via KRAB-zinc finger proteins: the PHD and bromodomains of KAP-1 form a cooperative unti that recruits a novel isoform of the Mi-2a subunit of NuRD. Genes Dev. 2001. pp. 428-433. vol. 15.

Sherr, C.J. Mammalian G1 Cyclings. Cell. 1993. pp. 1059-1065. vol. 73.

Sherr, C.J. and Roberts, J.M. CDK inhibitors: positive and negative regulators of G1-phase progression. Genes Dev. 1999. pp. 1501-1512. vol. 13.

Smits, V.A. and Medema, R.H. Checking out the G(2)/M transition. Biochim Biophys Acta. 2001. pp. 1-12. vol. 1519.

Spruck, C.H., et al. Deregulated cyclin E induces chromosome instability. Nature. 1999. pp. 297-300. vol. 401.

Sugimoto, M., et al. Regulation of CDK4 activity by a novel CDK-binding protein, p34SEI1. Genes Dev. 1999. pp. 3027-3033. vol. 13.

Tanaka, S. and Diffley, J.F.X. Deregulated G1-cyclin expression induces genomic instability by preventing efficient pre-RC formation. Genes Dev. 2002. pp. 2639-2649. vol. 16.

Trimarchi, J.M. and Lees, J.A. Reviews: Sibling rivalry in the E2F Family. Nat Rev Mol Cell Biol. 2002. pp. 11-20. vol. 3.

Warbrick, E. The puzzle of PCNA's many partners. Bioessays. 2000. pp. 997-1006. vol. 22.

Wohlschlegel, J.A., et al. Inhibition of eukaryotic DNA replication by geminin binding to Cdt1. Science. 2000. pp. 2309-2312. vol. 290.

Zeng, L. and Zhou, M.-M. Bromodomain: an Acetyl-lysine binding domain. FEBS Letters. 2002. pp. 124-128. vol. 513(1).

Sim, K.G., et al. TRIP-Br Links E2F to Novel Functions in the Regulation of Cyclin E Expression during Cell Cycle Progression and in the Maintenance of Genomic Stability. Cell Cycle. Oct. 2004. pp. 1296-1304. vol. 3, Issue 10. Epub Oct. 6, 2004.

* cited by examiner

A
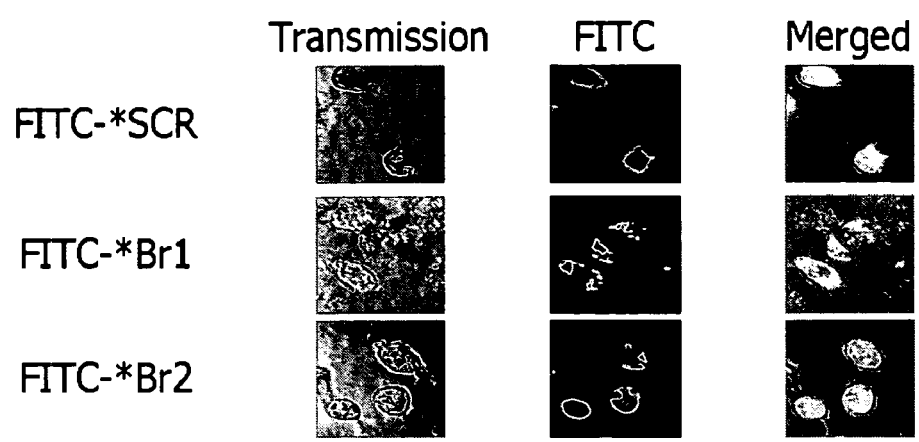
B
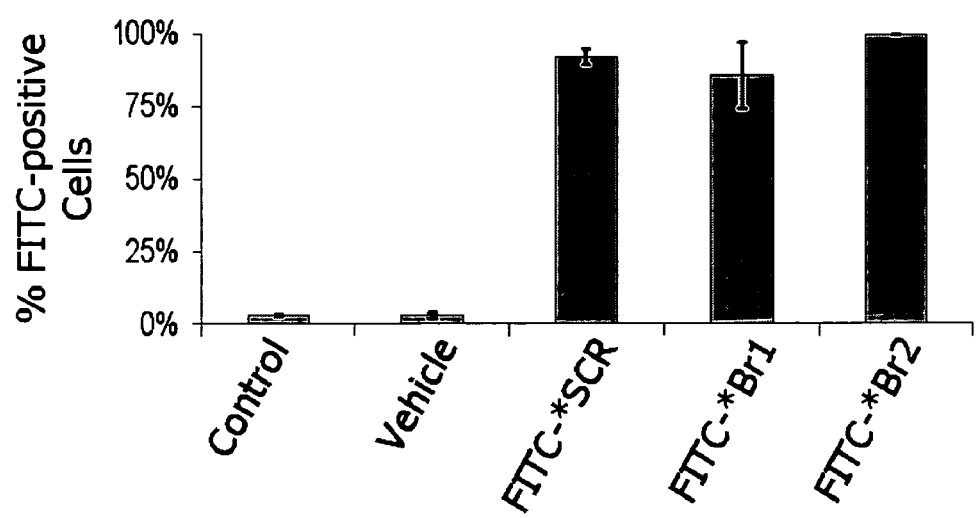
FIGURE 2

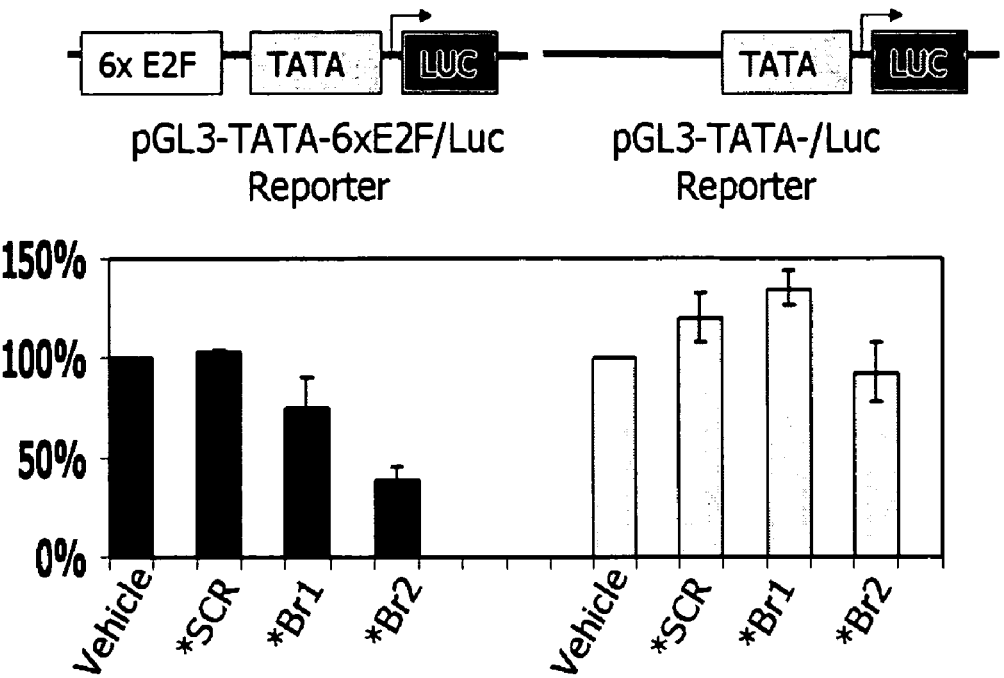
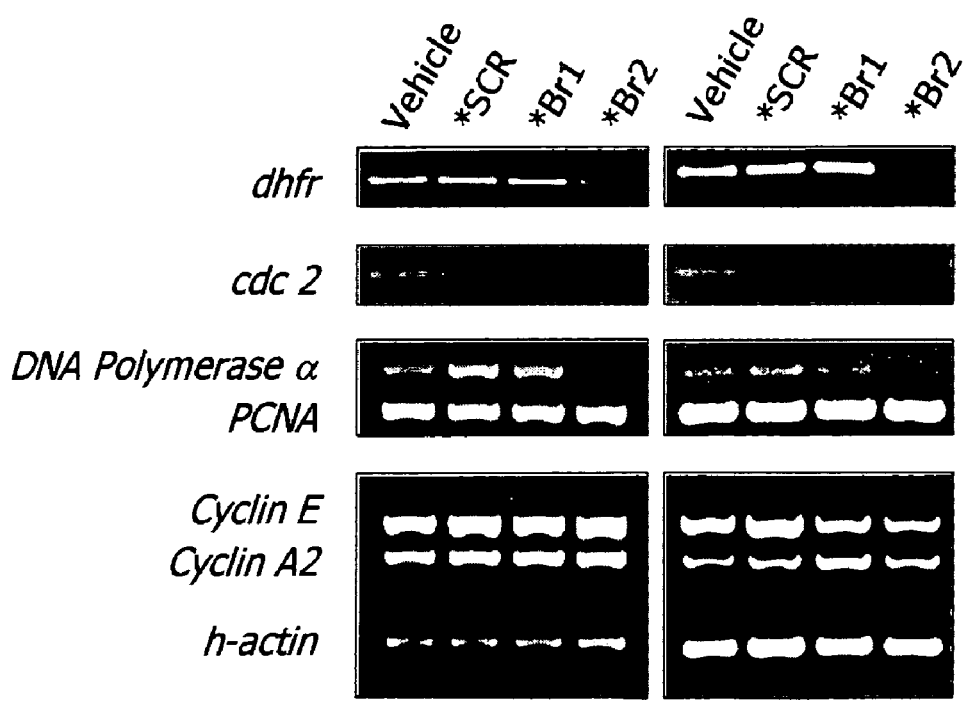
FIGURE 3

A
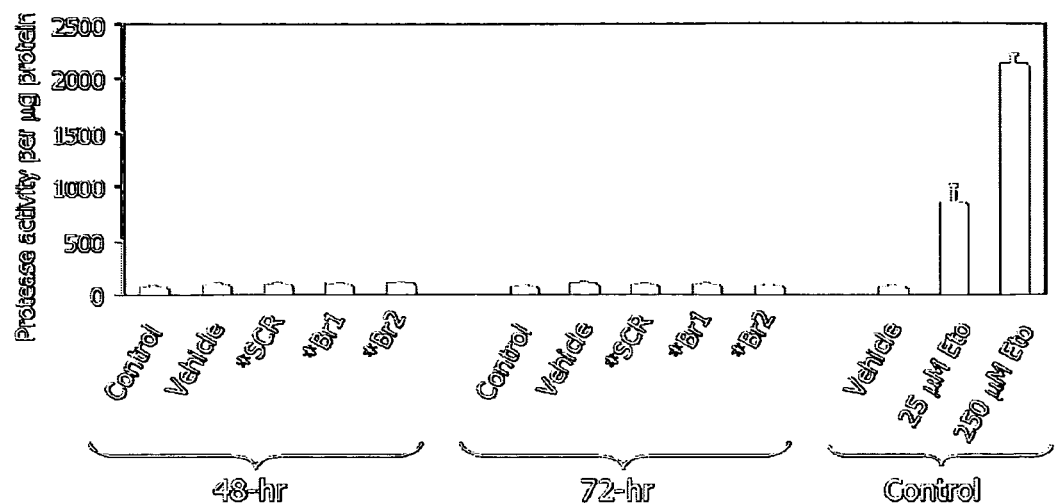
B
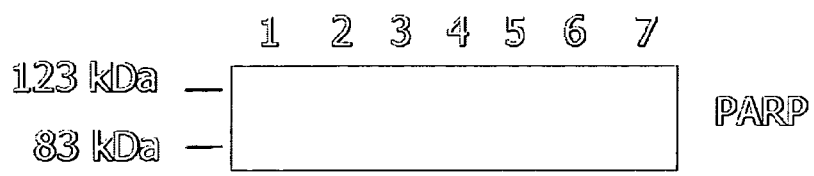
FIGURE 6

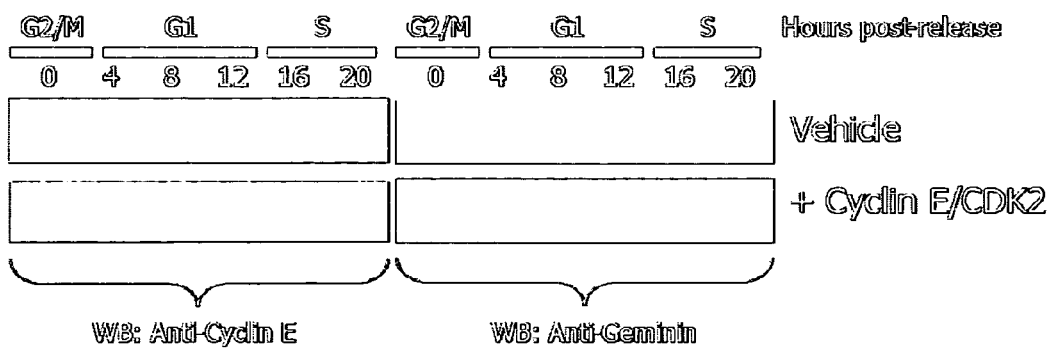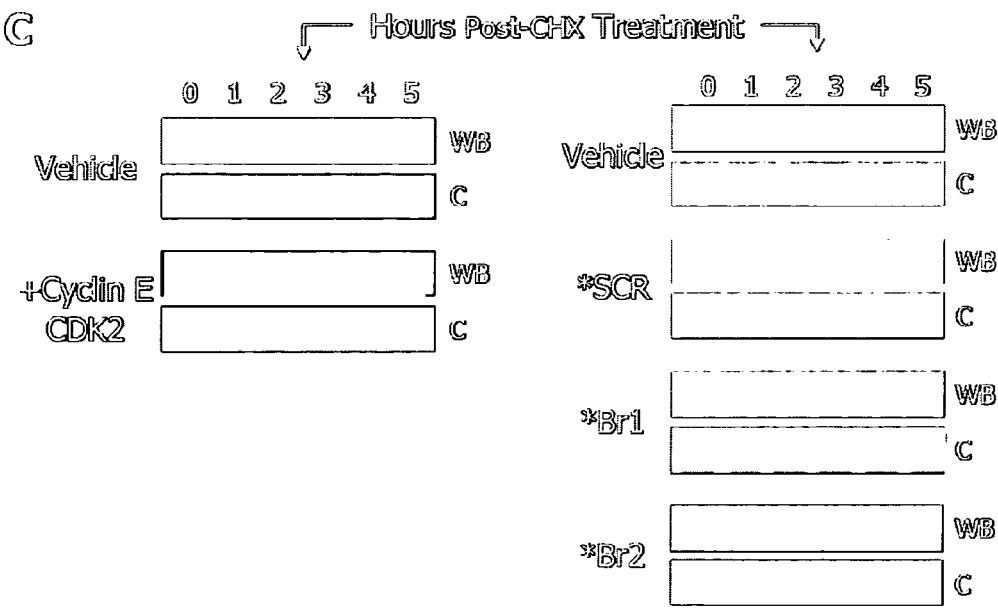
FIGURE 7

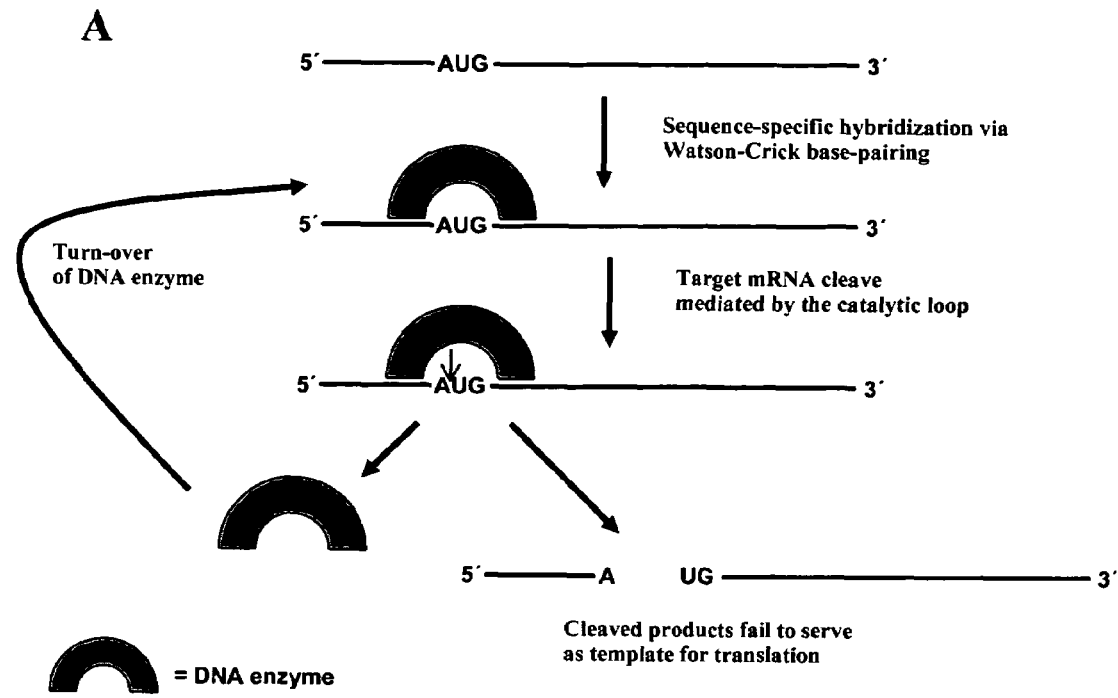
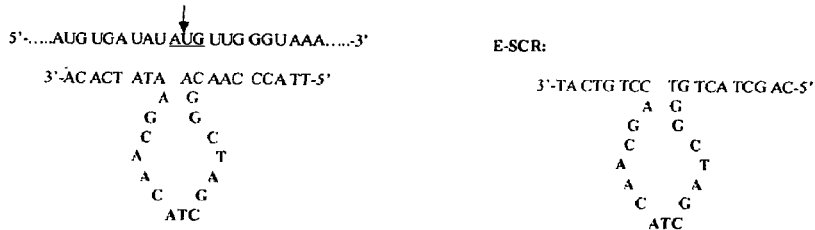
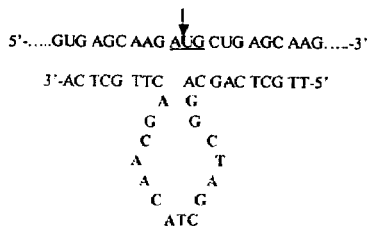
FIGURE 10

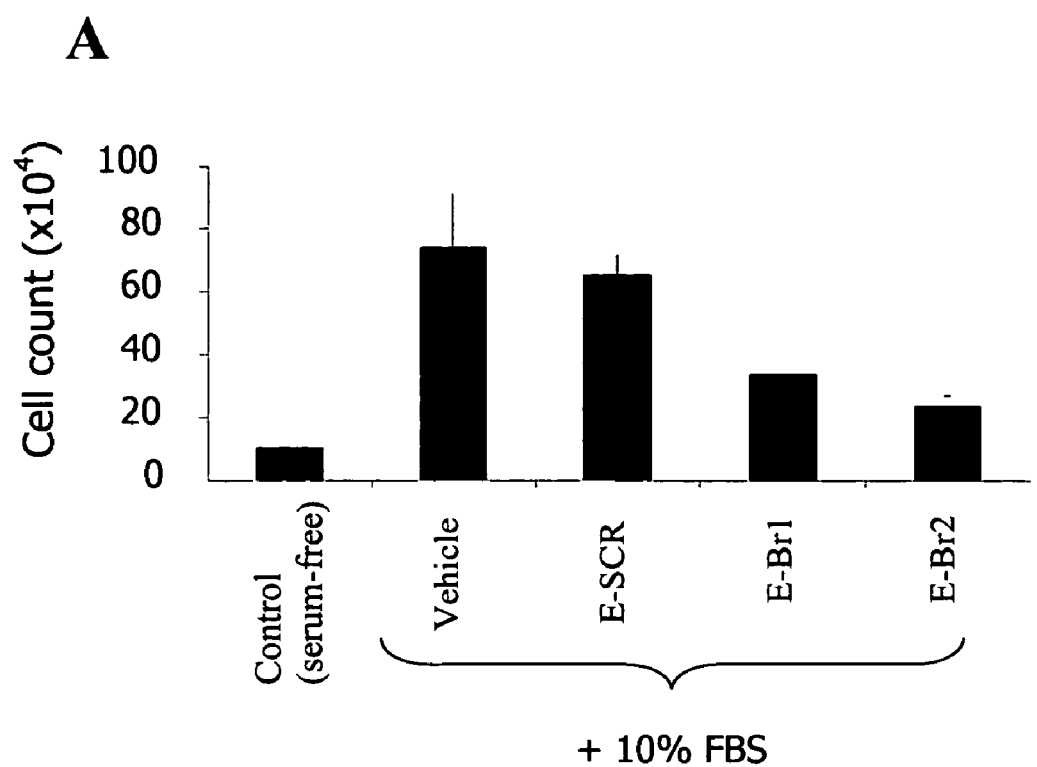
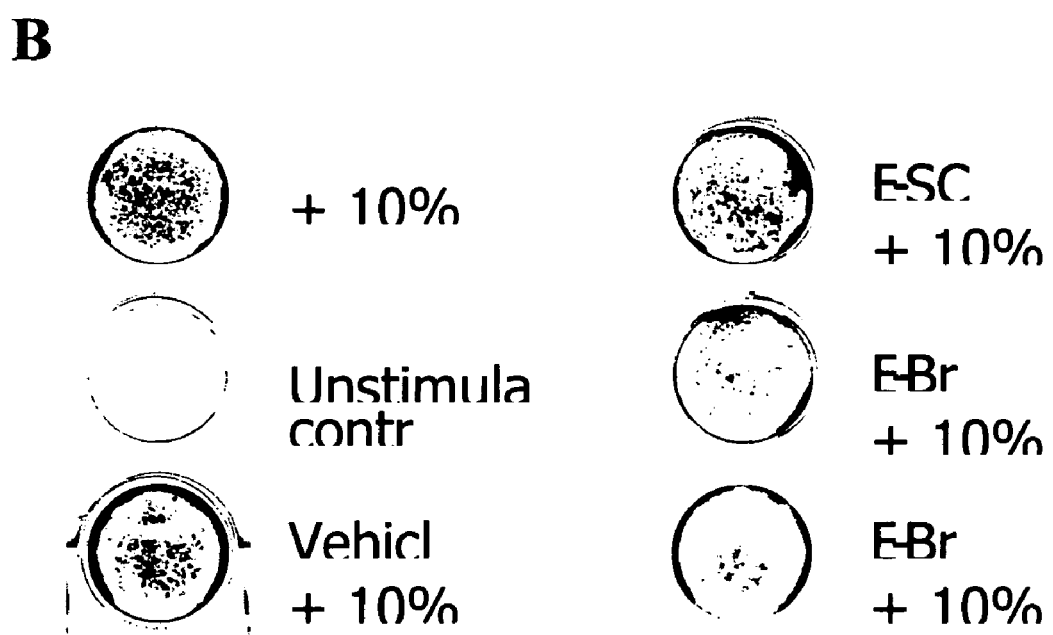
FIGURE 12

A
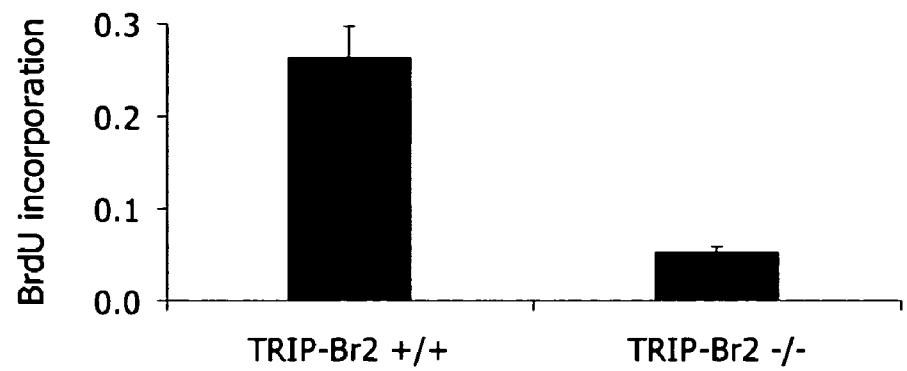
B
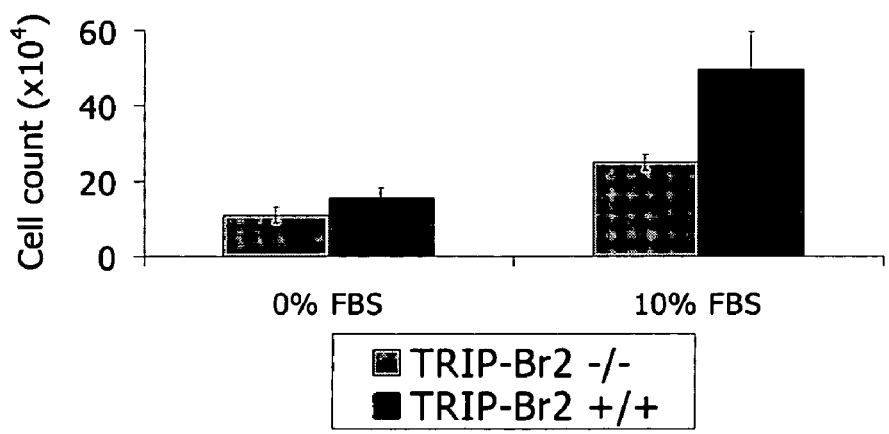
C
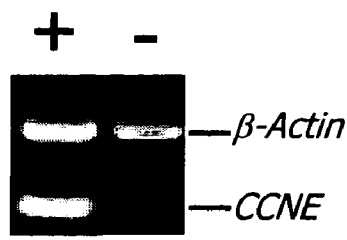
FIGURE 15

```
hTRIP-Br2   MLGKGGKRKFDEHEDGLEGKIVSPCDGPSKVSYTLQRQTIFNISLMKLYNHRPLTEPSLQ  60
mTRIP-Br2   ------------------------------------------------------------
hTRIP-Br1   ------------------------------------------------------------
mTRIP-Br1   ------------------------------------------------------------ hTRIP-Br2   KTVLINNMLRRIQEELKQEGSLRPMFTPSSQPTTEPSDSYREAPPAFSHLASPSSHPCDL  120
mTRIP-Br2   ------------------------------------------------------------
hTRIP-Br1   ---------------MLSKGLKRKREEEEKEPLAVDSWLDPGHAAVAQAPPAVASSSL   45
mTRIP-Br1   ---------------MLSKGLKRKREEETMEALSVDSCWLDPSHPAVAQTPPTVASSSL  45 hTRIP-Br2   GSTTPLEACLTPASLLEDDDDTFCTSQAMQPTAPTKLSPPALLPEKDSFSSALDEIEELC  180
mTRIP-Br2   --------------LEDDNDDTFFTFQAVHSAAPTRLSSAALPAEKDSFSSALDEIEELC  46
hTRIP-Br1   FDLSVLKLHHSLQQSEPDLRHLVLVVNTLRRIQASMAPAAALPPVPSPPAAPSVADNLLA  105
mTRIP-Br1   FDLSVVKLHHSLRQSEPDLRHLVLVVNTLRRIQASMEPAPVLPPEPIQPPAPSVADSLLA  105
                          *  ::::: .  ::.   . *    .  :*. . .* .

hTRIP-Br2   PTSTSTEAA-TAATDSVKGTSSEAGTQKLDGPQESRADDSKLMDSLPGNFEIT-TSTGFL  238
mTRIP-Br2   PTSTSTEAAHTAAPEGPKGTSSESSVQKPEGPEEGRTDDSRFMDSLPGNFEIT-TSTGFL  105
hTRIP-Br1   SSDAALSASMASLLEDLSHIEGLSQAPQPLADEGPPGRSIGGAAPSLGALDLLGPATGCL  165
mTRIP-Br1   SSDAGLSASMASLLEDLNHIEDLNQAPQPQADEGPPGRSIGGISPNLGALDLLGPATGCL  165
             *  :  **.::::  ..  .   *      *  *    .:*** ::.*.

hTRIP-Br2   TDLTLDDILFADIDTSMYDFDPCTSSSGTASKMAPVSADDLLKTLAPYSSQPVTPSQPFK  298
mTRIP-Br2   TDLTLDDILFADIDTSMYDFDPCTSASGTASKMAPVSADDLLKTLAPYSNQPVAPSQPFK  165
hTRIP-Br1   LDDGLEG-LFEDIDTSMYDNELWAPAS---------------EGLKPGPEDGPGKEEAPE  209
mTRIP-Br1   LDDGLEG-LFEDIDTSMYDSELWLPAS---------------EGLKPGPENGPAKEEPPE  209
             *   *  ** ********  *  .:                ::.  ::  :: ::

hTRIP-Br2   MDLTELDHIMEVLVGS---------------  314
mTRIP-Br2   MDLTELDHIMEVLVGS---------------  181
hTRIP-Br1   LDEAELDYLMDVLVGTQALERPPGPGR     236
mTRIP-Br1   LDEAELDYLMDVLVGTQALERPPGPGR     236
            :* :*****::::***:
```

FIGURE 20

SEQUENCE LISTING

<160> NUMBER OF SEQ ID NOS: 16

<210> SEQ ID NO 1
<211> LENGTH: 18
<212> TYPE: PRT
<213> ORGANISM: Homo sapiens

<400> SEQUENCE: 1

Ala Thr Gly Cys Leu Leu Asp Asp Gly Leu Glu Gly Leu Phe Glu Asp
1               5                   10                  15

Ile Asp

<210> SEQ ID NO 2
<211> LENGTH: 18
<212> TYPE: PRT
<213> ORGANISM: Homo sapiens
<220> FEATURE:
<221> NAME/KEY: misc_feature
<223> OTHER INFORMATION: PHD/bromodomain interacting region from human
      TRIP-Br2

<400> SEQUENCE: 2

Thr Gly Phe Leu Thr Asp Leu Thr Leu Asp Asp Ile Leu Phe Ala Asp
1               5                   10                  15

Ile Asp

<210> SEQ ID NO 3
<211> LENGTH: 17
<212> TYPE: PRT
<213> ORGANISM: Drosophila melanogaster
<220> FEATURE:
<221> NAME/KEY: misc_feature
<223> OTHER INFORMATION: Penetratin sequence from antennia homeo domain
      protein from Drosophila melanogaster

<400> SEQUENCE: 3

Glu Arg Gln Ile Lys Ile Trp Phe Gln Asn Arg Arg Met Lys Trp Lys
1               5                   10                  15

Lys

<210> SEQ ID NO 4
<211> LENGTH: 35
<212> TYPE: PRT
<213> ORGANISM: Artificial Sequence
<220> FEATURE:
<223> OTHER INFORMATION: Peptide containing penetratin sequence from
      Drosophila and PHD/bromodomain interacting region from human
      TRIP-Br1

<400> SEQUENCE: 4

Glu Arg Gln Ile Lys Ile Trp Phe Gln Asn Arg Arg Met Lys Trp Lys
1               5                   10                  15

Lys Ala Thr Gly Cys Leu Leu Asp Asp Gly Leu Glu Gly Leu Phe Glu
            20                  25                  30

Asp Ile Asp
        35

<210> SEQ ID NO 5
<211> LENGTH: 35
<212> TYPE: PRT
<213> ORGANISM: Artificial Sequence
<220> FEATURE:
<223> OTHER INFORMATION: Peptide containing penetratin sequence from
      Drosophila and PHD/bromodomain interacting region from human
      TRIP-Br2

<400> SEQUENCE: 5

Glu Arg Gln Ile Lys Ile Trp Phe Gln Asn Arg Arg Met Lys Trp Lys
1               5                   10                  15

Lys Thr Gly Phe Leu Thr Asp Leu Thr Leu Asp Ile Leu Phe Ala
            20                  25                  30

Asp Ile Asp
        35

<210> SEQ ID NO 6
<211> LENGTH: 33
<212> TYPE: DNA
<213> ORGANISM: Artificial Sequence
<220> FEATURE:
<223> OTHER INFORMATION: DNA enzyme directed against human TRIP-Br1
      transcript

<400> SEQUENCE: 6
ttacccaaca ggctagctac aacgaatatc aca                               33

<210> SEQ ID NO 7
<211> LENGTH: 33
<212> TYPE: DNA

```
<213> ORGANISM: Artificial Sequence
<220> FEATURE:
<223> OTHER INFORMATION: DNA enzyme directed against human TRIP-Br2
      transcript

<400> SEQUENCE: 7
ttgctcagca ggctagctac aacgacttgc tca                                      33

<210> SEQ ID NO 8
<211> LENGTH: 35
<212> TYPE: PRT
<213> ORGANISM: Artificial Sequence
<220> FEATURE:
<223> OTHER INFORMATION: Peptide containing penetratin sequence from
      Drosophila and random peptide sequence

<400> SEQUENCE: 8

Glu Arg Gln Ile Lys Ile Trp Phe Gln Asn Arg Arg Met Lys Trp Lys
1               5                   10                  15

Lys Gly Leu Asp Glu Asp Gly Leu Leu Leu Phe Cys Glu Gly Asp Thr
            20                  25                  30

Ile Ala Asp
        35

<210> SEQ ID NO 9
<211> LENGTH: 33
<212> TYPE: DNA
<213> ORGANISM: Artificial Sequence
<220> FEATURE:
<223> OTHER INFORMATION: DNA enzyme directed against random transcript
      sequence

<400> SEQUENCE: 9
cagctactgt ggctagctac aacgacctgt cat                                      33

<210> SEQ ID NO 10
<211> LENGTH: 17
<212> TYPE: PRT
<213> ORGANISM: Homo sapiens
<220> FEATURE:
<221> NAME/KEY: misc_feature
<223> OTHER INFORMATION: Immunogenic peptide from human TRIP-Br1

<400> SEQUENCE: 10

Asp Pro Gly His Thr Ala Ala Val Ala Gln Ala Pro Pro Ala Val Ala
1               5                   10                  15

Ser

<210> SEQ ID NO 11
<211> LENGTH: 15
<212> TYPE: PRT
<213> ORGANISM: Homo sapiens
<220> FEATURE:
<221> NAME/KEY: misc_feature
<223> OTHER INFORMATION: Immunogenic peptide from human TRIP-Br2

<400> SEQUENCE: 11

Ser Val Ala Asp Asn Leu Leu Ala Ser Ser Asp Ala Ala Leu Ser
1               5                   10                  15

<210> SEQ ID NO 12
<211> LENGTH: 314
<212> TYPE: PRT
<213> ORGANISM: Homo sapiens
<220> FEATURE:
<221> NAME/KEY: misc_feature
```

<223> OTHER INFORMATION: TRIP-Br2

<400> SEQUENCE: 12

```
Met Leu Gly Lys Gly Gly Lys Arg Lys Phe Asp Glu His Glu Asp Gly
1               5                   10                  15

Leu Glu Gly Lys Ile Val Ser Pro Cys Asp Gly Pro Ser Lys Val Ser
            20                  25                  30

Tyr Thr Leu Gln Arg Gln Thr Ile Phe Asn Ile Ser Leu Met Lys Leu
        35                  40                  45

Tyr Asn His Arg Pro Leu Thr Glu Pro Ser Leu Gln Lys Thr Val Leu
    50                  55                  60

Ile Asn Asn Met Leu Arg Arg Ile Gln Glu Glu Leu Lys Gln Glu Gly
65                  70                  75                  80

Ser Leu Arg Pro Met Phe Thr Pro Ser Ser Gln Pro Thr Thr Glu Pro
                85                  90                  95

Ser Asp Ser Tyr Arg Glu Ala Pro Pro Ala Phe Ser His Leu Ala Ser
            100                 105                 110

Pro Ser Ser His Pro Cys Asp Leu Gly Ser Thr Thr Pro Leu Glu Ala
        115                 120                 125

Cys Leu Thr Pro Ala Ser Leu Leu Glu Asp Asp Asp Thr Phe Cys
130                 135                 140

Thr Ser Gln Ala Met Gln Pro Thr Ala Pro Thr Lys Leu Ser Pro Pro
145                 150                 155                 160

Ala Leu Leu Pro Glu Lys Asp Ser Phe Ser Ala Leu Asp Glu Ile
            165                 170                 175

Glu Glu Leu Cys Pro Thr Ser Thr Ser Thr Glu Ala Ala Thr Ala Ala
        180                 185                 190

Thr Asp Ser Val Lys Gly Thr Ser Ser Glu Ala Gly Thr Gln Lys Leu
    195                 200                 205

Asp Gly Pro Gln Glu Ser Arg Ala Asp Asp Ser Lys Leu Met Asp Ser
210                 215                 220

Leu Pro Gly Asn Phe Glu Ile Thr Thr Ser Thr Gly Phe Leu Thr Asp
225                 230                 235                 240

Leu Thr Leu Asp Asp Ile Leu Phe Ala Asp Ile Asp Thr Ser Met Tyr
            245                 250                 255

Asp Phe Asp Pro Cys Thr Ser Ser Ser Gly Thr Ala Ser Lys Met Ala
        260                 265                 270

Pro Val Ser Ala Asp Asp Leu Leu Lys Thr Leu Ala Pro Tyr Ser Ser
    275                 280                 285

Gln Pro Val Thr Pro Ser Gln Pro Phe Lys Met Asp Leu Thr Glu Leu
    290                 295                 300

Asp His Ile Met Glu Val Leu Val Gly Ser
305                 310
```

<210> SEQ ID NO 13
<211> LENGTH: 181
<212> TYPE: PRT
<213> ORGANISM: Mus musculus
<220> FEATURE:
<221> NAME/KEY: misc_feature
<223> OTHER INFORMATION: TRIP-Br2

<400> SEQUENCE: 13

```
Leu Glu Asp Asp Asn Asp Asp Thr Phe Thr Phe Gln Ala Val His
1               5                   10                  15

Ser Ala Ala Pro Thr Arg Leu Ser Ser Ala Ala Leu Pro Ala Glu Lys
```

-continued

```
                 20                  25                  30
Asp Ser Phe Ser Ser Ala Leu Asp Glu Ile Glu Glu Leu Cys Pro Thr
            35                  40                  45
Ser Thr Ser Thr Glu Ala Ala His Thr Ala Ala Pro Glu Gly Pro Lys
        50                  55                  60
Gly Thr Ser Ser Glu Ser Ser Val Gln Lys Pro Glu Gly Pro Glu Glu
65                  70                  75                  80
Gly Arg Thr Asp Asp Ser Arg Phe Met Asp Ser Leu Pro Gly Asn Phe
                85                  90                  95
Glu Ile Thr Thr Ser Thr Gly Phe Leu Thr Asp Leu Thr Leu Asp Asp
            100                 105                 110
Ile Leu Phe Ala Asp Ile Asp Thr Ser Met Tyr Asp Phe Asp Pro Cys
            115                 120                 125
Thr Ser Ala Ser Gly Thr Ala Ser Lys Met Ala Pro Val Ser Ala Asp
            130                 135                 140
Asp Leu Leu Lys Thr Leu Ala Pro Tyr Ser Asn Gln Pro Val Ala Pro
145                 150                 155                 160
Ser Gln Pro Phe Lys Met Asp Leu Thr Glu Leu Asp His Ile Met Glu
                165                 170                 175
Val Leu Val Gly Ser
            180

<210> SEQ ID NO 14
<211> LENGTH: 236
<212> TYPE: PRT
<213> ORGANISM: Homo sapiens
<220> FEATURE:
<221> NAME/KEY: misc_feature
<223> OTHER INFORMATION: TRIP-Br1

<400> SEQUENCE: 14

Met Leu Ser Lys Gly Leu Lys Arg Lys Glu Glu Glu Glu Glu Glu Lys
1               5                   10                  15
Glu Pro Leu Ala Val Asp Ser Trp Trp Leu Asp Pro Gly His Ala Ala
            20                  25                  30
Val Ala Gln Ala Pro Pro Ala Val Ala Ser Ser Ser Leu Phe Asp Leu
        35                  40                  45
Ser Val Leu Lys Leu His His Ser Leu Gln Gln Ser Glu Pro Asp Leu
    50                  55                  60
Arg His Leu Val Leu Val Val Asn Thr Leu Arg Arg Ile Gln Ala Ser
65                  70                  75                  80
Met Ala Pro Ala Ala Ala Leu Pro Pro Val Pro Ser Pro Pro Ala Ala
                85                  90                  95
Pro Ser Val Ala Asp Asn Leu Leu Ala Ser Ser Asp Ala Ala Leu Ser
            100                 105                 110
Ala Ser Met Ala Ser Leu Leu Glu Asp Leu Ser His Ile Glu Gly Leu
            115                 120                 125
Ser Gln Ala Pro Gln Pro Leu Ala Asp Glu Gly Pro Pro Gly Arg Ser
        130                 135                 140
Ile Gly Gly Ala Ala Pro Ser Leu Gly Ala Leu Asp Leu Leu Gly Pro
145                 150                 155                 160
Ala Thr Gly Cys Leu Leu Asp Asp Gly Leu Glu Gly Leu Phe Glu Asp
                165                 170                 175
Ile Asp Thr Ser Met Tyr Asp Asn Glu Leu Trp Ala Pro Ala Ser Glu
            180                 185                 190
```

```
Gly Leu Lys Pro Gly Pro Glu Asp Gly Pro Gly Lys Glu Glu Ala Pro
            195                 200                 205

Glu Leu Asp Glu Ala Glu Leu Asp Tyr Leu Met Asp Val Leu Val Gly
        210                 215                 220

Thr Gln Ala Leu Glu Arg Pro Pro Gly Pro Gly Arg
225                 230                 235

<210> SEQ ID NO 15
<211> LENGTH: 236
<212> TYPE: PRT
<213> ORGANISM: Mus musculus
<220> FEATURE:
<221> NAME/KEY: misc_feature
<223> OTHER INFORMATION: TRIP-Br1

<400> SEQUENCE: 15

Met Leu Ser Lys Gly Leu Lys Arg Lys Arg Glu Glu Glu Glu Thr Met
1               5                   10                  15

Glu Ala Leu Ser Val Asp Ser Cys Trp Leu Asp Pro Ser His Pro Ala
            20                  25                  30

Val Ala Gln Thr Pro Pro Thr Val Ala Ser Ser Ser Leu Phe Asp Leu
        35                  40                  45

Ser Val Val Lys Leu His His Ser Leu Arg Gln Ser Glu Pro Asp Leu
    50                  55                  60

Arg His Leu Val Leu Val Asn Thr Leu Arg Arg Ile Gln Ala Ser
65                  70                  75                  80

Met Glu Pro Ala Pro Val Leu Pro Pro Glu Pro Ile Gln Pro Pro Ala
            85                  90                  95

Pro Ser Val Ala Asp Ser Leu Leu Ala Ser Ser Asp Ala Gly Leu Ser
        100                 105                 110

Ala Ser Met Ala Ser Leu Leu Glu Asp Leu Asn His Ile Glu Asp Leu
    115                 120                 125

Asn Gln Ala Pro Gln Pro Gln Ala Asp Glu Gly Pro Pro Gly Arg Ser
130                 135                 140

Ile Gly Gly Ile Ser Pro Asn Leu Gly Ala Leu Asp Leu Leu Gly Pro
145                 150                 155                 160

Ala Thr Gly Cys Leu Leu Asp Asp Gly Leu Glu Gly Leu Phe Glu Asp
            165                 170                 175

Ile Asp Thr Ser Met Tyr Asp Ser Glu Leu Trp Leu Pro Ala Ser Glu
        180                 185                 190

Gly Leu Lys Pro Gly Pro Glu Asn Gly Pro Ala Lys Glu Glu Pro Pro
    195                 200                 205

Glu Leu Asp Glu Ala Glu Leu Asp Tyr Leu Met Asp Val Leu Val Gly
        210                 215                 220

Thr Gln Ala Leu Glu Arg Pro Pro Gly Pro Gly Arg
225                 230                 235

<210> SEQ ID NO 16
<211> LENGTH: 19
<212> TYPE: PRT
<213> ORGANISM: Artificial Sequence
<220> FEATURE:
<223> OTHER INFORMATION: Consensus sequence for the PHD-bromodomain
      binding region of TRIP-Br
<220> FEATURE:
<221> NAME/KEY: misc_feature
<222> LOCATION: (1)..(1)
<223> OTHER INFORMATION: Xaa can be Ser, Thr, Ala, or no amino acid
<220> FEATURE:
<221> NAME/KEY: misc_feature
```

```
<222> LOCATION: (4)..(4)
<223> OTHER INFORMATION: Xaa can be any amino acid
<220> FEATURE:
<221> NAME/KEY: misc_feature
<222> LOCATION: (6)..(6)
<223> OTHER INFORMATION: Xaa can be any amino acid
<220> FEATURE:
<221> NAME/KEY: misc_feature
<222> LOCATION: (8)..(9)
<223> OTHER INFORMATION: Xaa can be any amino acid
<220> FEATURE:
<221> NAME/KEY: misc_feature
<222> LOCATION: (11)..(11)
<223> OTHER INFORMATION: Xaa can be Asp or Glu
<220> FEATURE:
<221> NAME/KEY: misc_feature
<222> LOCATION: (12)..(12)
<223> OTHER INFORMATION: Xaa can be Asp, Glu, Ala, or Gly
<220> FEATURE:
<221> NAME/KEY: misc_feature
<222> LOCATION: (13)..(13)
<223> OTHER INFORMATION: Xaa can be Ile, Leu, Val, Ala, or no amino acid
<220> FEATURE:
<221> NAME/KEY: misc_feature
<222> LOCATION: (16)..(16)
<223> OTHER INFORMATION: Xaa can be Asp, Glu, Ala, or Gly

<400> SEQUENCE: 16

Xaa Thr Gly Xaa Leu Xaa Asp Xaa Xaa Leu Xaa Xaa Xaa Leu Phe Xaa
1               5                   10                  15

Asp Ile Asp
```

MODULATION OF TRIP-BR FUNCTION AND METHOD OF TREATING PROLIFERATIVE DISORDERS

CROSS-REFERENCE TO RELATED APPLICATION

The present application claims benefit and priority from U.S. provisional patent application No. 60/557,697, filed on Mar. 31, 2004, which is hereby fully incorporated herein by reference.

FIELD OF THE INVENTION

The present invention relates generally to methods of treating diseases involving proliferative disorders, including methods of treating cancer.

BACKGROUND OF THE INVENTION

Normally, cells have mechanisms to control growth and proliferation, such that a cell will only divide and grow under certain circumstances, and in a controlled manner. Cells also have mechanisms that induce cell death, or apoptosis, when the normal regulatory mechanisms that govern cell growth and proliferation are subverted. However, in some instances, such proliferation control and apoptotic mechanisms breakdown, allowing the cell to proliferate unchecked, potentially leading to a proliferative disorder or disease within an organism. Such proliferative disorders include cancer and other hypercellular lesions such as psoriasis, warts and keloids.

Uncontrolled cellular proliferation may result from dysregulation of gene expression. Cells have a tightly controlled cycle of DNA replication and division (the cell cycle), which is regulated by a series of cell cycle and transcription factors. One set of cell cycle transcription factors, the E2F transcription factors, have been shown to play a crucial role in regulating cellular proliferation by integrating the activity of the cell cycle machinery with that of the transcriptional apparatus in a manner that contributes to the timely expression of genes required for cell cycle progression and proliferation (Lam, E., et al., *Curr Opin Cell Biol* 6, 859-866 (1994); Dyson, N. (1998), *Genes Dev* 12: 2245-2262; Helin, K, (1998), *Curr Opin Genet Dev* 8: 28-35; Harbour, J. W., and Dean, D. C. (2000), *Genes Dev* 14: 2393-2409; Trimarchi, J. M. and Lees, J. A. (2002), *Nat Rev Mol Cell Bio* 3: 11-20). The E2F transcription factors, in particular E2F-1, have been implicated in the regulation of apoptosis (Muller, H., et al., *Genes Dev* 15, 267-285 (2001); Nahle, Z., et al., *Nat Cell Biol*, (2002) 11:859-64; Philips, A. C., and Vousden, K. H. *Apoptosis* 6, 173-182 (2001)).

Cyclin E-associated kinase activity has been shown to be essential for traversing the restriction point and executing S phase entry during cell cycle progression (Keyomarsi, K., and Herliczek, T. W. (1997), *Prog Cell Cycle Res* 3: 171-191). The entry into, passage through and exit from the cell cycle are precisely controlled by the sequential activation of the cyclin-dependent kinases (Cdks) Cdk4/6, Cdk2 and Cdc2 (Sherr, C. J., and Roberts, J. M. (1999), *Genes Dev* 13: 1501-1512). Commitment of cells to enter the cell cycle is regulated by growth factors (both positive and negative) that exert their effect during the G1 phase.

The G1 D-type cyclins, in conjunction with cyclin-dependent kinases Cdk4 and Cdk6, play key roles in the execution of mitogen-induced cellular proliferation. Positive (mitogenic) growth factors convey growth-stimulatory signals that promote the synthesis of the D-type cyclins and their assembly into active Cdk4/6-cyclin D complexes, resulting in their catalytic activation and substrate recognition. Active Cdk4/6-cyclin D complexes contribute to cyclin-E/Cdk2 activation and generation of hypo-phosphorylated RB. The hypo-phosphorylated RB bound to transcriptionally inactive E2F-1/DP-1 complexes serves as a target for hyper-phosphorylation by activated cyclin-E/Cdk2, resulting in the dissociation of RB, derepression/activation of E2F-responsive genes and release of cells from the late G1 checkpoint (Sherr, C. J. (1993), *Cell* 73: 1059-1065; Lam et al., supra; Dyson, supra; Helin, supra; Harbour, J. W., et al., (1999), *Cell* 98: 859-869; Sherr, (1999), supra; Harbour (2000), supra; Trimarchi et al., supra).

As key regulators of mitogenic-signaling pathways, Cdk4/Cdk6-cyclin D activities are regulated at multiple levels, including the synthesis and binding of cyclin D, both inhibitory and activating phosphorylation events, and the association/dissociation of inhibitory molecules called Cdk inhibitors (CKIs) (Sherr (1999), supra). Cdk proteins are inactive unless they are bound to the respective cyclin partners. Upon binding, each cyclin-Cdk complex is further subjected to negative and positive regulation through specific phosphorylations. Further negative regulation is provided by the binding of specific Cdk inhibitors (CKI) that disrupt the active site and interfere with ATP binding. Mammalian CKIs are classified into two families, the Cip/Kip (Cdk2/kinase inhibitor protein) and the Ink4 (inhibitors of cyclin-dependent kinase 4) inhibitors, both of which restrain cell cycle progression by specifically and coordinately binding to Cdk complexes controlling $G_1$ and $G_1/S$ phases. While the Cip/Kip family CKIs are less specific, inhibiting Cdk2, Cdk4 and Cdk6 activities, the Ink4 inhibitors (p16/Ink4a, p15/Ink4b, p18/Ink4c and p19/Ink4d) bind specifically to cyclin D-Cdk4 and -Cdk6 complexes.

An additional level of regulation imposed on Cdk4 has recently been identified. $p34^{SEI-1}$, a novel cyclin-dependent kinase 4 (Cdk4)-binding protein that appears to antagonize the function of $p16^{INK4a}$, has been shown to render the cyclin D1-Cdk4 complex resistant to inhibition by $p16^{INK4a}$ (Sugimoto, M., et al., (1999), *Genes Dev* 13: 3027-3033). $p34^{SEI-1}$ is a serum inducible protein whose ectopic expression enables fibroblasts to proliferate even in low serum concentrations. $p34^{SEI-1}$ has been proposed to play key functional role(s) in facilitating the formation and activation of cyclin D-Cdk complexes and mediating mitogen-driven cell cycle progression (Sugimoto et al., supra).

In order to address proliferative disorders that result when the regulation of the above-described pathway of cell cycle progression is rendered abnormal, it is important to find ways of blocking cell cycle progression in abnormally proliferating cells. Thus, there exists a need for novel treatments and methods of inducing proliferative block in cells.

SUMMARY OF THE INVENTION

In one aspect, there is provided a method of inhibiting proliferation of a cell, comprising modulating activity of TRIP-Br.

In another aspect, there is provided a method of treating a proliferative disorder in a patient, comprising administering to the patient a molecule capable of modulating activity of TRIP-Br in a proliferating cell of the patient, wherein the proliferating cell is associated with the proliferative disorder.

In a further aspect, there is provided a molecule capable of modulating activity of TRIP-Br.

In yet a further aspect, there is provided a pharmaceutical composition comprising a molecule capable of modulating activity of TRIP-Br and a pharmaceutically acceptable diluent.

In still a further aspect, there is provided a monoclonal antibody directed against TRIP-Br.

In a further aspect, there is provided a method of identifying a modulator of TRIP-Br comprising contacting a protein target of TRIP-Br with a peptide comprising a plant homeo domain zinc finger/bromodomain binding region of TRIP-Br in the presence of a test compound, and determining the effect of the test compound on the binding of the protein target of TRIP-Br with the peptide comprising a plant homeo domain zinc finger/bromodomain binding region of TRIP-Br.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

FIG. 2 is A: fluorescence micrograph of U2OS cells treated with FITC-labeled *SCR, *Br1 and *Br2; B: measurement of peptide internalization efficiency by flow cytometry;

FIG. 3 is A: a graph of the results of a β-galactosidase/luciferase assay of U2OS cells co-transfected with pCMV/β-galactosidase and the indicated luciferase reporter plasmids; B: agarose gel of RT-PCR analysis on total RNA for dhfr, cyclin-E, cyclin A2, PCNA, DNA Polα and cdc2 expression in U2OS cells exposed to decoy peptides;

FIG. 6 is A: results of a caspase 3 protease activity assay in U2OS cells exposed to either Eto (Etoposide) for 24 h or decoy peptides for 48 or 72 h; B: western blot analysis of PARP cleavage;

FIG. 7 is A: Protein expression profile of U2OS cells released from nocodazole arrest in the absence or presence of decoy peptide treatment; B: protein expression of cyclin E and Geminin U2OS cells transfected with vector backbone (vehicle) or pRc/cyclin E and pCMV/Cdk2 arrested at the G2/M boundary by exposure to nocodazole (75 ng/ml) and then released to re-enter the cell cycle; C: western blots (WB) or commassie stained gels showing Geminin expression in the absence or presence of cyclin E/Cdk2 overexpression (left panel) or in the absence or presence of decoy peptide treatment (right panel);

FIG. 10 is A: a schematic diagram demonstrating post-transcriptional suppression of gene expression by DNA enzymes; B: a depiction of the sequence and loop structure of the DNA enzymes targeting TRIP-Br transcripts;

FIG. 12 is A: viable cell counts of sub-confluent WI-38 cells serum-starved for 72 h, transfected with DNA enzyme and then re-stimulated with serum for 72 h; B: photographs of cells from A stained in situ with crystal violet;

FIG. 15 is A: BrdU incorporation determined by colorimetric ELISA assay on sub-confluent PMEF cultures (TRIP-Br2$^{+/+}$ and $^{-/-}$); B: viable cell count analysis of sub-confluent PMEFs serum-starved for 72 h and then re-stimulated with serum; C: semi-quantitative RT-PCR analysis to assess CCNE expression in wild-type (+) or TRIP-Br2 null (−) PMEFs;

FIG. 20 is a CLUSTAL W (1.81) multiple sequence alignment of human and mouse TRIP-Br proteins;

DETAILED DESCRIPTION

Figure 1:
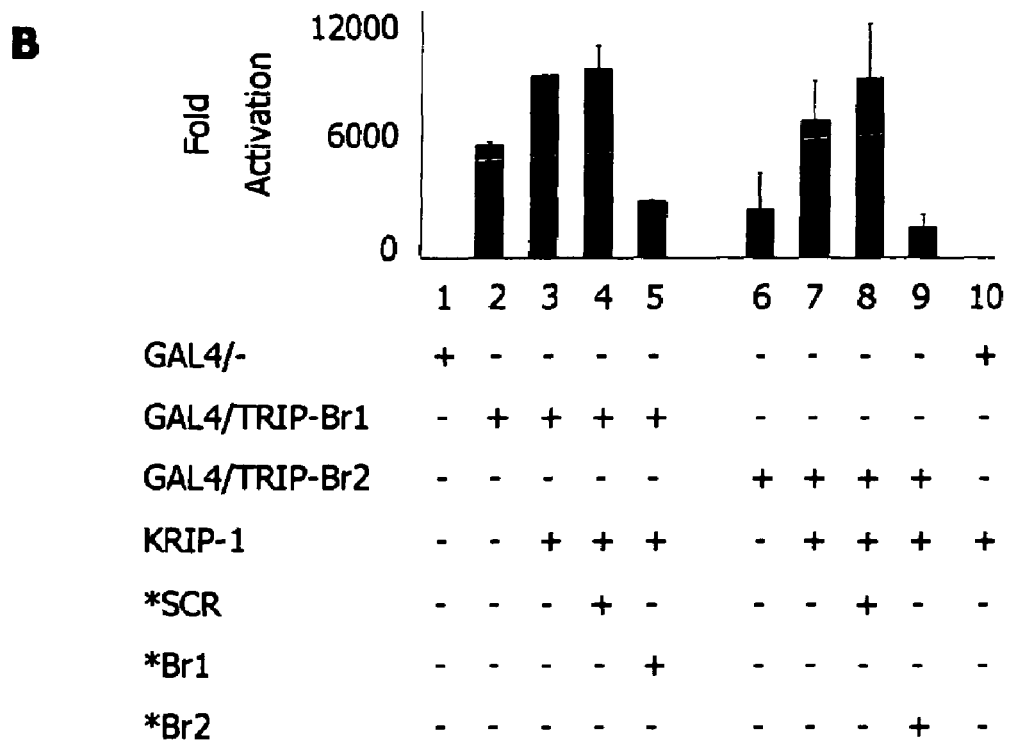
FIG. 1 is A: an autoradiogram of an immunoprecipitation assay of KRIP-1/TRIP-Br; B: a graph depicting luciferase assay results of U2OS cells treated with the decoy peptides.

The inventors have determined that members of the TRIP-Br protein family play a role in mitogen-induced cell cycle progression. Treating proliferating cells so as to disrupt or modulate the integrator function of TRIP-Br family members induces a proliferative block. It appears that such modulation may exert anti-proliferative effects by down-regulating the transcriptional activity of a subset of growth-regulating E2F-responsive genes in vivo and inducing aberrant cyclin E accumulation by abrogating the cell cycle regulatory activity of cyclin E/Cdk2. This in turn may lead to Geminin deregulation and progressive cellular sub-diploidization. The cyclin E deregulation may be attributable to the down-regulation of Fbxw7, a gene encoding the Fbw7 receptor subunit of the $SCF^{FBW7}$ ubiquitin ligase (E3) responsible for targeting cyclin E for proteolysis. Fbxw7 is identified herein as an E2F-responsive gene. The inventors have determined that TRIP-Br proteins appear to be involved in mediating the proper execution of one or more regulatory steps upstream of cyclin E/Cdk2 in the mitogenic cell cycle signaling pathway. Furthermore, the inventors demonstrated that downregulation of TRIP-Br protein expression disrupts mitogenic signaling in a manner that suppresses serum-induced cyclin E expression, S phase entry and cellular proliferation.

Thus, the present methods relate to modulation of the function of proteins of the TRIP-Br family in uncontrolled proliferating cells. Such modulation results in induction of a proliferative block within such cells, allowing for treatment of proliferative disorders.

The TRIP-Br protein family is a family of structurally and functionally related mammalian transcriptional regulators and includes TRIP-Br1 and TRIP-Br2.

Human TRIP-Br1 (hTRIP-Br1) is identical to $p34^{SEI-1}$, a mammalian protein that has recently been identified as a cyclin-dependent kinase 4 (Cdk4)-binding protein (Sugimoto, M., et al., *Genes Dev* 13, 3027-3033 (1999)). TRIP-Br2 was later discovered as a homologue of TRIP-Br1 based on structural and functional homology to TRIP-Br1 (Hsu et al., supra). In addition, endogenous TRIP-Br1 protein has been found to be regulated during the cell cycle, the level of expression being highest during S phase (Hsu et al., supra).

TRIP-Br1 and TRIP-Br2 possess potent C-terminal acidic transactivation domains that are highly homologous to that of the p53-associated transcription factor MDM2 (Hsu et al., supra; Keyomarsi, K., and Herliczek, T. W., (1997), *Prog Cell Cycle Res* 3: 171-191). Like MDM2, the TRIP-Br proteins appear to interact functionally with DP-1, resulting in the stimulation of E2F-1/DP-1 transcriptional activity. This co-activation function of the TRIP-Br proteins may occur through direct interaction with DP-1. It has been previously demonstrated that hTRIP-Br1 is a component of an endogenous multiprotein complex containing E2F-1 and DP-1.

The mouse TRIP-Br1 (mTRIP-Br1) protein was first isolated in a yeast two-hybrid screen designed to identify proteins that interact with the composite plant homeo domain (PHD)-bromodomain of the transcriptional co-repressor KRIP-1 (KAP-1 or TIF1β) (Hsu, S. I. H., et al., *EMBO J.* 20, 2273-2285 (2001); Kim, S.-S., et al., *Proc Natl Acad Sci USA* 93, 15299-15304 (1996); Le Douarin, B., et al., *EMBO J.* 15, 6701-6715 (1996); Moosmann, P., et al., *Nucl Acids Res* 24, 4859-4867 (1996)).

The TRIP-Br proteins have been shown to function as physiological integrators of transcriptional regulatory signals at E2F-responsive promoters, integrating regulatory signals provided by PHD zinc finger- and/or bromodomain-containing transcription factors, such as p300/CBP and KRIP-1 (Kalkhoven, E., et al., *Mol Cell Biol* 22, 1961-1970 (2002); Schultz, D. C., et al., *Genes Dev* 15, 428-433 (2001)). Thus, the TRIP-Br proteins contribute to the regulation of E2F-dependent cell cycle progression (Hsu, S. I. H., et al., *EMBO J* 20, 2273-2285 (2001))

The PHD zinc fingers and the bromodomains are evolutionarily conserved protein secondary structures found in a host of chromatin-remodeling proteins. Such domains have been proposed to serve as protein-protein interaction domains important for chromatin-dependent transcriptional regulation (Aasland, R., et al. *Trends Biochem Sci* 20, 56-59 (1995); Capili, A. D., et al. *EMBO* 20, 165-177 (2001); Marmorstein, R. B., et al. *Gene* 272, 1-9 (2001)). For example, the tandem PHD zinc finger and bromodomain of KRIP-1 has been shown to form a cooperative unit that functions to target the histone deacetylase and chromatin remodeling activities of the NuRD complex, which is required for gene silencing, to specific gene promoters in vivo.

The PHD zinc finger features a cysteine4-histidine-cysteine3 (Cys4-His-Cys3) zinc finger motif (Koken, M. H. M., et al., *C R Acad Sci III* 318, 733-739 (1995)), while the bromodomain is a ~110-amino-acid structural module encoding four amphipathic α-helical subdomains that interact with acetylated lysine residues (Haynes, S., et al. *Nucl Acids Res* 20, 2603 (1992); Zeng, L., and Zhou, M.-M. *FEBS Letters* (2002) 513(1):124-8). Both TRIP-Br1 and TRIP-Br2 demonstrate the ability to interact with the PHD zinc finger and/or the bromodomain. These protein-protein interactions have been implicated in the co-regulation of E2F-dependent transcription (Hsu et al., supra).

Thus, there is provided a method of inhibiting proliferation of mammalian cells, which involves modulating the transcriptional integrator activity of the TRIP-Br proteins.

As used herein, TRIP-Br refers to any member of the TRIP-Br family, including TRIP-Br1 and TRIP-Br2. TRIP-Br family members possess a "PHD-bromodomain interacting region" that interacts with a PHD zinc finger and/or a bromodomain in a protein involved in cellular functions including, but not limited to, cell cycle regulation, gene transcriptional regulation and proliferation. The term includes homologs, fragments, derivatives or variants of TRIP-Br that possess the transcriptional integrator activity of TRIP-Br.

A polynucleotide sequence or polypeptide sequence is a "homolog" of, or is "homologous" to another sequence if the two sequences have substantial identity over a specified region and the functional activity of the sequences is conserved (as used herein, the term "homologous" does not imply evolutionary relatedness). Two polynucleotide sequences or polypeptide sequences are considered to have substantial identity if, when optimally aligned (with gaps permitted), they share at least approximately 50% sequence identity, or if the sequences share defined functional motifs. In alternative embodiments, optimally aligned sequences may be considered to be substantially identical (i.e. to have substantial identity) if they share at least 60%, 70%, 75%, 80%, 85%, 90%, 95%, 96%, 97%, 98%, 99% identity over a specified region. An "unrelated" or "non-homologous" sequence shares less than 40% identity, and possibly less than approximately 25% identity, with a polypeptide or polynucleotide of the invention over a specified region of homology. The terms "identity" and "identical" refer to sequence similarity between two peptides or two polynucleotide molecules. Identity can be determined by comparing each position in the aligned sequences. A degree of identity between amino acid sequences is a function of the number of identical or matching amino acids at positions shared by the sequences, i.e. over a specified region. Optimal alignment of sequences for comparisons of identity may be conducted using a variety of algorithms, as are known in the art, including the ClustalW program, available at http://clustalw.genome.ad.jp, the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis are available through the National Center for Biotechnology Information (through the internet at http://www.ncbi.nlm.nih.gov/). As used herein, "homologous amino acid sequence" includes any polypeptide which is encoded, in whole or in part, by a nucleic acid sequence which hybridizes at 25-35° C. below critical melting temperature (Tm), to any portion of a nucleic acid sequence encoding mammalian TRIP-Br, including TRIP-Br1 or TRIP-Br2, including a nucleic acid encoding any one of the amino acid sequences of SEQ ID NO. 12 to 15.

A variant or derivative of TRIP-Br refers to a TRIP-Br or a fragment thereof, which retains the transcriptional integrator activity of TRIP-Br, or a TRIP-Br that has been mutated at one or more amino acids, including point, insertion or deletion mutations, but still retains the transcriptional integrator activity of TRIP-Br. A variant or derivative therefore includes deletions, including truncations and fragments; insertions and additions, for example conservative substitutions, site-directed mutants and allelic variants; and modifications, including peptoids having one or more non-amino acyl groups (q.v., sugar, lipid, etc.) covalently linked to the peptide and post-translational modifications. As used herein, the term "conserved amino acid substitutions" or "conservative substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

The "transcriptional integrator activity" or "integrator activity" of TRIP-Br refers to the ability of TRIP-Br to interact with various transcription factors and proteins, including but not limited to, proteins involved in cell cycle regulation, gene transcriptional regulation and proliferation. The transcriptional integrator function is moderated at least by the PHD-bromodomain interacting region of TRIP-Br.

The term "cell" refers to a single cell, a plurality of cells or a population of cells, unless otherwise indicated herein. The cell may be any cell in which proliferation or division is desired to be inhibited, including a cell that has lost the ability to undergo cell cycle arrest or apoptosis. The cell may be a cell in culture or it may be a cell within a patient. As used herein, proliferation of a cell refers to the process of DNA replication, growth and division, which leads to an increase in the total number of cells. The cell may be derived from any organism that expresses a TRIP-Br homolog, and in particular embodiments is a mammalian cell, including a mouse cell, a rat cell, a rabbit cell or a human cell.

The term "inhibiting proliferation" in a cell or "inhibition of proliferation" of a cell includes rendering the cell incapable of replicating DNA, growing or dividing, or incapable of properly replicating DNA, growing or dividing, or reducing or retarding DNA replication, cell growth or division, in addition to inducing cell death by apoptosis or other mechanisms of cell death. Inhibiting may be performed in vitro or in vivo.

"Modulating", or "modulation of", the transcriptional integrator activity of TRIP-Br refers to any mechanism of upregulating, deregulating, stimulating, activating, increasing, disrupting, interrupting, reducing, limiting, blocking or preventing the ability of TRIP-Br to perform its biological function or activity, including integrating transcription regulatory signals involved in regulating proliferation, replication or cell cycle progression, thereby resulting in an inhibition of proliferation. Modulation includes physical alteration of TRIP-Br, for example by post-translational modification, loss or lack of necessary post-translational modification, mutation of the amino acid sequence, including deletion, insertion and substitution mutation, or protein digestion. Modulation also includes stabilizing, inducing, antagonizing, inhibiting, or competing with, the interaction between TRIP-Br and transcriptional regulatory factors which are targets of TRIP-Br, and which TRIP-Br interacts with to effect cell cycle progression, including an interaction between the PHD/bromodomain interacting region of TRIP-Br and a transcription factor containing a PHD zinc finger and/or a bromodomain. Modulation also includes genetic modification which results in substantially decreased or no expression of functional TRIP-Br. "Substantially decreased" and "substantially less" refers to levels of expression of TRIP-Br or functional TRIP-Br that are, for example, approximately 50%, 45%, 40%, 35%, 30%, 25%, 20%, 15%, 10%, 5% or 0% of the levels of expression of functional TRIP-Br that would occur in an unmodulated cell. Such genetic modification includes a modification of a nucleic acid encoding TRIP-Br, including a TRIP-Br gene, such that part, or all, of the open reading frame has been deleted, replaced or interrupted such that substantially less or no gene product, no stable gene product, or no functional gene product is expressed. Such genetic modification also includes modification of a nucleic acid encoding TRIP-Br, including a TRIP-Br gene, such that part, or all, of the TRIP-Br gene regulatory region has been deleted, replaced, interrupted or inhibited, resulting in substantially less or no protein being expressed from the gene encoding TRIP-Br. Functional TRIP-Br protein is TRIP-Br, or a fragment of TRIP-Br, that is translated, folded, post-translationally modified and localized within the cell, and which possesses the biological function or activity or TRIP-Br, which may include the transcriptional integrator function of TRIP-Br. Under any context in which the TRIP-Br protein is not, or not properly, translated, folded, post-translationally modified or localized within the cell, even if the gene is transcribed, a proliferative block may ensue. Such genetic modification further includes modifying the cell to transcribe an antisense RNA transcript that is complementary to at least a fragment of the mRNA molecule that is transcribed from the TRIP-Br gene, resulting in no translation, or reduced translation of the TRIP-Br transcript. Such genetic modification further includes modifying the cell to transcribe or express a small interfering RNA (siRNA) molecule that targets a TRIP-Br gene transcript, resulting in no translation, or reduced translation of the TRIP-Br transcript.

In some embodiments, the transcriptional integrator function of TRIP-Br is modulated by a modulator molecule. The modulator may be any molecule that competes with or mimics the binding of the PHD-bromodomain interacting region of TRIP-Br, thereby binding to the target of the PHD-bromodomain interacting region and blocking or reducing the ability of TRIP-Br to bind to its target.

The modulator may be capable of being delivered internally to a cell, for example by active or passive transport into the cell, or by diffusion into the cell. For example, if the modulator is a small molecule, it may be soluble in the cell membrane and thus able to permeate the cell. The modulator may also be modified to include a transport tag that will facilitate its transport into a cell. Specific transport tags may be used in order to direct the modulator to be taken up by specific target cells. For example, the modulator may be modified to include a galactose residue to increase uptake of the modulator by hepatocytes, as is described in U.S. Pat. No. 6,844,319, which is herein fully incorporated by reference. Alternatively, the modulator may be included in a biomaterial which increases or induces uptake of the modulator by the cell, for example, by encapsulating the modulator in a liposome preparation. Liposome delivery of peptides and proteins to cells is known, and is described for example in U.S. Pat. No. 6,372,720 and US 20030108597, which are incorporated herein by reference.

In one embodiment, the modulator is a peptide encoding the sequence of the PHD-bromodomain interacting region of TRIP-Br, including the sequence of the PHD-bromodomain interacting region of either TRIP-Br1 or TRIP-Br2. The peptide modulator may be a peptide containing a sequence having 60%, 70%, 75%, 80%, 85%, 90%, 95%, 96%, 97%, 98% or 99% identity to the PHD-bromodomain interacting region of TRIP-Br. Generally, some modifications and changes can be made in the structure of a polypeptide without substantially altering the biological activity of that peptide, to obtain a functionally equivalent polypeptide. Thus, the present invention extends to biologically equivalent polypeptides that differ from a portion of the amino acid sequence of the PHD-bromodomain interacting region of TRIP-Br and biologically active or immunogenic fragments thereof by conservative amino acid substitutions. As used herein, the term "conservative amino acid substitution" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr. Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cysteic acid, epsilon-amino hexanoic acid, delta-amino valeric acid, and 2,3-diaminobutyric acid.

In some embodiments, the peptide may contain a sequence of the formula UTGXLXDXXLZJOLFJDID [SEQ ID NO. 16], wherein X is any amino acid; U is S, T, A or no amino acid; Z is D or E; J is D, E, A or G; O is I, L, V, A or no amino acid.

In specific embodiments, the modulator is a peptide including the amino acid sequence ATGCLLDDGLEGLFEDID [SEQ ID NO. 1] from human TRIP-Br1 or TGFLTDLTLDDILFADID [SEQ ID NO. 2] from human TRIP-Br2.

In further embodiments, the modulator peptide further comprises a sequence such as a membrane-translocating sequence that allows the peptide in which it is included to transported into a cell, for example the penetratin sequence derived from the *Drosophila melanogaster* antennapedia homeodomain protein, for example having the sequence ERQIKIWFQNRRMKWKK [SEQ ID NO. 3]. Thus, in particular embodiments, the modulator peptide includes the sequence ERQIKIWFQNRRMKWKKATGCLLDDGLEGLFEDID [SEQ ID NO. 4] or ERQIKIWFQNRRMKWKKTGFLTDLTLDDILFADID [SEQ ID NO. 5].

Alternatively, the peptide modulator may be incorporated into a larger fusion protein in order to increase the stability of the protein and to assist in delivery to a target cell. The fusion protein may be designed to incorporate a specific protease cleavage site for recognition by a protease expressed in the target cell so that the peptide modulator is released from the fusion protein upon entry into the target cell.

A peptide modulator can be synthesized using standard protein synthesis techniques as are known in the art, for example using chemical peptide ligation methods, including solid phase peptide synthesis, to synthesize the peptide in the C-terminal to N-terminal direction, including using an automated peptide synthesizer. Alternatively, molecular biology techniques may be used to design an expression cassette that will encode the peptide modulator, using standard molecular biology techniques known in the art, and described for example in Sambrook et al. ((2001) Molecular Cloning: a Laboratory Manual, 3$^{rd}$ ed., Cold Spring Harbour Laboratory Press). The expression cassette can be used in a suitable expression system. For example, the cassette may be contained in a bacterial plasmid and may be expressed in a bacterial cell, from which the peptide modulator can be isolated and purified. The expression cassette will contain an open reading frame encoding the peptide modulator, optionally as a complete peptide or as part of a chimeric or fusion peptide or protein, from which the peptide may be released, for example by protease digestion. The expression cassette will also contain suitable regulatory regions operably linked to the open reading frame, for example a promoter region, which may be an inducible promoter region.

In this embodiment, modulation of protein-protein interaction is achieved by exposure of the cell to the modulator, allowing for uptake of the modulator by the cell, allowing the modulator to interact with a PHD zinc finger containing, and/or bromodomain containing target of TRIP-Br protein, thereby reducing or blocking the ability of the TRIP-Br protein to effect its activity, such as its transcriptional integrator function in the cell. Where the modulator is a peptide, inclusion of the penetratin sequence, or any sequence which allows for peptide transport into a cell, facilitates the uptake of the modulator by the cell.

Alternatively, in other embodiments, the modulation is achieved using a molecule capable of inhibiting expression of nucleic acid encoding TRIP-Br, including a TRIP-Br gene.

The molecule capable of inhibiting expression of nucleic acid encoding TRIP-Br, including a TRIP-Br gene, may be a DNA enzyme that targets the transcript of a gene encoding TRIP-Br. A DNA enzyme is a magnesium-dependent catalytic nucleic acid composed of DNA that can selectively bind to an RNA substrate by Watson-Crick base-pairing and potentially cleave a phosphodiester bond of the backbone of the RNA substrate at any purine-pyrimidine junction (Santiago, F. S., et al., (1999) *Nat Med* 5: 1264-1269). A DNA enzyme is composed of two distinct functional domains: a 15-nucleotide catalytic core that carries out phosphodiester bond cleavage, and two hybridization arms flanking the catalytic core; the sequence identity of the arms can be tailored to achieve complementary base-pairing with target RNA substrates.

The DNA enzyme will therefore have complementary regions that can anneal with regions on the transcript of a TRIP-Br gene flanking a purine-pyrimidine junction such that the catalytic core of the DNA enzyme is able to cleave the transcript at the junction, rendering the transcript unable to be translated to produce a functional TRIP-Br protein. In certain embodiments, the DNA enzyme is designed to cleave the TRIP-Br transcript between the A and the U residues of the AUG start codon. In particular embodiments, the DNA enzyme includes the sequence T TAC CCA ACA <u>GGCTAGCTACAACGA</u> ATA TCA CA [SEQ ID NO.: 6] or T TGC TCA GCA <u>GGCTAGCTACAACGA</u> CTT GCT CA [SEQ ID NO.: 7], in which the underlined text indicates the sequence of the catalytic core.

The DNA enzyme may be synthesized using standard techniques known in the art, for example, standard phosphoramidite chemical ligation methods may be used to synthesize the DNA molecule in the 3' to 5' direction on a solid support, including using an automated nucleic acid synthesizer. Alternatively, the DNA enzyme may be synthesized by transcribing a nucleic acid molecule encoding the DNA enzyme. The nucleic acid molecule may be contained within a DNA or RNA vector, for delivery into a cellular expression system, for example, a viral vector. Suitable viral vectors include vaccinia viral vectors and adenoviral vectors.

In this embodiment, the modulation is achieved by exposing the cell to the DNA enzyme so that the DNA enzyme is taken up by the cell, and is able to target and cleave a TRIP-Br transcript in the cell, resulting in decreased or no expression of functional TRIP-Br protein in the cell. Exposure may include transfection techniques, as are known in the art, or by microinjection techniques in which the DNA is directly injected into the cell. Exposure may also include exposing the cell to the naked DNA enzyme, as cells may take up naked DNA in vivo. Alternatively, if the DNA enzyme is included in a nucleic acid vector, such as a viral vector, the cell may be infected with the viral vector.

Alternatively, the molecule capable of inhibiting expression of nucleic acid encoding TRIP-Br, including a TRIP-Br gene, may be an antisense RNA molecule or a small interfering RNA (siRNA) molecule.

The antisense RNA molecule will contain a sequence that is complementary to at least a fragment of an RNA transcript of a TRIP-Br gene, and which can bind to the TRIP-Br transcript, thereby reducing or preventing the expression of the TRIP-Br gene in vivo. The antisense RNA molecule will have a sufficient degree of complementarity to the target mRNA to avoid non-specific binding of the antisense molecule to non-target sequences under conditions in which specific binding is desired, such as under physiological conditions.

The siRNA molecule may be any double-stranded RNA molecule, including a self-complementary single-stranded molecule that can fold back on itself to form the double-stranded siRNA, which induces gene-specific RNA interference in a cell, leading to decreased or no expression of the TRIP-Br gene in vivo. An siRNA typically targets a 19-23 base nucleotide sequence in a target mRNA, as described in Elbashir, et al. (2001) *EMBO J.* 20: 6877-6888, the contents of which is incorporated herein by reference.

In order to effect the modulation, the cell is exposed to the antisense RNA, a nucleotide encoding the antisense RNA, the siRNA or a nucleotide encoding the siRNA, for example a nucleic acid vector containing a nucleic acid molecule which allows for transcription of an antisense transcript or a single-stranded, self-complementary siRNA molecule capable of forming a double-stranded siRNA. Such an antisense molecule, siRNA molecule or vector may be synthesized using nucleic acid chemical synthesis methods and standard molecular biology cloning techniques as described above.

There is also presently provided a method of treating a proliferative disorder in a patient. The method involves modulating the activity of TRIP-Br1, including the transcriptional integrator activity of TRIP-Br1, in a proliferating cell of the patient, wherein the proliferating cell is associated with the proliferative disorder.

A "proliferative disorder" is a disease or disorder in which a cell of a patient is abnormally proliferating, resulting in uncontrolled growth and division of the cell, which in a healthy individual would not be proliferating or would be proliferating in a controlled manner. The proliferative disorder may be characterized by the proliferation of malignant or non-malignant cell populations. Such disorders include cancer including bladder cancer, colon cancer, prostate cancer, lung cancer, nasopharyngeal carcinoma, cervical carcinoma, skin cancer, leukemia; hyperplastic skin lesions including genital warts, psoriasis and keloids; ischemic heart disease, acquired immune deficiency syndrome, vasculitis, rheumatoid arthritis, athersclerosis, glomerulonephritis leading to glomerulosclerosis, interstitial inflammation leading to fibrosis, pulmonary inflammation leading to fibrosis. A proliferating disorder includes abnormal proliferation which may also occur during normal wound healing, potentially leading to excessive scarring or keloid formation, and which may occur during any inflammatory condition leading to tissue injury in which host immune cells trigger fibroblasts to proliferate and elaborate extracellular matrix components leading to fibrosis. Examples of the latter include the host immune response to cerebral infarction (stroke), myocardial infarction (heart attack) and acute ischemic renal tubular injury (transient kidney failure).

A cell is associated with a proliferative disorder if that cell is a cell that is abnormally proliferating so as to result in the disorder in the patient, or if the disorder is characterized by the proliferation of such a cell.

The term "treating" a proliferative disorder refers to an approach for obtaining beneficial or desired results, including clinical results. Beneficial or desired clinical results can include, but are not limited to, alleviation or amelioration of one or more symptoms or conditions, diminishment of extent of disease, stabilization of the state of disease, prevention of development of disease, prevention of spread of disease, delay or slowing of disease progression, delay or slowing of disease onset, amelioration or palliation of the disease state, and remission (whether partial or total). "Treating" can also mean prolonging survival of a patient beyond that expected in the absence of treatment. "Treating" can also mean inhibiting the progression of disease, slowing the progression of disease temporarily, although more preferably, it involves halting the progression of the disease permanently.

The patient is any animal in need of treatment of a proliferative disorder, including a mammal, including a mouse, rat, rabbit or human.

The therapeutic effect is achieved by administering to the patient a molecule capable of modulating the activity of TRIP-Br. In one embodiment, the molecule is a molecule capable of modulating the transcriptional integrator activity of TRIP-Br. The molecule capable of modulating the activity of TRIP-Br is any molecule that may be used to effect modulation in a cell as described above, including a modulator that mimics the binding of the PHD-bromodomain interacting region of TRIP-Br, thereby binding to the target of the PHD-bromodomain interacting region and blocking or reducing the ability of TRIP-Br to bind to its target. Such a modulator may be for example a small molecule or a peptide, as described above. The molecule capable of modulating the activity of TRIP-Br1 may be a DNA enzyme, as described above, including a DNA enzyme molecule, or a nucleic acid molecule encoding a transcribable DNA enzyme. Alternatively, the molecule capable of modulating the activity of TRIP-Br may be a nucleic acid molecule encoding a transcribable antisense mRNA that contains a sequence that is complementary to a TRIP-Br mRNA transcript, or a molecule encoding an siRNA molecule that targets a TRIP-Br mRNA transcript.

An effective amount of the molecule capable of modulating the activity of TRIP-Br is administered to the patient. The term "effective amount" as used herein means an amount effective, at dosages and for periods of time necessary to achieve the desired result, for example, to treat the specific proliferative disorder.

The molecule is administered to the patient using standard techniques known in the art. The molecule may be administered systemically, or may be administered directly at the site at which the proliferating cell that is associated with the proliferative disorder is located. Delivery to the site includes topical administration, injection to the site, or surgical implantation, for example at a site of a tumour.

The concentration and amount of the molecule capable of modulating the activity of TRIP-Br to be administered will vary, depending on the proliferative disorder to be treated, the type of cell associated with the proliferative disorder, the type of molecule that is administered, the mode of administration, and the age and health of the patient.

To aid in administration, the molecule capable of modulating the activity of TRIP-Br may be formulated as an ingredient in a pharmaceutical composition. Therefore, in a further embodiment, there is provided a pharmaceutical composition comprising a molecule capable of modulating the activity of TRIP-Br, and a pharmaceutically acceptable diluent. The invention in one aspect therefore also includes such pharmaceutical compositions for use in treating a proliferative disorder. The compositions may routinely contain pharmaceutically acceptable concentrations of salt, buffering agents, preservatives and various compatible carriers. For all forms of delivery, the molecule capable of modulating the activity of TRIP-Br may be formulated in a physiological salt solution. Since peptides may be unstable upon administration, where the molecule capable of modulating the activity of TRIP-Br is a peptide or a protein, it may be desirable to include the peptide or the protein in a liposome or other biomaterial useful for protecting and/or preserving the peptide or protein until it is delivered to the target cell.

The pharmaceutical compositions may additionally contain other therapeutic agents useful for treating the particular proliferative disorder, for example a cytotoxic agent, for example a chemotherapeutic agent.

The proportion and identity of the pharmaceutically acceptable diluent is determined by chosen route of administration, compatibility with live cells, and standard pharmaceutical practice. Generally, the pharmaceutical composition will be formulated with components that will not kill or significantly impair the biological properties of the molecule capable of modulating the activity of TRIP-Br.

The pharmaceutical composition can be prepared by known methods for the preparation of pharmaceutically acceptable compositions suitable for administration to patients, such that an effective quantity of the molecule capable of modulating the activity of TRIP-Br, and any additional active substance or substances, is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the pharmaceutical compositions include, albeit not exclusively, solutions of the molecule capable of modulating the activity of TRIP-Br1, in association with one or more pharmaceutically acceptable vehicles or diluents, and contained in buffer solutions with a suitable pH and iso-osmotic with physiological fluids.

The pharmaceutical composition may be administered to a patient in a variety of forms depending on the selected route of administration, as will be understood by those skilled in the art. The composition of the invention may be administered topically, surgically or by injection to the desired site.

Solutions of the molecule capable of modulating the activity of TRIP-Br may be prepared in a physiologically suitable buffer. Under ordinary conditions of storage and use, these preparations contain a preservative to prevent the growth of microorganisms, and that will maintain the function of the molecule capable of modulating the activity of TRIP-Br. A person skilled in the art would know how to prepare suitable formulations. Conventional procedures and ingredients for the selection and preparation of suitable formulations are described, for example, in Remington's Pharmaceutical Sciences and in The United States Pharmacopeia: The National Formulary (USP 24 NF19) published in 1999.

In different embodiments, the composition is administered topically or by injection (subcutaneously, intravenously, intramuscularly, etc.) directly at the desired site where the cells that are proliferating in an uncontrolled manner are located in the patient.

The dose of the pharmaceutical composition that is to be used depends on the particular condition being treated, the severity of the condition, the individual patient parameters including age, physical condition, size and weight, the duration of the treatment, the nature of concurrent therapy (if any), the specific route of administration and other similar factors that are within the knowledge and expertise of the health practitioner. These factors are known to those of skill in the art and can be addressed with minimal routine experimentation.

Also presently contemplated are molecules capable of modulating the activity of TRIP-Br as described herein, including a peptide modulator of TRIP-Br, a DNA enzyme that targets a TRIP-Br transcript, an antisense RNA that is complementary to at least a portion or fragment of a TRIP-Br transcript or a small interfering RNA molecule that targets a TRIP-Br transcript. In specific embodiments, the molecule is a peptide comprising a sequence having the formula UTGXLXDXXLZJOLFJDID [SEQ ID NO.: 16], wherein X is any amino acid; U is S, T, A or no amino acid; Z is D or E; J is D, E, A or G; and O is I, L, V, A or no amino acid. In particular embodiments, the peptide modulator is a peptide comprising SEQ ID NO.1 or SEQ ID NO.2, and may further comprise SEQ ID NO.3. In particular embodiments the peptide comprises SEQ ID NO.4 or SEQ ID NO.5, or has the sequence of SEQ ID NO.4 or SEQ ID NO.5. In certain embodiments, the molecule is a DNA enzyme comprising the sequence of SEQ ID NO.6 or SEQ ID NO.7, or having the sequence of SEQ ID NO.6 or SEQ ID NO.7. Also presently contemplated are uses of such molecules, including uses for modulating the transcriptional integrator activity of TRIP-Br for treating a proliferative disorder in a patient, for preparation of a medicament for modulating the transcriptional integrator activity of TRIP-Br or for preparation of a medicament for treating a proliferative disorder in a patient.

A method for identifying or screening for modulators of TRIP-Br, including small molecule or peptide modulators, is also provided. Test molecules are used to compete with the binding of the PHD-bromodomain interacting region of TRIP-Br with a cellular protein target of TRIP-Br. A cellular protein target of TRIP-Br may be, for example, a protein containing a PHD zinc finger or a bromodomain, including for example the protein KRIP-1 or the protein p300/CBP. Thus, a cellular protein target of TRIP-Br is contacted with a peptide comprising the PHD-bromodomain interacting region of TRIP-Br in the presence of the test compound, and the effect of the test compound on the binding between the cellular protein target of TRIP-Br and the PHD-bromodomain interacting region of TRIP-Br is monitored. Such competition assays, and methods of measuring interruption of protein-protein interactions are known, and include chromatography assays, immunoassays, immobilization assays, immunoprecipitation techniques, gel retardation assays. The methods of screening for modulators of TRIP-Br are well suited for screening combinatorial libraries of compounds.

The present invention also contemplates antibodies directed against TRIP-Br, particularly against TRIP-Br1 or TRIP-Br2. An antibody of the invention is either polyclonal or monoclonal. Monospecific antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies may also be in the form of immunoglobulin fragments, e.g., F(ab)'2 or Fab fragments. The antibodies of the invention are of any isotype, e.g., IgG or IgA, and polyclonal antibodies are of a single isotype or a mixture of isotypes.

In particular embodiments, the antibody is a mouse monoclonal antibody directed against the human peptide sequence DPGHTAAVAQAPPAVAS [SEQ ID NO.: 10] or SVADNLLASSDAALS [SEQ ID NO.: 11] of TRIP-Br1.

Antibodies against TRIP-Br are generated by immunization of a mammal with a composition comprising a polypeptide, homolog or fragment of TRIP-Br. Methods to produce polyclonal or monoclonal antibodies are well known in the art. For a review, see "Antibodies, A Laboratory Manual, Cold Spring Harbor Laboratory, Eds. E. Harlow and D. Lane (1988), and D. E. Yelton et al., 1981. Ann. Rev. Biochem. 50:657-680; for monoclonal antibodies, see Kohler & Milstein (1975) Nature 256:495-497.

The antibodies are useful in diagnostic methods to detect the presence of a TRIP-Br antigen in a sample, such as a biological sample, including a sample of cells undergoing or suspected of undergoing uncontrolled proliferation, or which are being treated or have been treated to prevent proliferation. The antibodies are also used in affinity chromatography for purifying TRIP-Br.

Briefly, for making monoclonal antibodies, somatic cells from a host animal immunized with antigen, with potential for producing antibody, are fused with myeloma cells, forming a hybridoma of two cells by conventional protocol. Somatic cells may be derived from the spleen, lymph node, and peripheral blood of transgenic mammals. Myeloma cells which may be used for the production of hybridomas include murine myeloma cell lines such as MPCII-45.6TGI.7, NSI-Ag4/1, SP2/0-Ag14, X63-Ag8.653, P3-NS-1-Ag-4-1, P.sub.3×63Ag8U.sub.1, OF, and S194/5XX0.BU.1; rat cell lines including 210.RCY3.Agl.2.3; cell lines including U-226AR and GM1500GTGA1.2; and mouse-human heteromyeloma cell lines (Hammerling, et al. (editors), Monoclonal Antibodies and T-cell Hybridomas IN: J. L. Turk (editor) Research Monographs in Immunology, Vol. 3, Elsevier/North Holland Biomedical Press, New York (1981)).

Somatic cell-myeloma cell hybrids are plated in multiple wells with a selective medium, such as HAT medium. Selective media allow for the detection of antibody producing hybridomas over other undesirable fused-cell hybrids. Selective media also prevent growth of unfused myeloma cells which would otherwise continue to divide indefinitely, since myeloma cells lack genetic information necessary to generate enzymes for cell growth. B lymphocytes derived from somatic cells contain genetic information necessary for generating enzymes for cell growth but lack the "immortal" qualities of myeloma cells, and thus, last for a short time in selective media. Therefore, only those somatic cells which have successfully fused with myeloma cells grow in the selective medium. The unfused cells were killed off by the HAT or selective medium.

A screening method is used to examine for potential anti-TRIP-Br antibodies derived from hybridomas grown in the multiple wells. Multiple wells are used in order to prevent individual hybridomas from overgrowing others. Screening methods used to examine for potential anti-TRIP-Br antibodies include enzyme immunoassays, radioimmunoassays, plaque assays, cytotoxicity assays, dot immunobinding assays, fluorescence activated cell sorting (FACS), and other in vitro binding assays.

Hybridomas which test positive for anti-TRIP-Br antibody are maintained in culture and may be cloned in order to produce monoclonal antibodies specific for TRIP-Br.

Alternatively, desired hybridomas can be injected into a histocompatible animal of the type used to provide the somatic and myeloma cells for the original fusion. The injected animal develops tumors secreting the specific monoclonal antibody produced by the hybridoma.

The monoclonal antibodies secreted by the selected hybridoma cells are suitably purified from cell culture medium or ascites fluid by conventional immunoglobulin purification procedures such as, for example, protein A-Sepharose hydroxylapatite chromatography, gel electrophoresis, dialysis, or affinity chromatography.

All documents referred to herein are fully incorporated by reference.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. All technical and scientific terms used herein have the same meaning as commonly understood by one of ordinary skill in the art of this invention, unless defined otherwise.

EXAMPLES

Example 1

Use of Decoy Peptides to Disrupt TRIP-Br Interactions with PHD Zinc Finger and Bromodomains Materials and Methods Recombinant DNA and synthetic peptides. The pGL3-6xE2F-TATA/Luciferase reporter plasmid and the corresponding minimal reporter, pGL3-TATA/Luciferase, were kind gifts from Dr. Kristian Helin (European Institute of Oncology). The pRcSV/cyclin E and pCMV/Cdk2 were kind gifts from Dr. Steve Reed (The Scripps Research Institute, USA). The various plasmid DNA and cDNA clones for in vitro translation (IVT) and transfection experiments have been previously described (Hsu, S. I. H., et al. *EMBO J.* 20, 2273-2285 (2001)). Synthetic oligonucleotides were from GENSET, Singapore. Synthetic peptides and N-terminal fluoresceinated peptides were synthesized and purified by the Louisiana State University Health Sciences Center (LSUHSC) Core Facilities, USA. The following carboxyl-terminal amidated decoy peptides were synthesized (the penetratin tag sequence is underlined):

```
Br1:
EROIKIWFQNRRMKWKKATGCLLDDGLEGLFEDID    [SEQ ID NO.:4]

Br2:
EROIKIWFQNRRMKWKKTGFLTDLTLDDILFADID    [SEQ ID NO.:5]

SCR:
EROIKIWFQNRRMKWKKGLDEDGLLLFCEGDTIAD    [SEQ ID NO.:8]
```

The lyophilized peptide preparations were reconstituted in sterile Dimethyl Sulphoxide (DMSO) to make 25 mM stock solutions.

Tissue culture cell lines. All cell lines were maintained at 37° C. with 5% carbon dioxide ($CO_2$) in a humidified incubator. The human osteosarcoma cell line U2OS was cultured in Dulbecco's modified Eagle's medium (DMEM) supplemented with 10% fetal bovine serum (FBS) and anti-microbial agents (50 IU/ml penicillin, 50 μg/ml streptomycin and 50 μg/ml gentamycin). U2OS cells stably expressing ER-E2F-1 [a kind gift from Dr. Kristian Helin (European Institute of Oncology)] were cultured in DMEM supplemented with 10% FBS, 1.5 μg/ml puromycin and anti-microbial reagents. Cells used for experiments were between passages 2-15. In all decoy peptide experiments, cells were sub-cultured at a density of $5\times10^4$ cells/10 cm² for 24 h before treatment.

Biochemical reagents. Cycloheximide (C 7698) and 4-hydroxytamoxifen (OHT; H 7904) were purchased from Sigma. Mouse monoclonal antibody for human PARP (66391A) was purchased from Pharmingen. All other antibodies were purchased from Santa Cruz Biotechnology. The caspase-3 fluorogenic substrate Ac-DEVD-AFC (Bio-rad; 170-3178) and the apoptosis-inducing agent etoposide (eto) were kind gifts from Dr. Clement M. Veronique (National University of Singapore).

Preparation of proteins by in vitro translation. In vitro translation (IVT) products were synthesized from pcDNA3/TRIP-Br1, pcDNA3/TRIP-Br2 and pBlueScript/GAL4-KRIP-1 using the TNT T7 coupled reticulocyte lysate system (Promega). The in vitro translation reactions were carried out in a total reaction volume of 50 μl by incubating 1.0 μg of the indicated DNA template in nuclease-free water with 30 μl of TNT Quick master mix in the presence of $[^{35}S]$-methionine (Met) at 30° C. for 90 minutes.

Immunoprecipitation assay (IP). The binding reactions for IP were performed by incubating 1.5 μl $[^{35}S]$-Met labeled GAL4 or GAL4-KRIP-1 IVT products with 3 μl $[^{35}S]$-Met labeled TRIP-Br1 or TRIP-Br2 IVT products in 1×IP buffer (Hsu, S. I. H., et al. *EMBO J.* 20, 2273-2285 (2001)) at 4° C. for 1 h. For the analysis of decoy peptide-mediated blocking activity, the GAL4-KRIP-1 IVT product was pre-incubated with 25 μM decoy peptides at 4° C. for 30 minutes prior to addition of full-length TRIP-Br1 or TRIP-Br2 IVT products. Protein complexes precipitated using agarose-conjugated anti-GAL4 antibody were resolved by SDS-PAGE and then processed for autoradiography.

Confocal microscopy. For confocal microscopy, sub-confluent U2OS cells were cultured in 8-well chambers mounted on #1.0 German borosilicate cover glass (Lab-Tek®), and exposed to either vehicle (0.5% DMSO) or 20 μM of fluoresceinated decoy peptides for 24 h. Shortly before fluorescence imaging, treated cells were washed with 1×PBS and incubated in fresh, peptide-free medium to minimize background noise. Images were obtained with a Carl Zeiss 510 laser-scanning microscope using the plan-neafluar 40×/0.75 Ph2 objectives (laser excitation wavelength=488 nm; emission wavelength=500-550 nm).

Flow cytometric analyses. Analyses were performed using a Coulter EPICS® ELITE ESP flow cytometer at a laser wavelength of 488 nm. For the measurement of peptide internalization efficiency, U2OS cells grown in 6-well dishes were exposed to either vehicle (0.5% DMSO) or 50 μM of fluoresceinated decoy peptides for 24 h. At the time of harvest, cells were fixed with 2% paraformaldehyde followed by 70% ethanol. The proportion of cells exhibiting enhanced green fluorescence in each sample was determined using the WinMDI (version 2.7) computer software. Statistical analyses were done using the SPSS 8.0 software.

DNA Transfection and Sequential β-Galactosidase/Luciferase Assay. For luciferase reporter assays, U2OS cells were cultured in 6-well dishes and transfected 24 h later with various reporter plasmids by the calcium precipitation method as previously described (Martin, K., et al. *Nature* 375, 691-694 (1995)). 24 h following precipitate removal, cells were exposed for 5 h to either vehicle (0.5% DMSO) or 50 μM of decoy peptide, prior to harvesting. Cells were scraped in 200 µl of lysis buffer and a single 10 µl aliquot of lysate was immediately used for sequential measurement of β-galactosidase and luciferase activity using the Dual Light System (Tropix). For protein overexpression experiments, U2OS cells were cultured in 6-well plates at a density of 1×10$^5$ cells/well and transfected 24 h later with Superfect reagent (QIAGEN).

Semi-quantitative RT-PCR. Total RNA was isolated from U2OS cells or U2OS-ER-E2F-1 cells (grown with or without 1.0 µM OHT and/or 10 µg/ml cycloheximide) using the TRIZOL® Reagent (Life Technologies). Total RNA (4 µg) was reverse transcribed using oligo-dT and M-MLV reverse transcriptase in a total reaction volume of 20 µl. Polymerase Chain Reactions (PCR) were carried out on 3 µl cDNA samples in the presence of 25 mM deoxyribonucleotide triphosphates (dNTPs) and 40 µM of specific primer pairs in a total reaction volume of 50 µ. The cycling profile for PCR was as follow: 30 cycles of denaturation (94° C., 30 sec), annealing (51° C., 30 sec) and extension (72° C., 2 min), with a 2-minute initial denaturation step at 94° C. and a 10-minute terminal polishing step at 72° C. Sequences of gene-specific primers are available upon request. PCR amplification products were analyzed by agarose gel electrophoresis.

BrdU assay. U2OS cells grown in 96-well plates were exposed to either vehicle or decoy peptides. Bromodeoxyuridine (BrdU) incorporation was monitored with a colorimetric ELISA assay using a cell proliferation kit according to manufacturer's recommendations (Boehringer Mannheim).

Determination of cell number and viability. U2OS cells grown in 6-well dishes for 24 h were exposed to 2 ml of growth medium containing either vehicle (0.5% DMSO) or 50 µM decoy peptides for 48 or 72 h. Following treatment, the cells were washed twice with 1×PBS, harvested by trypsinization and re-suspended in 1 ml 1×PBS. 10 µl of cell suspension was taken from each sample and enumerated either electronically or manually. For electronic total cell counts, 10 µl of cell suspension was diluted in 20 ml of isoton® II buffer (Coulter®) and cell number was estimated using an electronic Coulter® counter. For manual counting of viable cells, 10 µl of cell suspension from each sample was mixed with equal volume of trypan blue stain (Sigma, 0.4% w/v in 1×PBS). The number of viable (unstained) cells was enumerated manually using a hemocytometer.

Cell synchronization and cell cycle progression analyses. U2OS cells in 6-well dishes were subjected to nocodazole treatment (75 ng/ml) for 22 h. Thereafter, the nocodazole-arrested cultures were released by washing with 1×PBS and grown in DMEM plus 10% FBS containing either vehicle (0.5% DMSO) or 20 µM decoy peptides. Cells were harvested at 4-h intervals for standard Western blot analyses. For the analysis of Geminin protein profile, mock- or cyclin E/Cdk2-transfected U2OS cells were exposed to nocodazole (75 ng/ml) at 3 h post-transfection for 22 h.

Protein decay analysis. Transfected or peptide-treated cells were exposed to 20 µg/ml cycloheximide (CHX). Whole cell lysates were prepared from the treated cells at 0, 1, 2, 3, 4 or 5-h post-CHX treatment for Western blot analysis.

Denaturing SDS-PAGE and western blotting. Proteins from whole cell lysate and IP complexes were separated using standard denaturing polyacrylamide gel electrophoresis as described previously (Hsu, S. I. H., et al. *EMBO J* 20, 2273-2285 (2001)).

Caspase assay. Both adherent and detached cells in 6-well dishes were harvested by centrifugation at 2000 rpm for 15 min at 4° C. The resulting cell pellets were incubated in 50 µl of chilled lysis buffer (Clontech) on ice for 10 min. Cell lysates were incubated in a reaction mix containing 10 mM HEPES, 2.0 mM EDTA, 10 mM KCl, 1.5 mM MgCl$_2$, 1.0 mM PMSF, aprotinine, pepstatin A and leupeptine (20 µM each), 6.0 mM DTT and Ac-DEVD-AFC (4.0 µg/ml). Reactions were allowed to proceed at room temperature. Fluorescence readings were taken at 15 min intervals for 1 h using a spectrofluorometer (excitation wavelength: 400 nm; emission wavelength: 505 nm).

Figure Legends

FIG. 1: TRIP-Br decoy peptides antagonize KRIP-1/TRIP-Br PHD-bromodomain interactions. (A) Autoradiogram of an immunoprecipitation (IP) assay demonstrating specific KRIP-1/TRIP-Br PHD-bromodomain interaction in vitro and blocking activity of the decoy peptides. GAL4-KRIP-1 was specifically immunoprecipitated by the agarose-conjugated anti-GAL4 antibody (Lanes 3-5 & 7–10) but not by the non-specific control anti-cyclin E antibody (Lane 6); (B) Antagonism of PHD-bromodomain interactions in vivo. U2OS cells were transiently transfected with 0.4 µg of the indicated GAL4 expression constructs and 1.2 µg of pMT3A/KRIP-1, along with 0.4 µg of the minimal luciferase reporter pG5-GL3 and 0.1 µg of the control reporter pCMV/β-gal. The transfected cells were exposed to either vehicle (0.5% DMSO) or 50 µM of the indicated decoy peptides prior to harvesting for sequential assay of luciferase and galactosidase activity. Fold activation refers to luciferase activity normalized to β-galactosidase activity, and is expressed relative to the activity observed with transfection of the reporter alone. Values represent the average +/− standard deviation of at least two independent experiments.

FIG. 2: Analysis of peptide uptake by U2OS cells. (A) Peptide internalization monitored by fluorescence microscopy. Figures depict internalization of FITC-labeled *SCR, *Br1 and *Br2 into U2OS cells at 24 h post-treatment; (B) Measurement of peptide internalization efficiency by flow cytometry. The percentage of FITC-positive cells was determined using the WinMDI software. Values represent the average +/− standard deviation of two independent experiments. The student t-test was used to compare values. P=0.454 for the simultaneous comparison of all peptide treatments.

FIG. 3: Analysis of E2F-responsive transcription in U2OS cells in response to decoy peptide treatment. (A) β-galactosidase/Luciferase assay of U2OS cells co-transfected with 0.1 µg of pCMV/β-galactosidase and 7.5 µg of the indicated luciferase reporter plasmids. Promoter activity of vehicle-treated samples was normalized to 100% and the activities of the peptide-treated samples were expressed relative to the vehicle-treated control. Values represent the average +/− standard deviation of at least two independent experiments; (B) Semi-quantitative RT-PCR analysis on total RNA for dhfr, cyclin-E, cyclin A2, PCNA, DNA Polα and cdc2 expression in U2OS cells exposed for 16 h to either vehicle (0.5% DMSO) or 50 µM of the indicated decoy peptides. H-actin was included as an internal control. Figure shows results obtained from two independent experiments.

Figure 4:
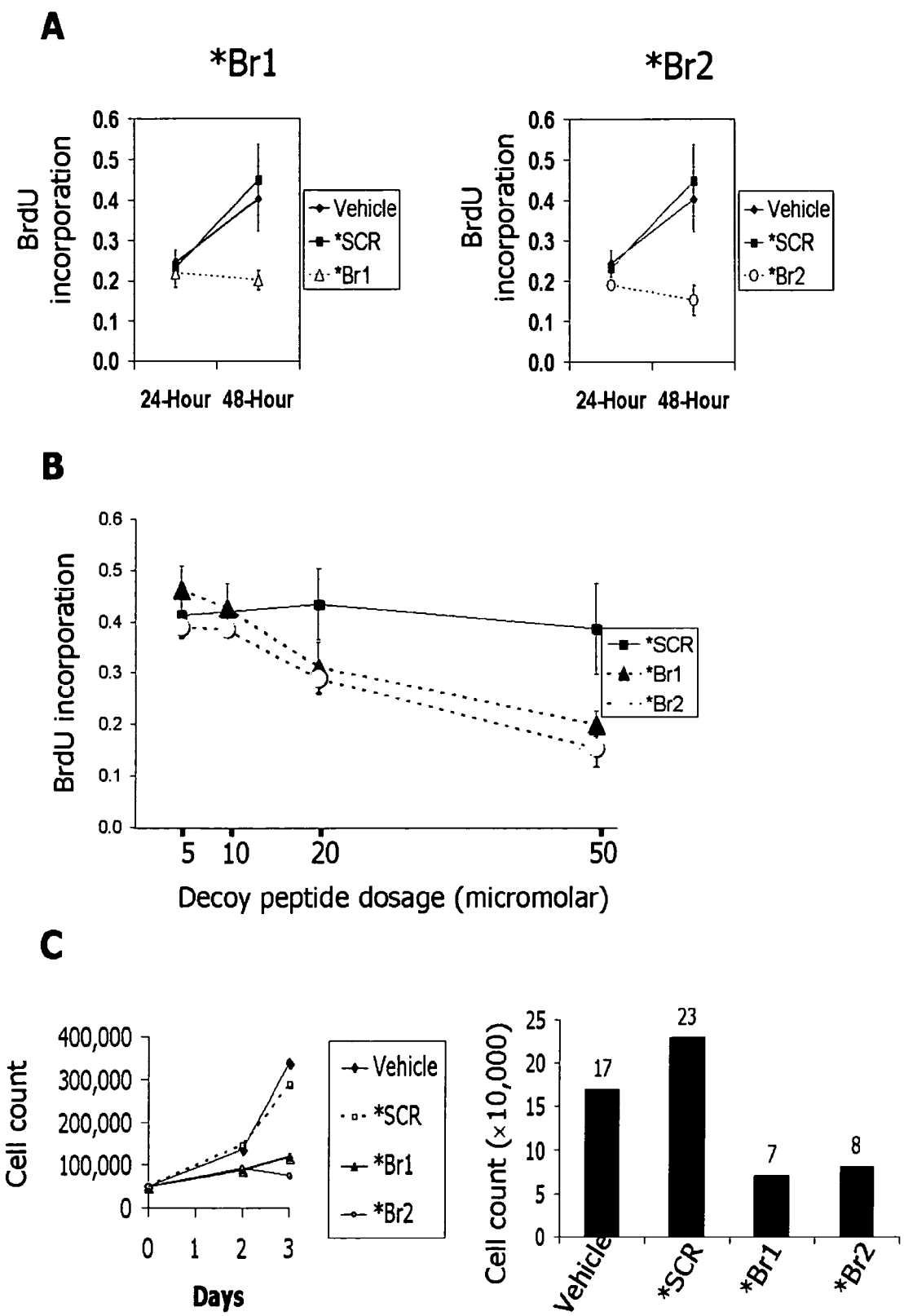
FIG. 4 is A: results of U2OS cells, exposed to decoy peptides for 24 or 48 h, assayed for BrdU incorporation with a colorimetric ELISA assay; B: results of U2OS cells, exposed to varying doses of decoy peptides, assayed for BrdU incorporation with a colorimetric ELISA assay; C: results of total cell number determination using a Coulter® cell counter and cell counts of cells stained with trypan blue.

FIG. 4: Time-dependent and dose-dependent anti-proliferative effects of the decoy peptides. (A) Time-dependent anti-proliferative effects of the decoy peptides. U2OS cells, exposed to either vehicle (0.5% DMSO) or 50 µM decoy peptides for either 24 or 48 h, were assayed for BrdU incorporation with a colorimetric ELISA assay. Values represent the average +/− standard deviation of two independent experiments; (B) Dose-dependent anti-proliferative effects of the decoy peptides. U2OS cells, exposed to 5, 10, 20 or 50 µM of *SCR (solid line and square), *Br1 (dashed line and triangle) or *Br2 (dashed line and circle) for 48 h, were assayed for BrdU incorporation with a colorimetric ELISA assay. Values represent the average +/− standard deviation of at least two independent experiments; (C) Cell proliferation analysis. Left panel: At 0, 48 and 72 h post decoy peptide treatment, total cell number was determined electronically using a Coulter® counter. Right panel: At 72 h post-treatment, cells were harvested and stained with trypan blue for viable cell count analysis.

Figure 5:
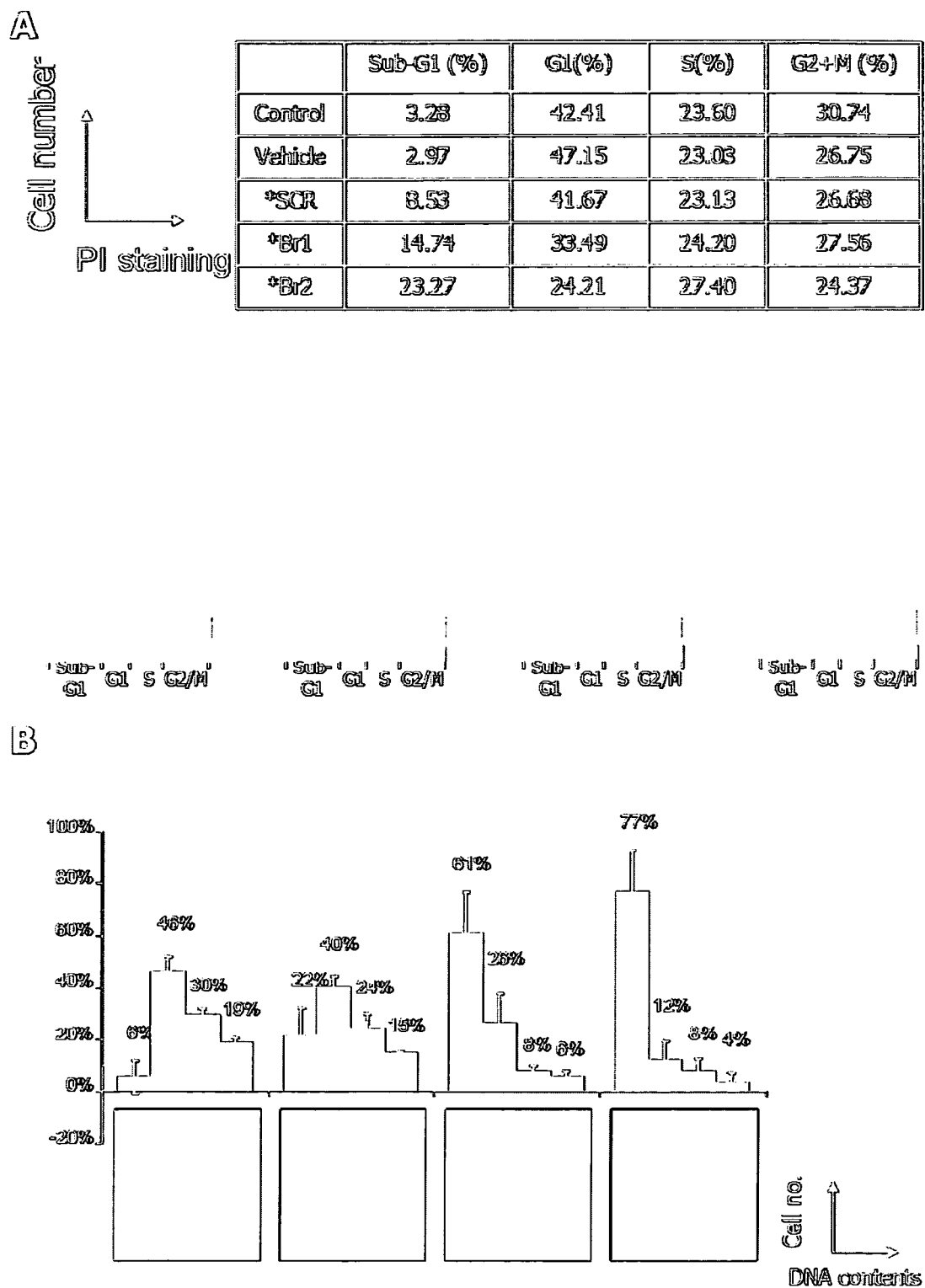
FIG. 5 is A: cell cycle distribution profile of asynchronous populations of U2OS cells exposed to either vehicle (DMSO) or the indicated decoy peptides at 24 h; B: a graphical representation of the cell cycle distribution profile at 72 h post-treatment.

FIG. 5: Flow cytometric analysis of asynchronous populations of U2OS cells at 24 and 72 h post-treatment with decoy peptides. (A) The cell cycle distribution profile of asynchronous populations of U2OS cells exposed to either vehicle (DMSO) or the indicated decoy peptides for 24 h. The cell cycle profile of each treated sample (shaded) was superimposed on that of the untreated control (not shaded) for visual comparison. Table shows the percentage of cells in various phases of the cell cycle; (B) Graphical representation of the cell cycle distribution profile at 72 h post-treatment. Values represent the average +/− standard deviation of two independent experiments.

FIG. 6: Caspase assay. (A) Caspase 3 protease activity in U2OS cells exposed to either Eto (Etoposide) for 24 h or 50 µM decoy peptides for 48 or 72 h, were assayed using the Ac-DEVD-AFC fluorogenic substrate. Histogram shows caspase-3 protease activity per µg of whole cell lysate input. Values represent the average +/− standard deviation of two independent experiments. Control: cells cultured in normal growth medium; Vehicle: cells cultured in the presence of 0.5% DMSO; (B) Western blot analysis of PARP cleavage. U2OS cells were exposed to either Eto (Etoposide) for 24 h or 50 µM decoy peptides for 72 h. Lane 1: Vehicle cells (cultured in the presence of 0.5% DMSO for 24 h); Lane 2: 25 µM Eto; Lane 3: 250 µM Eto; Lane 4: Vehicle (cells cultured in the presence of 0.5% DMSO for 72 h); Lane 5: *SCR; Lane 6: *Br1; Lane 7: *Br2.

FIG. 7: Cell cycle protein expression profile and protein decay analysis. (A) Protein expression profile of U2OS cells released from nocodazole arrest in the absence or presence of decoy peptide treatment. Protein expression of various cyclins and Cdks was assessed by Western blotting using whole cell lysates from synchronized U2OS cells at 4, 8, 12, 16, 20 and 24 h after release. Coomassie-stained proteins served as loading controls; (B) U2OS cells transfected with vector backbone (vehicle) or pRc/cyclin E and pCMV/Cdk2 (1 µg each), were arrested at the G2/M boundary by exposure to nocodazole (75 ng/ml) and then released to re-enter the cell cycle. Protein expression of cyclin E and Geminin was assessed using whole cell lysates from synchronized U2OS cells at 0, 4, 8, 12, 16 and 20 h after release; (C) Protein decay analysis of Geminin expression in the absence or presence of cyclin E/Cdk2 over-expression (left panel) or in the absence or presence of decoy peptide treatment (right panel) by Western blotting (WB). Coomassie stained proteins served as the loading control (C).

Figure 8:
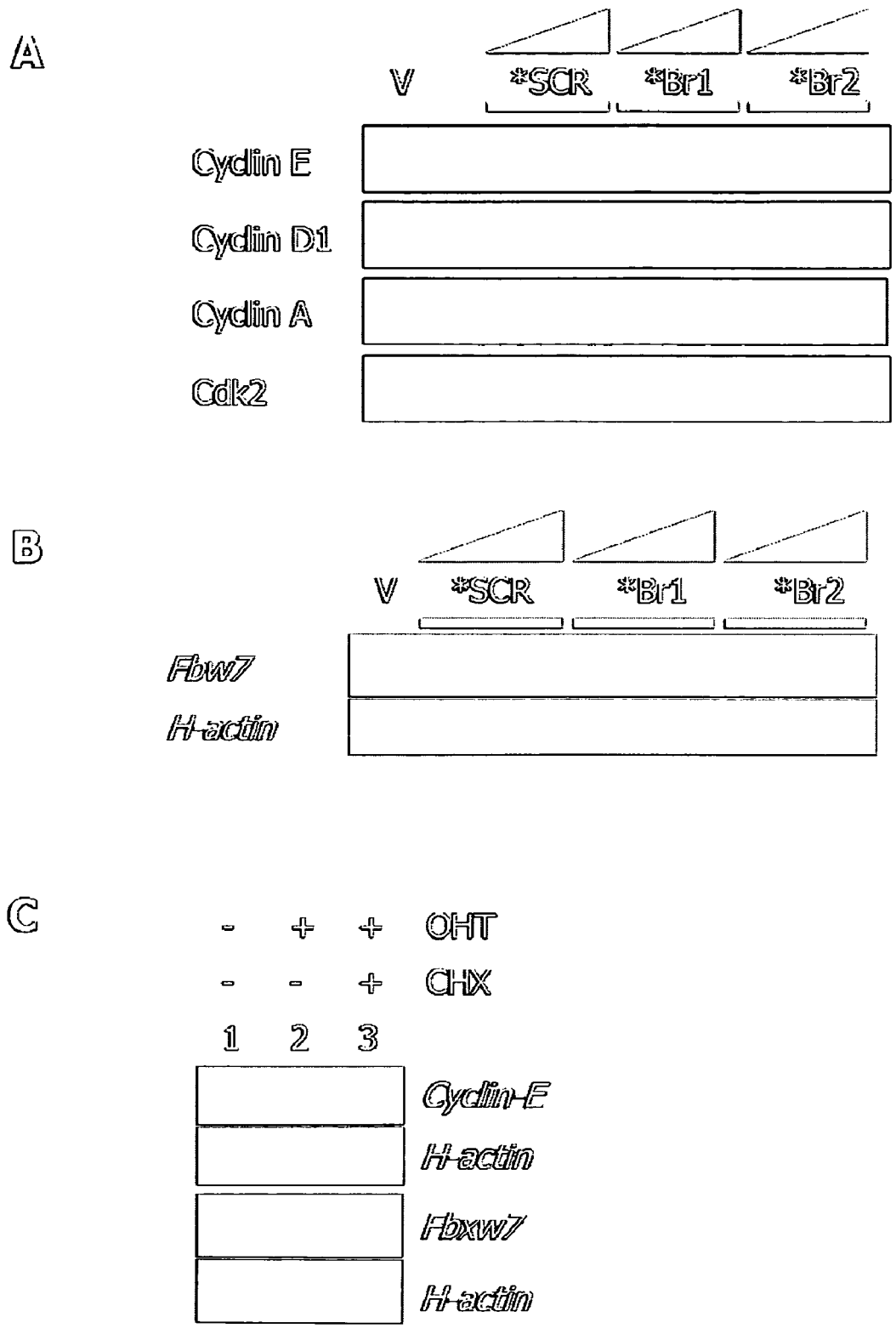
FIG. 8 is A: western blot analysis of expression of cyclins A, D and E in whole cell extracts derived from U2OS cells exposed to decoy peptides; B: semi-quantitative RT-PCR analysis of U2OS cells exposed to decoy peptides; C: semi-quantitative RT-PCR analysis of cyclin-E and Fbxw7 expression in sub-confluent U2OS ER-E2F-1 cells grown with or without OHT and/or cycloheximide (CHX)

FIG. 8: The role(s) of the TRIP-Br integrator function in cyclin E regulation. (A) Western blot analysis of the expression of cyclins A, D and E in whole cell extracts derived from U2OS cells exposed to 5, 10 or 20 µM of decoy peptides for 48 h. Cdk2 served as a loading control; (B) Dosage-dependent effects of decoy peptides on Fbxw7 expression. U2OS cells exposed to 5, 10 or 20 µM of decoy peptides were analyzed for Fbxw7 mRNA transcript levels by semi-quantitative RT-PCR. H-actin was co-amplified as an internal control; (C) cyclin-E and Fbxw7 expression was analyzed by semi-quantitative RT-PCR using total RNA from sub-confluent U2OS ER-E2F-1 cells grown with or without OHT and/or cycloheximide (CHX) for 2 h as indicated. H-actin was included as an internal control.

Figure 9:
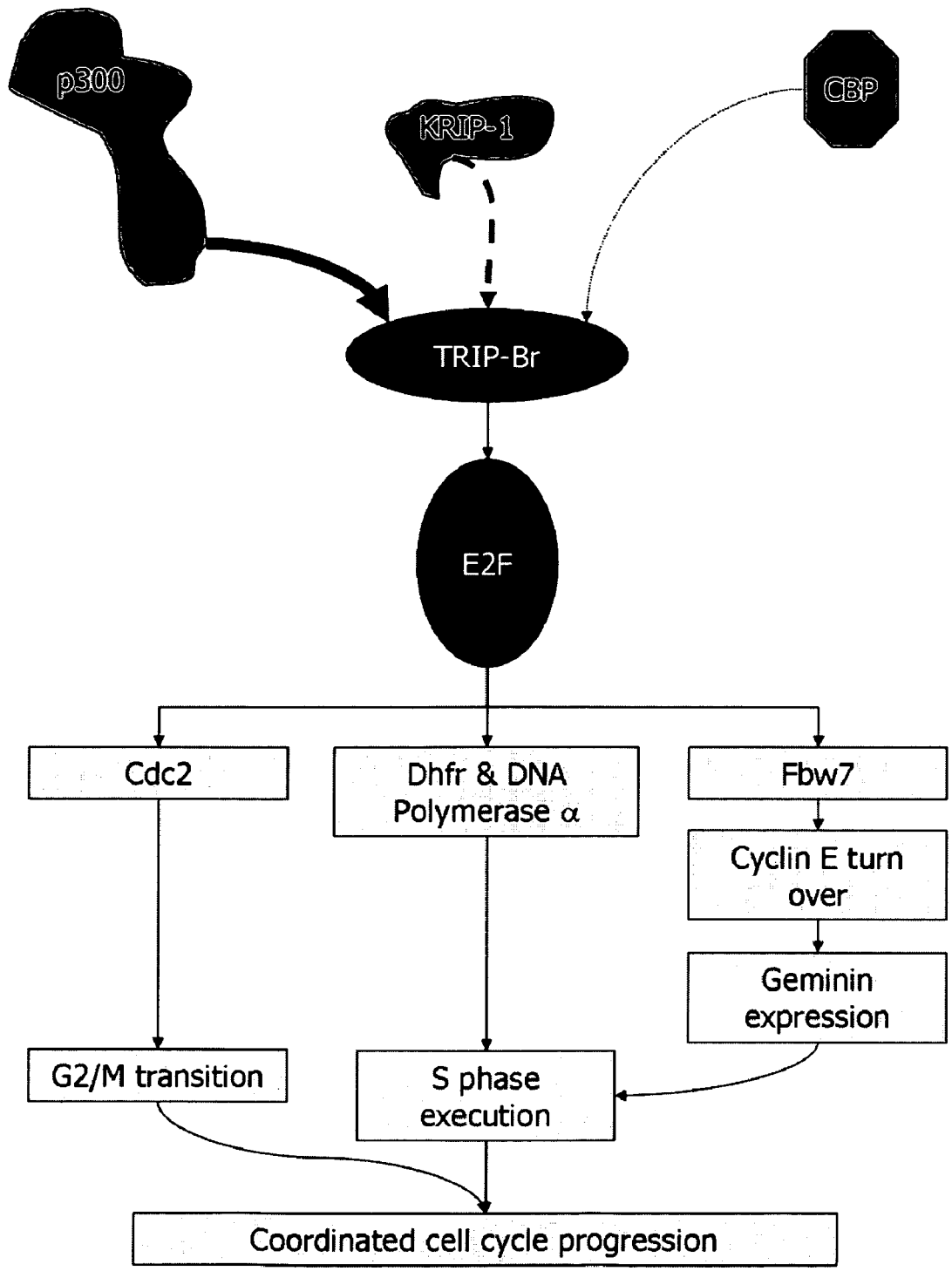
FIG. 9 is a schematic diagram depicting the role of TRIP-Br integrator function in E2F-dependent cell cycle progression.

FIG. 9: The role of TRIP-Br integrator function in E2F-dependent cell cycle progression. The TRIP-Br proteins are proposed to integrate and transduce regulatory signals conferred by various PHD-bromodomain proteins in a manner that contributes to E2F-dependent cell cycle progression.

Results

TRIP-Br decoy peptides antagonize KRIP-1/TRIP-Br PHD-bromodomain interactions in vitro and in vivo. Peptides corresponding to the PHD-bromodomain interacting regions of TRIP-Br1 (*Br1) and TRIP-Br2 (*Br2) (Hsu, S. I. H., et al. *EMBO J* 20, 2273-2285 (2001)), and a control "scrambled" (*SCR) peptide with the same amino acid composition of the *Br1 peptide (see Materials and Methods) were designed. The *SCR peptide sequence did not show significant homology to any known protein motifs, as determined by a motif-mining algorithm (http://www.motif-.genome.adjp/; data not shown). To facilitate translocation of the decoy peptides into cultured cells, the amino-terminus of each peptide was tagged with the 16 amino acid penetratin sequence derived from the third helix of the *Drosophila melanogaster* antennapedia homeodomain protein (Derossi, D., et al. *J. Biol. Chem.* 269, 10444-10450 (1994)). This membrane-translocating sequence has the demonstrated ability to internalize unrelated peptide sequences to which it is tagged (Bandera, L. R., et al. *Nature Biotech.* 15, 896-901 (1997)).

Our results indicate that the above peptides antagonize the TRIP-Br/KRIP-1 protein complex formation. Immunoprecipitation (IP) of in vitro translated (IVT) GAL4-KRIP-1 fusion protein using anti-GAL4 antibody led to co-IP of TRIP-Br1 or TRIP-Br2 IVT products (FIG. 1A, lanes 3 & 4). GAL4 alone did not lead to co-IP of TRIP-Br (FIG. 1A, lanes 1 & 2), and GAL4-KRIP-1 did not co-IP the control luciferase IVT product (FIG. 1A, lane 5). While addition of the control *SCR peptides to the IP binding reactions did not affect GAL4-KRIP-1/TRIP-Br complex formation (FIG. 1A, lanes 7 & 9), addition of *Br1 or *Br2 decoy peptides dramatically reduced the ability of GAL4-KRIP-1 to co-IP TRIP-Br1 or TRIP-Br2 (FIG. 1A, lanes 8 & 10). These observations demonstrate that *Br1 or *Br2 specifically block the ability of the TRIP-Br proteins to interact with the PHD-bromodomain of KRIP-1 in vitro.

Employing the previously described reporter system (Hsu, S. I. H., et al. *EMBO J.* 20, 2273-2285 (2001)) in U2OS cells, we observed that exposure of cells to either *Br1 or *Br2, but not *SCR, resulted in complete abolishment of the KRIP-1-associated co-activating function on GAL4-TRIP-Br transcriptional activity (FIG. 1B, compare lanes 4 & 5 with lane 3, and lanes 8 & 9 with lane 7). These observations demonstrate that *Br1 and *Br2 are capable of functionally antagonizing the PHD-bromodomain-interacting function of TRIP-Br proteins in vivo.

Direct fluorescence imaging showed that all three decoy peptides were efficiently internalized into U2OS cells (FIG. 2A). Flow cytometric analysis confirmed that there were no statistically significant differences in the efficiency with which the different peptides were internalized (FIG. 2B).

The PHD-bromodomain-interacting function of TRIP-Br proteins co-regulate E2F-dependent transcriptional activity in vivo. We used *Br1 and *Br2 to antagonize this function and alter the level of endogenous E2F/DP activity on an E2F-responsive reporter. U2OS cells were chosen for this assay because they express functional E2F-1, DP-1, Rb and detectable levels of endogenous TRIP-Br1 (as assessed by Western blot analysis using a rabbit polyclonal anti-TRIP-Br1 antibody (Hsu, S. I. H., et al. *EMBO J* 20, 2273-2285 (2001)); data not shown). U2OS cells transfected with an E2F-responsive luciferase reporter (pGL3-TATA-6xE2F-Luc) or a TATA-containing minimal luciferase reporter (pGL3-TATA-Luc) were exposed for 5 h to either vehicle (DMSO) or 50 µM of *SCR, *Br1 or *Br2, prior to harvesting for measurement of luciferase activity. Treatment with *Br1 or *Br2, but not *SCR, decreased the transcriptional activity of the E2F-responsive luciferase reporter (FIG. 3A, left panel). Treatment with *Br2 did not alter the transcriptional activity of the minimal reporter significantly, while treatment with *SCR and *Br1 was associated with slight activation (FIG. 3A, right panel). All three decoy peptides failed to influence the transcriptional activity of a luciferase reporter driven by an androgen-responsive but E2F-unresponsive human Prostate Specific Antigen (PSA) proximal promoter (data not shown). These results indicate that the observed transcriptional repression associated with exposure of cells to either *Br1 or *Br2, was specifically mediated through perturbation of TRIP-Br-containing protein complexes assembled at E2F binding sites.

Semi-quantitative RT-PCR analysis was performed to measure endogenous mRNA levels expressed by six representative E2F-regulated genes: cyclin-E (Ohtsubo, M., et al. *Mol Cell Biol* 15, 2612-2624 (1995)), cyclin A2 (Rosenblatt, J. et al. *Proc Natl Acad Sci USA* 89, 2824-2828 (1992); Roy, L. M., et al. *J. Cell Biol* 113, 507-514 (1991)), dhfr (Miller, G. P. and Benkovic, S. J. *Chem Biol* 5, 105-113 (1998)), *PCNA* (Warbrick, E. *Bioessays* 22, 997-1006 (2000)), *DNA Pol*α (Frick, D. N. and Richardson, C. C. *Annu Rev Biochem* 70, 39-80 (2001)) and cdc2 (Smits, V. A. and Medema, R. H. *Biochim Biophys Acta* 1519, 1-12 (2001)). These genes encode proteins that play key roles during distinct phases of the cell cycle. Exposure of cells to either *Br1 or *Br2 resulted in significant down regulation of the cdc2 gene, as reflected by the markedly reduced cdc2 mRNA transcript level (FIG. 3B). In contrast, the mRNA expression levels of DNA Polα and dhfr were down-regulated by exposure to *Br2, but not *Br1 (FIG. 3B). Transcriptional activity of the cyclin-E, cyclin A2 and PCNA genes was unaffected by exposure to either *Br1 or *Br2 (FIG. 3B). Relative to the vehicle-treated control, the scrambled peptide *SCR exerted negligible effects on the expression profile of the genes under investigation. Thus, decoy peptide-mediated antagonism of interactions between the TRIP-Br proteins and endogenous PHD zinc finger and/or bromodomain-containing factors, results in the differential down-regulation of the transcriptional activity of a subset of endogenous E2F-responsive genes in U2OS cells.

Antagonism of TRIP-Br integrator function elicits a proliferative block. The E2F transcription factors have been shown to play a crucial role in regulating cellular proliferation by integrating the activity of the cell cycle machinery with that of the transcriptional apparatus (Lam, E., et al. *Curr Opin Cell Biol* 6, 859–866 (1994)). Asynchronous U2OS cultures were exposed to either vehicle or decoy peptides (50 µM) for 24 and 48 h, and then assayed for proliferative potential by BrdU incorporation. Between 24 h and 48 h post-treatment, cultures exposed to *Br1 or *Br2 showed substantially reduced DNA synthesis activity (FIG. 4A). In contrast, cells treated with *SCR exhibited a basal DNA synthesis rate similar to that of the vehicle-treated control cells. U2OS cells exposed to increasing concentrations of *Br1 or *Br2, but not *SCR, exhibited a progressively reduced ability to incorporate BrdU (FIG. 4B), indicating that the inhibitory effects on DNA synthesis associated with exposure to the *Br1 or *Br2 decoy peptides were specific and dose-dependent. Consistent with the BrdU incorporation data, both vehicle- and *SCR-treated cultures exhibited nearly identical increments in cell number over time while *Br1- or *Br2-treated cultures exhibited nearly complete cessation of cell proliferation (FIG. 4C, left panel). Trypan blue dye exclusion manual cell count analysis demonstrated that U2OS cell cultures treated with either *Br1 or *Br2 for 72 h contained significantly fewer viable cells compared to the vehicle or the *SCR-treated controls (FIG. 4C, right panel). These phenotypes were reproducible, given that CNE2 (nasal pharyngeal carcinoma) and Caski (cervical carcinoma), two other cancer cell lines known to express TRIP-Br1 and TRIP-Br2, responded to *Br1 or *Br2 in manners similar to those exhibited by U2OS cells (data not shown).

The TRIP-Br decoy peptides induce accumulation of a sub-G1 population through a caspase-3-independent mechanism. We employed flow cytometry to examine the cell cycle profile of asynchronous populations of U2OS cells exposed to either vehicle, *SCR, *Br1 or *Br2 for 24 and 72 h. At 24 h post-treatment, cells exposed to *Br1 or *Br2 registered a 1.5 to 2.5-fold increase in sub-G1 (sub-diploid) populations compared to vehicle and *SCR-treated cells (FIG. 5A). The magnitude of sub-diploidization was even greater at 72 h post-treatment, with more than 70% of cells in *Br1- or *Br2-treated cultures exhibiting a sub-G1 complement of genomic DNA (FIG. 5B).

The induction of a sub-G1 cell population is frequently associated with endonucleolytic degradation of genomic DNA accompanying apoptosis. U2OS cells treated with either *SCR, *Br1 or *Br2 for 48 or 72 h were assayed for caspase-3 protease activity using a caspase-3-specific synthetic oligopeptide substrate (Ac-DEVD-AFC). The levels of caspase-3 protease activity in cell lysates prepared from vehicle, *SCR, *Br1 or *Br2-treated cultures were indistinguishable from the baseline activity detected in cell lysates prepared from untreated controls, as determined by spectrofluorometry (FIG. 6A). The failure to detect caspase-3 activity was not due to technical error, as cells treated with the apoptosis-inducing pharmacological agent etoposide (eto) showed a dose-dependent stimulation of caspase-3 activity several orders of magnitude above baseline (FIG. 6A). To confirm the results obtained in the caspase-3 assay, PARP (Poly[ADP-ribose]polymerase) cleavage studies (Patel, T., et al. *FASEB* 10, 587-597 (1996)) were performed in parallel (FIG. 6B). While exposure to Etoposide for 24 h resulted in PARP cleavage in a dose-dependent manner (FIG. 6B, lanes 1-3), *Br1 or *Br2 treatment was not associated with significant PARP cleavage as compared to the vehicle or the *SCR-treated control (FIG. 6B, lanes 4-7). The failure of *Br1 or *Br2 to stimulate caspase-3 activity and PARP cleavage strongly argues against the involvement of caspase-3 and hence, classical apoptosis, in the process of TRIP-Br decoy peptide-induced sub-diploidy.

Incomplete DNA replication: an alternative mechanism for sub-diploidization. For most eukaryotic cells, DNA replication takes place once per cell cycle to maintain genomic stability. This strict requirement is fulfilled by a finely tuned interplay between cyclins, Cdks and pre-replication complexes (pre-RCs) (Diffley, J. F. and Labib, K. *J. Cell Sci* 115, 869-872 (2002)). It has been demonstrated that deregulated expression of G1 phase cyclins may prevent pre-replication complex (pre-RC) formation and inhibit replication licensing in a manner that would reduce the number of functional replication origins (Tanaka, S. and Diffley, J. F. *Genes Dev* 16, 2639-2649 (2002)). In this context, subsequent replication from an insufficient number of functional origins would then lead to incomplete DNA synthesis and hence progressive loss of chromosomal DNA. Cells unable to complete DNA replication would generate daughter cells that fail to maintain a constant 2N ploidy, thus registering a sub-G1 peak in flow cytometry analyses.

To determine whether the decoy peptides exert the proposed genome-destabilizing effects through deregulation of G1 cyclin expression, we investigated the expression profile of key cyclin-Cdk complexes in response to decoy peptide treatment. Cell cycle synchronization of U2OS cells was achieved using nocodazole, which efficiently arrested more than 90% of cells at the G2/M boundary with a 4N complement of DNA content as assessed by flow cytometry analysis (data not shown). The cells were then released from nocodazole block in the presence of vehicle or one of the decoy peptides. At every 4 h interval after release, whole cell protein extracts were prepared. Western blot analysis showed that the cell cycle expression profile of endogenous cyclins A2 and D1, and the cyclin-dependent kinase Cdk2 was unaffected by decoy peptide treatment (FIG. 7A). In marked contrast, we observed a significant perturbation of the normal cell cycle-regulated kinetics and amplitude of cyclin E protein expression following exposure to either *Br1 or *Br2. In vehicle and *SCR-treated U2OS cells, cyclin E protein accumulated during mid-to-late G1 between 8 h and 16 h post-release (FIG. 7A). As cells progressed into S phase, the level of cyclin E proteins gradually declined due to ubiquitin-mediated proteolysis (Koepp, D. M., et al. *Cell* 97, 431-434 (1999)). *Br1 or *Br2-treated cells exhibited premature accumulation of cyclin E beginning in early G1 (as early as 4 h post-release) compared with vehicle or *SCR-treated cells. Furthermore, the absolute levels of cyclin E protein were dramatically up-regulated and sustained at high levels in the *Br1 or *Br2-treated cultures up to 24 h post-release. These observations indicate that the TRIP-Br "integrator" function plays a physiologically important role in preventing cyclin E protein accumulation during the cell cycle. Antagonizing this function using decoy peptides may influence the efficiency of DNA replication by upregulating the expression of cyclin E.

Cdks inhibit pre-RC formation and hence licensing of DNA replication by acting through a multitude of protein targets. One such target is the Anaphase Promoting Complex/Cyclosome (APC/C), an E3 ubiquitin ligase. APC/C has been shown to promote licensing in early G1 by accelerating the degradation of Geminin, a 25 kDa nuclear protein that inhibits DNA replication by preventing the incorporation of MCM proteins into pre-RC through its interaction with Cdt1 (Diffley, J. F. and Labib, K. *J. Cell Sci* 115, 869-872 (2002); Wohlschlegel, J. A., et al. *Science* 290, 2309-2312 (2000)). Geminin is highly expressed during S, G2 and M phases and is normally targeted for ubiquitin-mediated proteolysis by the APC/C at the metaphase-anaphase transition in order to permit DNA replication to occur in early G1 of the succeeding cell cycle (McGarry, T. J. and Kirschner, M. W. *Cell* 93, 1043-1053 (1998)). The APC/C-associated E3 ligase activity is switched on by cyclin B/Cdc2 during the mitotic phase, and turned off by G1 cyclin-associated Cdk activities. Therefore, deregulation of G1 cyclin expression in early G1 would inactivate APC/C, thereby allowing aberrant accumulation of Geminin and preventing assembly of pre-RC.

U2OS cells were first co-transfected with expression plasmids encoding human cyclin E and Cdk2 and then arrested at the G2/M boundary using nocodazole. Upon release, whole cell lysates were prepared from the synchronously cycling cells at 4-h intervals to assess Geminin expression by immunoblot analysis. Consistent with previous reports (McGarry, T. J. and Kirschner, M. W. *Cell* 93, 1043–1053 (1998)), Geminin was found to be expressed at high levels at the G2/M boundary and S phase in the mock-transfected (vehicle) control cells, but was undetectable during G1 phase (FIG. 7B). In contrast, the presence of overexpressed cyclin E/Cdk2 induced abnormal accumulation of Geminin during G1 phase (FIG. 7B). These data suggest that deregulated cyclin E/Cdk2 expression induces abnormal Geminin protein accumulation.

Protein decay analysis was performed on Geminin. Control (vehicle) or cyclin E/Cdk2 over-expressing cells were exposed to the protein synthesis inhibitor cycloheximide (CHX), and then whole cell lysates were prepared from the treated cells at 1-h intervals up to 5 h to assess endogenous Geminin levels by immunoblot analysis. In control cells, the Geminin level remained high until 3 h post-CHX treatment, after which the level declined sharply (FIG. 7C, left panel). In marked contrast, the Geminin level in cyclin E/Cdk2-expressing cells remained persistently high up to 5-h post-CHX treatment (FIG. 7C, left panel). Taken together, these results indicate that deregulated cyclin E/Cdk2 expression leads to stabilization of Geminin.

U2OS cells were exposed to vehicle or decoy peptides followed by CHX for protein decay analysis as described earlier. Both vehicle or *SCR-treated cells exibited similar kinetics of Geminin protein decay (FIG. 7C, right panel). In marked contrast, Geminin in *Br1 or *Br2-treated cells exhibited a significantly slower decay rate and steady state levels that remained persistently high at 5-h post-CHX treatment (FIG. 7C, right panel). These data are consistent with a model in which TRIP-Br decoy peptides induce sub-diploidy by suppressing DNA replication licensing through a mechanism involving cyclin E deregulation and Geminin stabilization.

TRIP-Br decoy peptides down-regulate Fbxw7 transcript levels. The observed cyclin E deregulation does not appear to arise from altered cyclin E transcript levels (FIG. 3B). The specific and timely (periodic) cell cycle-dependent expression pattern of cyclin E is principally regulated by the SCF-type ubiquitin ligase complex, which targets cyclin E for proteosome-mediated proteolysis (Koepp, D. M., et al. *Cell* 97, 431-434 (1999)). Thus, the observed up-regulation of cyclin E protein levels in *Br1- or *Br2-treated cells may be due to decoy peptide-induced alteration in the above ubiquitin-proteosome pathway. Since *Br1 or *Br2 treatment induced dose-dependent accumulation of cyclin E protein without affecting the protein levels of cyclin D1 and cyclin A2, two proteins known to be regulated by ubiquitin-mediated proteolysis (FIG. 8A, upper panel), we reasoned that the decoy peptides altered the expression and/or activity of one or more cyclin E-specific ubiquitin ligases (E3 enzymes). We performed semi-quantitative RT-PCR to measure Fbxw7 mRNA transcript levels in decoy peptide-treated cells. The Fbxw7 gene product, FBW7, which is the F-box protein component of the SCF complex responsible for target protein specificity, has been recently identified as an important physiologic regulator of cyclin E abundance (Koepp, D. M., et al. *Science* 294, 177 (2001)). *Br1 or *Br2, but not *SCR, down-regulated the expression level of Fbxw7 in a dose-dependent fashion (FIG. 8B). Failure to maintain normal expression levels of FBW7 protein would be predicted to abrogate the ability of the SCF$^{FBW7}$ complex to specifically poly-ubiquitinate cyclin E. These results suggest that TRIP-Br decoy peptide-mediated antagonism leads to the deregulated accumulation of cyclin E during the cell cycle, by a mechanism involving the down-regulation of Fbxw7 mRNA expression.

Fbxw7 is a novel E2F-responsive gene. In silico analysis revealed the presence of several cis-acting elements within the Fbxw7 promoter region that exhibit significant homology to the consensus E2F response element. Therefore, *Br1 or *Br2 treatment may conceivably cause direct or indirect inhibition of E2F-dependent Fbxw7 gene transcription. We next employed U2OS cells that stably express a chimaeric protein of the estrogen receptor (ER) fused to the E2F-1 transcription factor. It has been previously documented that the ER-E2F-1 fusion protein is expressed at relatively low levels as an inactive cytoplasmic protein (Lomazzi, M., et al. Nat Gen 31, 190-194 (2002)). Upon addition of the estrogen analogue 4-hydroxytamoxifen (OHT), ER-E2F-1 translocates into the nucleus and transactivates E2F-responsive promoters (Lomazzi, M., et al. Nat Gen 31, 190-194 (2002)). We confirmed that ER-E2F-1 was activated after the addition of OHT by examining the expression of cyclin-E, a known E2F target gene. Our RT-PCR analyses showed that activation of ER-E2F-1 led to robust induction of cyclin-E (FIG. 8C). Much like cyclin-E, activation of ER-E2F-1 also led to an increase in the expression of Fbxw7 even in the presence of the protein synthesis inhibitor cycloheximide (FIG. 8C). The demonstration that ER-E2F-1 mediated transcription of a putative E2F-responsive gene occurs in the absence of de novo synthesis of an intermediate factor allows us to conclude that Fbxw7 is a direct target of E2F-1.

Example 2

Use of DNA Enzymes to Disrupt TRIP-Br Function

Materials and Methods

Plasmid DNA and cDNA clones. The pRcSV/cyclin E and pCMV/Cdk2 were kind gifts from Dr. Steve Reed (The Scripps Research Institute, USA). The other plasmid DNA and cDNA clones for transfection experiments have been previously described (Hsu, S. I. H., et al. *EMBO J* 20, 2273-2285 (20001)).

Biochemical reagents. Polyclonal antibodies for cyclin D1 (sc-718), cyclin E (sc-481), Cdk4 (sc-601) and $p27^{KIP1}$ (sc-528), and HRP-conjugated anti-rabbit (sc-2004) and anti-mouse (sc-2005) secondary antibodies were purchased from Santa Cruz Biotechnology.

Synthetic oligonucleotides. DNA enzymes were synthesized commercially (GENSET SA, Paris) with an inverted thymidine at the 3' position. The following three DNA enzymes were synthesized:

```
E-Br2
                                         SEQ ID NO.:6
5'-T TAC CCA ACA GGC TAG CTA CAA CGA ATA TCA CA-3'

E-Br1
                                         SEQ ID NO.:7
5'-T TGC TCA GCA GGC TAG CTA CAA CGA CTT GCT CA-3'

E-SCR
                                         SEQ ID NO.:9
5'-C AGC TAC TGT GGC TAG CTA CAA CGA CCT GTC AT-3'
```

The residues corresponding to the catalytic core of each DNA enzyme are underlined.

Tissue culture cell lines. The human lung fibroblasts WI-38 were purchased from American Tissue Culture Collection (ATCC), maintained in 75 cm V/C tissue culture flasks (Nunc™) at 37° C. in a humidified atmosphere of 5% carbon dioxide ($CO_2$) and grown in Dulbecco's modified Eagle's medium (DMEM) (Sigma) supplemented with 10% characterized fetal bovine serum (FBS) (Hyclone®) and anti-microbial agents (50 IU/ml penicillin, 50 μg/ml streptomycin and 50 μg/ml gentamycin). For sub-culturing in various plate formats (Nunc™), cells were seeded consistently at $5 \times 10^4$ cells/10 $cm^2$. Cells used for experiments were between passages 3-10.

DNA enzyme transfection. WI-38 cells were rendered quiescent by cultivation in serum-free medium for 72 h before being transfected with DNA enzyme (0.1 μM) using Superfect as reported previously (Santiago, F. S., et al. *Nat Med* 5, 1264-1269 (1999)) in accordance to manufacturer's recommendations (Qiagen).

Cell proliferation assays. For the BrdU incorporation assays, growth-quiescent WI-38 cells in 96-well dishes were transfected with DNA enzyme and/or 100 ng of pCMV/E2F1, pCMV/DP1, pRSV/Cyclin E, or pCMV/Cdk2 and then exposed to Bromodeoxyuridine (BrdU, 100 μM) in the presence or absence of 10% FBS for 20 h. Bromodeoxyuridine (BrdU) incorporation was monitored with a calorimetric ELISA assay using a cell proliferation kit according to manufacturer's recommendations (Boehringer Mannheim). For manual cell count, growth-quiescent WI-38 cells in 24-well dishes were transfected with DNA enzyme and then exposed to 10% FBS for 72 h. The cells were rinsed with PBS, pH 7.4, and trypsinized, and 10 μl of cell suspension was taken from each sample and mixed with equal volume of trypan blue stain (Sigma, 0.4% w/v in 1×PBS). The number of unstained cells was enumerated manually using a hemocytometer. For colony formation assays, growth-quiescent WI-38 cells in 12-well dishes were transfected with DNA enzyme and then exposed to 10% FBS for 120 h. Cells were stained in situ with crystal violet (0.75% w/v hexamethyl-p-rosaniline chloride [SIGMA], 50% ethanol, 1.75% w/v paraformaldehyde, 0.25% w/v NaCl) for 10 min, and then rinsed thoroughly with deionized water to remove excess stains.

Semi-quantitative RT-PCR. Following various treatments, WI-38 cells in 6-well culture dish were subjected to total RNA extraction using the TRIZOL® Reagent (Life Technologies). Total RNA (4 μg) was reversed transcribed using oligo-dT and M-MLV reverse transcriptase in a total reaction volume of 20 μl. Polymerase Chain Reactions (PCR) were carried out on 3 μl cDNA sample in the presence of 25 mM deoxyribonucleotide triphosphates (dNTPs) and 40 μM of specific primer pairs in a total reaction volume of 50 μl. The cycling profile for PCR was as follow: 30 cycles of denaturation (94° C., 30 sec), annealing (51° C., 30 sec) and extension (72° C., 2 min), with a 2-minute initial denaturation step at 94° C. and a 10-minute polishing step at 72° C. at the end. Sequences of gene-specific primers are available upon request. Post-PCR samples were analyzed by agarose gel electrophoresis.

Western blotting analysis. Cells in 6-well culture dish were washed in cold PBS and lysed in sample buffer (50 mM Tris-Cl, pH 6.8, 2% SDS, 10% glycerol, 0.1% bromophenol blue and 100 mM DTT). Whole cell lysates were heated at 100° C. for 10 minutes prior to electrophoresis. Separation of complex protein mixtures was achieved using a discontinuous polyacrylamide gel electrophoresis system consisting of a stacking gel and a 10% separating gel. Electrophoresis was performed with 1× running buffer (25 mM Tris pH 8.6, 0.19 M glycine, 0.1% SDS) in a mini vertical electrophoresis apparatus (BIO-RAD) at constant voltage (80 V). Separated proteins were transferred to nitrocellulose membrane (Immobilon™-P, Millipore) by electro-blotting (30V overnight at 4° C.) in transfer buffer (50 mM Tris, 384 mM glycine, 20% methanol, 0.01% SDS). Following blocking (1×PBS, 0.5% Tween 20, 4% [w/v] non-fat milk), target proteins were detected using a 1:2,500 dilution of specific primary antibodies. Anti-mouse or anti-rabbit IgG antibodies conjugated with horseradish peroxidase (Santa Cruz) were used to visualize immunoreactive proteins at 1:2,500 dilutions using enhanced chemiluminescence (Pierce).

Figure Legends

FIG. 10: (A) Post-transcriptional suppression of gene expression by DNA enzymes. The DNA enzyme binds to a target mRNA by complementary base-pairing through the hybridizing arms. This positions the DNA enzyme catalytic core in proximity to the translation start site of the mRNA to facilitate phosphodiester bond cleavage between the A and the U residues of the start codon. Upon cleavage, the resulting mRNA fragments cannot support productive translation, and hence no polypeptide is synthesized. The DNA enzyme releases the cleaved products and goes on to cleave other mRNA substrates. (B) DNA enzymes targeting TRIP-Br transcripts. The two 10-nucleotide hybridizing arms flanking the 15-nucleotide catalytic domain of E-Br1 or E-Br2 DNA enzyme were designed to selectively bind to hTRIP-Br1 or hTRIP-Br2 mRNA, respectively, in a manner that would facilitate cleavage of the phosphodiester bond between the A and the U residues of the "AUG" start codon. As a control, the nucleotide sequence in each arm of E-Br1 was scrambled to produce the DNA enzyme E-SCR with an intact catalytic domain flanked by hybridization arms consisting of random sequences. In order to confer resistance to 3'-to-5' exonuclease digestion, the 3'-terminus of each DNA enzyme was capped with an inverted 3'-3'-linked thymidine.

Figure 11:
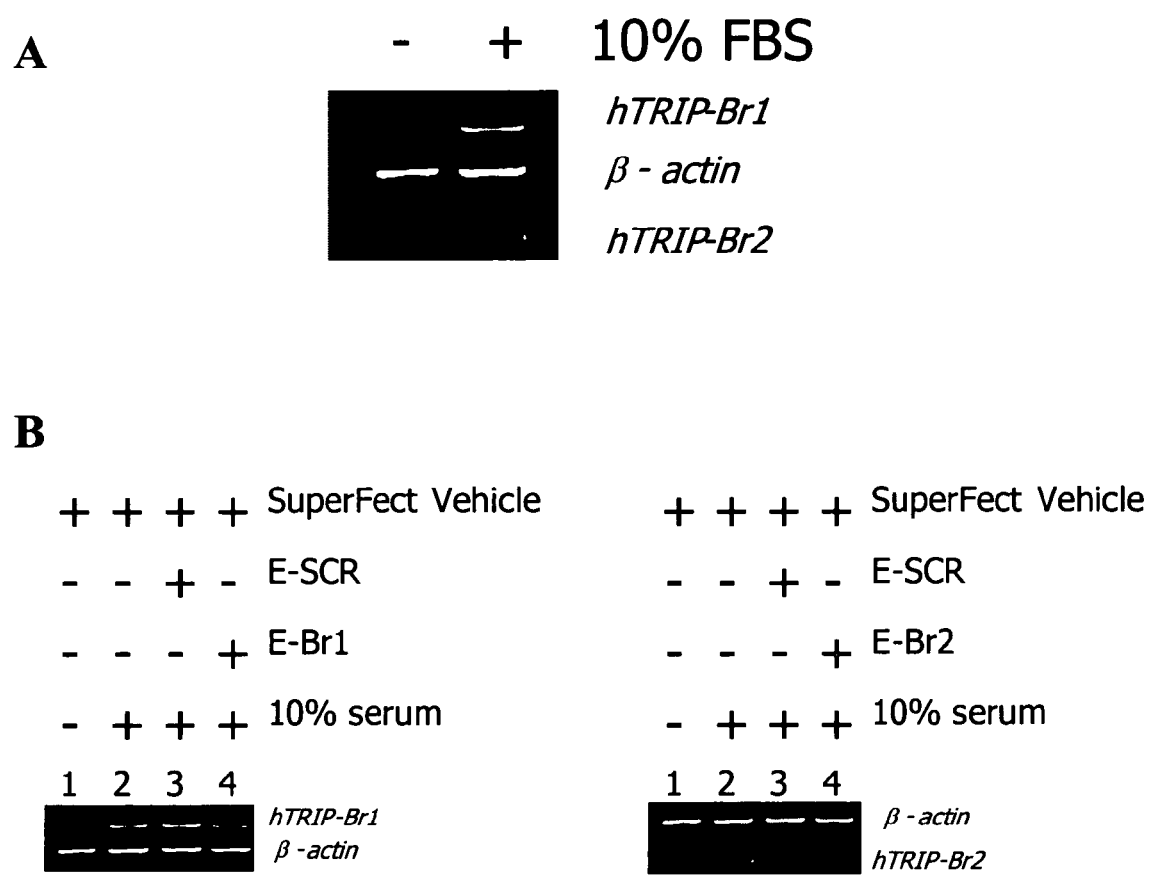
FIG. 11 is A: semi-quantitative RT-PCR analysis performed on sub-confluent WI-38 cells serum-starved for 72 h; B: semi-quantitative RT-PCR analysis performed on sub-confluent WI-38 cells serum-starved for 72 h and then transfected with the indicated DNA enzymes.

FIG. 11: (A) hTRIP-Br1 and hTRIP-Br2 expression is serum-inducible. Sub-confluent WI-38 cells were serum-starved for 72 h. At 24 h post-serum re-stimulation, semi-quantitative RT-PCR analysis was performed on total RNA to assess hTRIP-Br1 and hTRIP-Br2 expression. β-actin was included as an internal control. PCR products were resolved by agarose gel electrophoresis and ethidium bromide-stained DNA bands were visualized under UV.(B) E-Br1 and E-Br2 down-regulate TRIP-Br1 and hTRIP-Br2 expression respectively. Sub-confluent WI-38 cells were serum-starved for 72 h and then transfected with 0.1 µM of the indicated DNA enzymes. Semi-quantitative RT-PCR analysis was performed on total RNA to assess hTRIP-Br1 and hTRIP-Br2 expression. β-actin was included as an internal control. PCR products were resolved by agarose gel electrophoresis and ethidium bromide-stained DNA bands were visualized under UV.

FIG. 12: (A) E-Br1 or E-Br2 inhibits cell proliferation. Sub-confluent WI-38 cells were serum-starved for 72 h. Following DNA enzyme transfection, the cultures were re-stimulated with serum and allowed to proliferate. After 72 h, cells were harvested for viable cell count analysis. 10 µl of cell suspension from each sample was mixed with equal volume of 0.4% trypan blue stain. The number of unstained cells was enumerated manually using a hemocytometer. Data represent the average of at least two independent experiments. Student's t-test indicated that cell count associated with E-Br1 or E-Br2 treatment was significantly lower (P<0.05) compared to that associated with E-SCR treatment (P=3.25E-02 for E-Br1 versus E-SCR treatment, and P=1.44E-02 for E-Br2 versus E-SCR treatment). (B) E-Br1 or E-Br2 suppresses colony formation. Sub-confluent WI-38 cells were serum-starved for 72 h. Following DNA enzyme transfection, the cultures were re-stimulated with serum and allowed to proliferate. After 72 h, cells were stained in situ with crystal violet.

Figure 13:
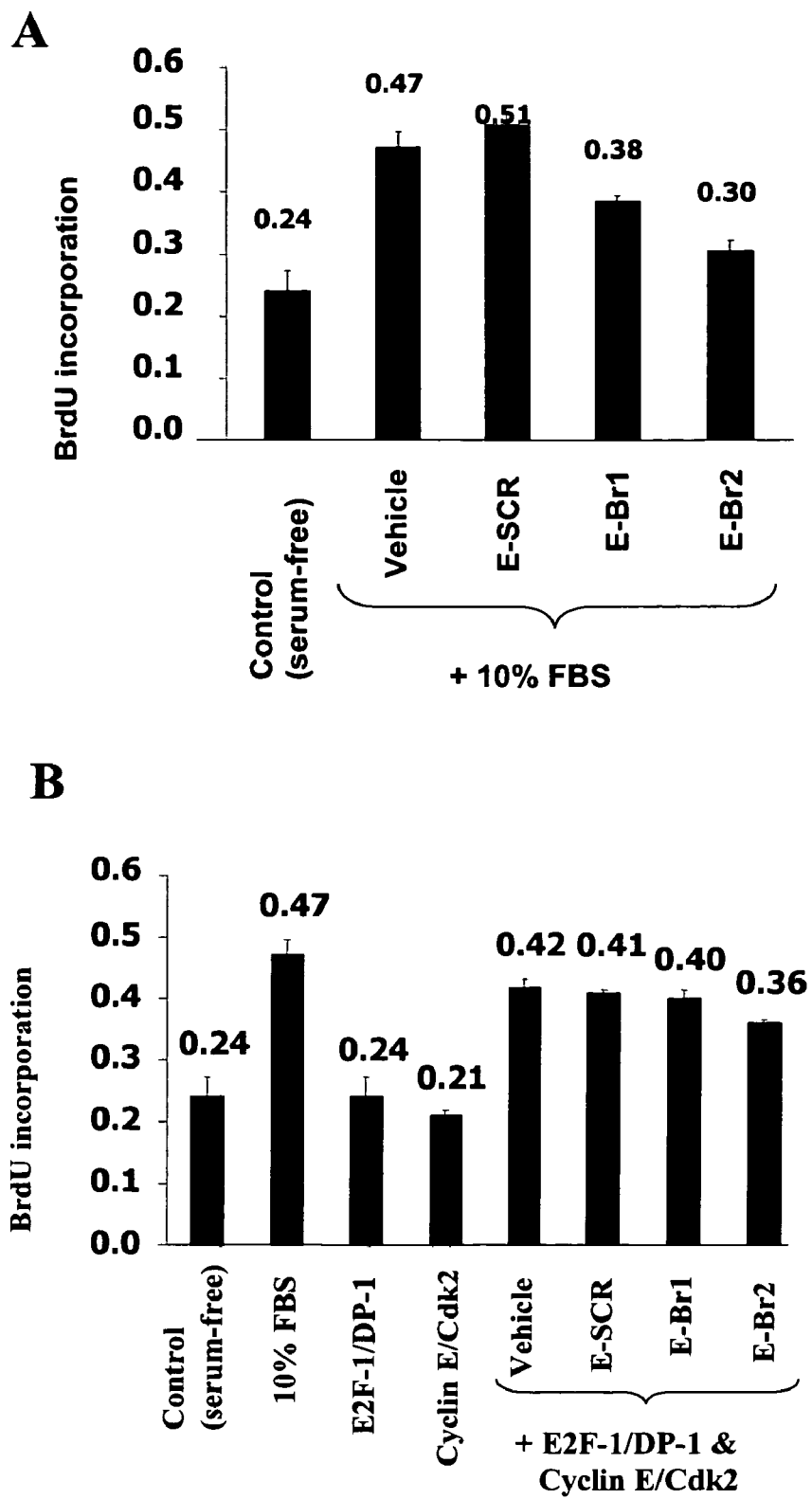
FIG. 13 is graphs of BrdU incorporation assayed by colorimetric ELISA assay in A: sub-confluent WI-38 cells serum-starved for 72 h, transfected with DNA enzyme and re-stimulated with serum; B: sub-confluent WI-38 cells serum-starved for 72 h and transfected with DNA enzyme and the expression plasmids encoding the indicated cell cycle regulators.

FIG. 13: (A) E-Br1 or E-Br2 suppresses serum-inducible S phase entry. Sub-confluent WI-38 cells were serum-starved for 72 h. Following DNA enzyme transfection, the cultures were re-stimulated with serum and allowed to proliferate in BrdU labeling medium. After 20 h, cells were assayed for BrdU incorporation with a colorimetric ELISA assay. Values represent the average of at least two independent experiments. Student's t-test indicated that BrdU incorporation associated with E-Br1 or E-Br2 treatment was significantly lower (P<0.05) compared to that associated with E-SCR treatment (P=1.29E-03 for E-Br1 versus E-SCR treatment, and P=8.47E-05 for E-Br2 versus E-SCR treatment). (B) E-Br1 or E-Br2 does not influence E2F1/DP1- and/or cyclin E/Cdk2-induced S phase entry. Sub-confluent WI-38 cells were serum-starved for 72 h. Following transfection with DNA enzyme and the expression plasmids encoding the indicated cell cycle regulators, the cultures were allowed to proliferate in BrdU labeling medium. After 20 h, cells were assayed for BrdU incorporation with a colorimetric ELISA assay. Values represent the average of at least two independent experiments.

Figure 14:
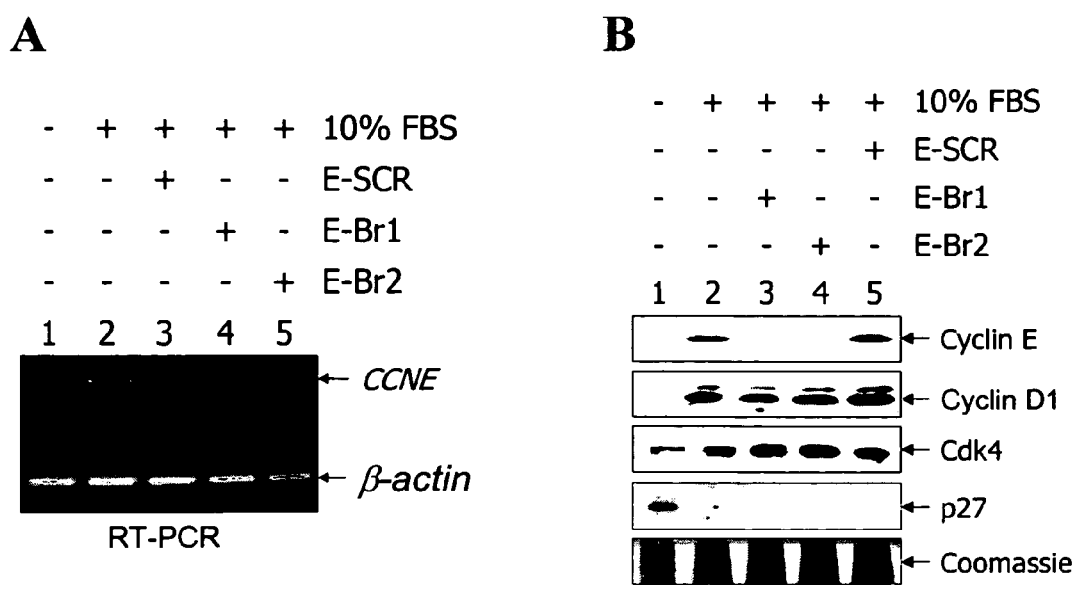
FIG. 14 is A: semi-quantitative RT-PCR analysis to assess CCNE expression in sub-confluent WI-38 cells serum-starved for 72 h, transfected with DNA enzymes and re-stimulated with serum; B: western blot (WB) analysis of cyclin E, Cdk4, cyclin D1 and p27$^{KIP1}$ expression in sub-confluent WI-38 cells serum-starved for 72 h.

FIG. 14: (A) E-Br1 or E-Br2 attenuates mitogen-stimulated CCNE gene induction. Sub-confluent WI-38 cells were serum-starved for 72 h. Following DNA enzyme transfection, the cultures were re-stimulated with serum and allowed to proliferate. After 20 h, cells were harvested and total RNA extracted for semi-quantitative RT-PCR to assess CCNE expression. β-actin was included as an internal control. PCR products were resolved by agarose gel electrophoresis and ethidium bromide-stained DNA bands were visualized under UV. (B) E-Br1 or E-Br2 prevents mitogen-induced cyclin E expression without altering the expression of Cdk4, cyclin D1 and p27$^{KIP1}$. Sub-confluent WI-38 cells were serum-starved for 72 h. Following transfection with DNA enzyme, the cultures were allowed to proliferate. After 20 h, cells were harvested for western blot (WB) analysis of cyclin E, Cdk4, cyclin D1 and p27$^{KIP1}$ expression. Coomassie-stained protein was included as control for normalization.

FIG. 15: (A) TRIP-Br2$^{-/-}$ PMEFs show significantly reduced BrdU incorporation in comparison to TRIP-Br2$^{+/+}$ PMEFs. Sub-confluent PMEF cultures (TRIP-Br2$^{+/+}$ and $^{-/-}$) were grown in BrdU labeling medium. After 20 h, cells were assayed for BrdU incorporation with a colorimetric ELISA assay. Values represent the average of at least two independent experiments. (B) TRIP-Br2$^{-/-}$ PMEFs show significantly lower rate of serum-induced proliferation in comparison to that of TRIP-Br2$^{+/+}$ PMEFs. Sub-confluent PMEFs were serum-starved for 72 h and then re-stimulated with serum. After 72 h, cells were harvested for viable cell count analysis. 10 µl of cell suspension from each sample was mixed with equal volume of 0.4% trypan blue stain. The number of unstained cells was enumerated manually using a hemocytometer. Data represent the average of at least two independent experiments. (C) TRIP-Br2 inactivation leads to CCNE gene down-regulation. Total RNA from wild-type (+) or TRIP-Br2 null (−) PMEFs was extracted for semi-quantitative RT-PCR to assess CCNE expression. β-actin was included as an internal control. PCR products were resolved by agarose gel electrophoresis and ethidium bromide-stained DNA bands were visualized under U.

Figure 16:
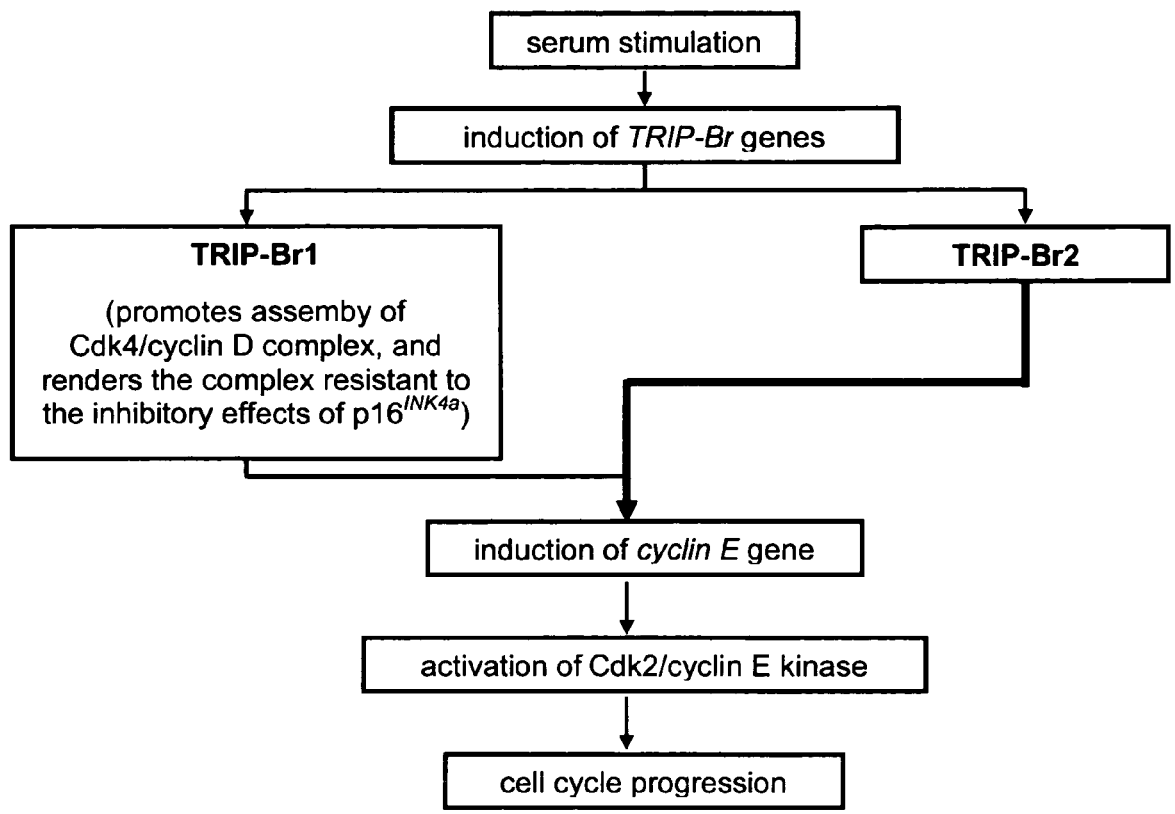
FIG. 16 is a schematic diagram of regulation of serum-inducible cell cycle progression by TRIP-Br.

FIG. 16: Flow chart showing regulation of serum-inducible cell cycle progression by TRIP-Br.

Results

E-Br1 or E-Br2 DNA enzymes specifically "knock down" serum-induced hTRIP-Br1 or hTRIP-Br2 gene expression.

DNA enzymes were employed to knock down the expression of endogenous human TRIP-Br1 or TRIP-Br2 mRNA transcripts in WI-38 human diploid fibroblasts. The mechanism by which DNA enzymes achieve post-transcriptional suppression of gene expression or gene "knock down" is illustrated in FIG. 10A. Two DNA enzymes (E-Br1 and E-Br2) were designed to target specifically the translational start site AUG in the messenger RNA of human TRIP-Br1 or TRIP-Br2 respectively (FIG. 10B).

WI-38 fibroblasts were rendered quiescent 72 h after serum withdrawal. During the resting stage, the quiescent fibroblasts expressed undetectable levels of hTRIP-Br1 and hTRIP-Br2 transcripts. Upon serum induction, the steady state levels of both hTRIP-Br1 and hTRIP-Br2 mRNA in stimulated WI-38 cells were significantly elevated (FIG. 11A), suggesting that expression of the TRIP-Br genes is serum-responsive.

To evaluate the effect of E-Br1 or E-Br2 on endogenous hTRIP-Br1 or hTRIP-Br2 mRNA, growth-quiescent WI-38 fibroblasts were pre-exposed to DNA enzymes for 24 h and then stimulated to re-enter the cell cycle with 10% FBS. At 16 h post-stimulation, total RNA was harvested and semi-quantitative RT-PCR was performed to measure the levels of intact TRIP-Br transcripts. To distinguish between intact and cleaved transcripts, RT-PCR was performed using gene-specific primer pairs that base-pair with target sequences flanking the DNA enzyme cut site, such that only intact transcripts are preferentially amplified. Results showed that 0.1 µM E-Br1 or E-Br2 efficiently down-regulated serum-inducible steady-state hTRIP-Br1 or hTRIP-Br2 mRNA levels respectively, whereas E-SCR had no effect (FIG. 11B). These findings demonstrate the ability of the E-Br DNA enzymes to knock down serum induction of hTRIP-Br gene transcription in a sequence-specific manner.

E-Br inhibits serum-induced WI-38 cell proliferation. To determine if inhibition of TRIP-Br gene expression during serum induction affects serum-stimulated cell cycle progression, growth-quiescent WI-38 cells were transfected with E-SCR, E-Br1 or E-Br2, followed by incubation with medium containing 10% FBS to stimulate cells to re-enter the cell cycle. At 72 h post-stimulation, cell numbers were assessed by trypan blue exclusion manual cell count. E-Br1 or E-Br2, at a concentration of 0.1 µM, was capable of inhibiting the serum-induced proliferative potential of WI-38 fibroblasts by 50-60%. In contrast, E-SCR at the same concentration had no significant effects on WI-38 growth as compared to vehicle-treated cells (FIG. 12A). To visually evaluate the anti-proliferative effects imposed by the DNA enzymes, WI-38 cells were induced with serum in the presence or absence of DNA enzymes. 72 h thereafter, the cells were stained with crystal violet. Consistent with the above findings, E-Br1 or E-Br2-treated cultures exhibited significantly reduced colony forming potential (FIG. 12B). Again, cells treated with E-SCR exhibited a colony forming potential similar to the normal and the vehicle-treated controls. Taken together, these results demonstrate that the knock down of TRIP-Br gene expression leads to attenuation of serum-inducible WI-38 cell proliferation.

E-Br DNA enzymes prevent serum-induced S phase entry. Serum-starved WI-38 cells were stimulated with serum in the presence of 0.1 µM DNA enzymes and their entry into S-phase was measured by BrdU incorporation. Compared to unstimulated cells, the vehicle- or the E-SCR-treated cultures incorporated approximately twice as much BrdU (FIG. 13A). In contrast, cells treated with E-Br1 or E-Br2 were significantly inhibited in their ability to incorporate BrdU. These data suggest that the knock down of TRIP-Br gene expression is sufficient to block serum-inducible S-phase entry in WI-38 cells.

The potential of the E-Br DNA enzymes to attenuate the ability of E2F1/DP1, in combination with cyclin E/Cdk2, to induce S-phase in quiescent WI-38 cells, was tested. In agreement with published data (Lomazzi, M., et al. *Nat Gen* 31, 190-194 (2002)), expression of E2F1/DP1 or cyclin E/Cdk2 alone did not result in an increase in BrdU incorporation (FIG. 13B). In contrast, co-expression of E2F1/DP1 and cyclin E/Cdk2 drove quiescent cells across the G1/S boundary and induced S-phase.

At a concentration of 0.1 µM, all three DNA enzymes failed to prevent S phase entry induced by co-expression of E2F1/DP1 and cyclin E/Cdk2. These data suggest that TRIP-Br1 and TRIP-Br2 target one or more regulatory steps upstream of cyclin E/Cdk2 in the serum-inducible cell cycle signaling pathway.

E-Br DNA enzymes suppress serum-stimulated CCNE gene induction. We investigated the effects of the E-Br DNA enzymes on the induction of CCNE in WI-38 cells following serum stimulation. CCNE encodes the key G1/S transition regulator, cyclin E (Keyomarsi, K. and Herliczek, T. W. *Prog Cell Cycle Res* 3, 171-191 (1997)). In quiescent WI-38 fibroblasts, the CCNE gene was inactive, as determined by our RT-PCR analysis (FIG. 14A, lane 1). At 16 h after serum stimulation, CCNE transcripts were readily detectable (FIG. 14A, lane 2), confirming that the CCNE gene is induced upon addition of serum to quiescent WI-38 fibroblasts. Serum-induced CCNE gene activation was suppressed in the presence of E-Br1 or E-Br2 (FIG. 14A, lanes 4 & 5), but not E-SCR (FIG. 14A, lane 3), suggesting that both TRIP-Br1 and TRIP-Br2 are required for CCNE induction in response to serum stimulation. Consistent with the RT-PCR data, our western blot analysis showed that knocking down either TRIP-Br1 or TRIP-Br2 effectively prevented the expression of cyclin E protein (FIG. 14B). The suppression of CCNE induction and cyclin E expression was not associated with observable alteration in the expression profile of Cdk4, cyclin D1 and p27$^{KIP}$ (FIG. 14B).

TRIP-Br2$^{-/-}$ primary mouse embryonic fibroblasts (PMEFs) recapitulate E-Br2-mediated knock down phenotypes. We next disrupted the TRIP-Br2 gene in mouse and generated TRIP-Br2$^{-/-}$ PMEFs. TRIP-Br2 knockout was verified both at the level of genomic DNA (by PCR) as well as mRNA (by semi-quantitative RT-PCR) (data not shown). To determine whether TRIP-Br2$^{-/-}$ PMEFs had acquired altered growth characteristics, comparative BrdU incorporation and cell count analyses were performed. Consistent with the E-Br2 knock down data, TRIP-Br$_2^{-/-}$ PMEFs exhibited significantly lower proliferative potentials compared to the wild-type counterparts, as determined by BrdU incorporation (FIG. 15A). When growth quiescent PMEFs were stimulated to re-enter the cell cycle with 10% FBS, TRIP-Br2$^{-/-}$ PMEFs proliferated at a significantly lower rate compared to the wild-type cells (FIG. 15B). In addition, the CCNE gene was found to be markedly down regulated in TRIP-Br2−/− PMEFs (FIG. 15C). Therefore, the TRIP-Br2$^{-/-}$ PMEFs could recapitulate the E-Br2 DNA enzyme-induced knock down phenotypes. These data lend strong support to the notion that TRIP-Br2 plays an important regulatory role in cellular proliferation and further imply that this elusive regulatory role(s) is conserved in mouse and human.

In our study, the TRIP-Br genes were found to be induced in response to serum stimulation (FIG. 11A). Knocking-down TRIP-Br1 and TRIP-Br2 in WI-38 fibroblasts effectively suppressed serum-induced cellular proliferation, suggesting that the TRIP-Br proteins are physiologically involved in the execution of serum-induced cell cycle progression. Our data reveals that both E-Br1 and E-Br2 suppressed serum-inducible CCNE gene induction and cyclin E expression. Given that cyclin E-associated kinase activity is essential for traversing the restriction point and executing S phase entry during cell cycle progression (Keyomarsi, K. and Herliczek, T. W. *Prog Cell Cycle Res* 3, 171-191 (1997)), we suggest that E-Br1 and E-Br2 may disrupt mitogen-driven cell cycle progression by abrogating the cell cycle regulatory activity of cyclin E/Cdk2 in a manner that imposes a proliferative block.

This series of studies involving DNA enzymes has demonstrated the physiological involvement of both TRIP-Br1 and TRIP-Br2 in executing serum-inducible cellular proliferation.

Example 3

Generation of Monoclonal Antibody Against Human TRIP-Br1

Figure 17:
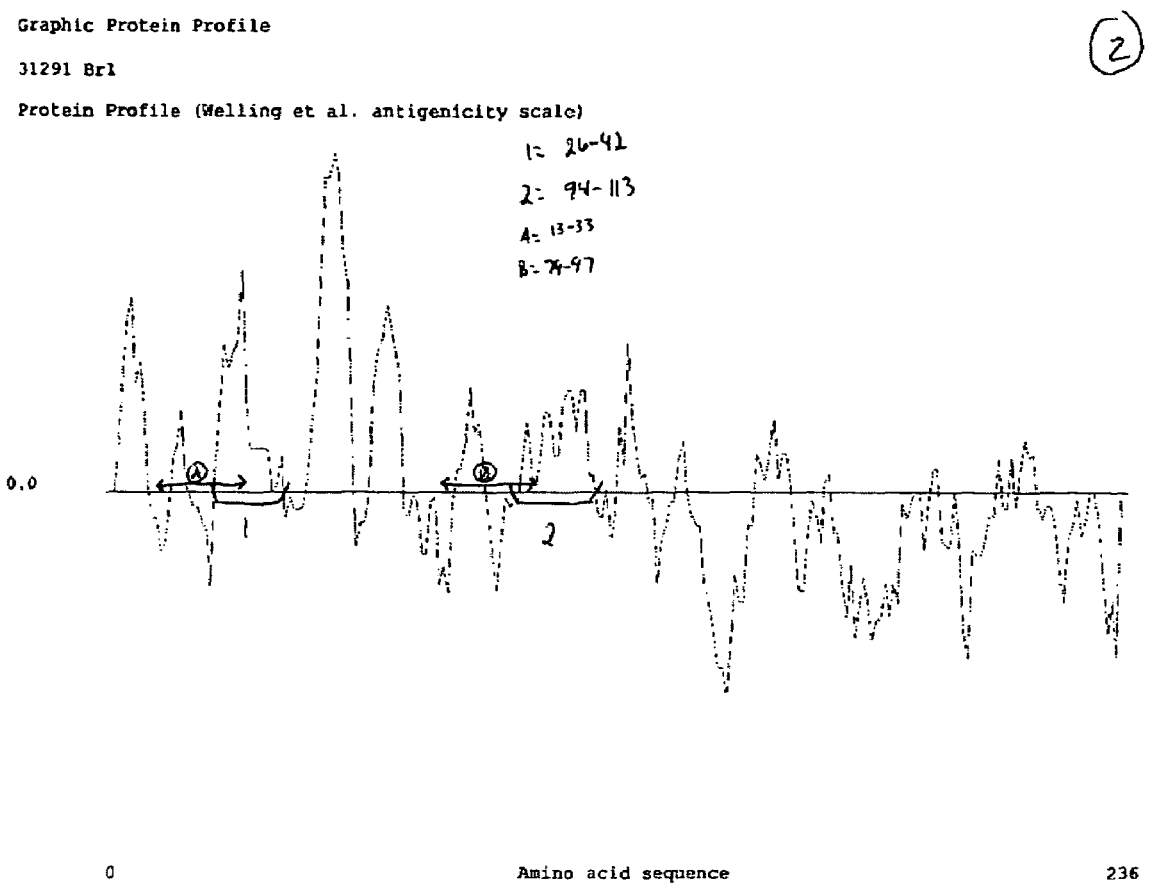
FIG. 17 is a plot of antigenicity versus residue number of human TRIP-Br1.
Figure 18:
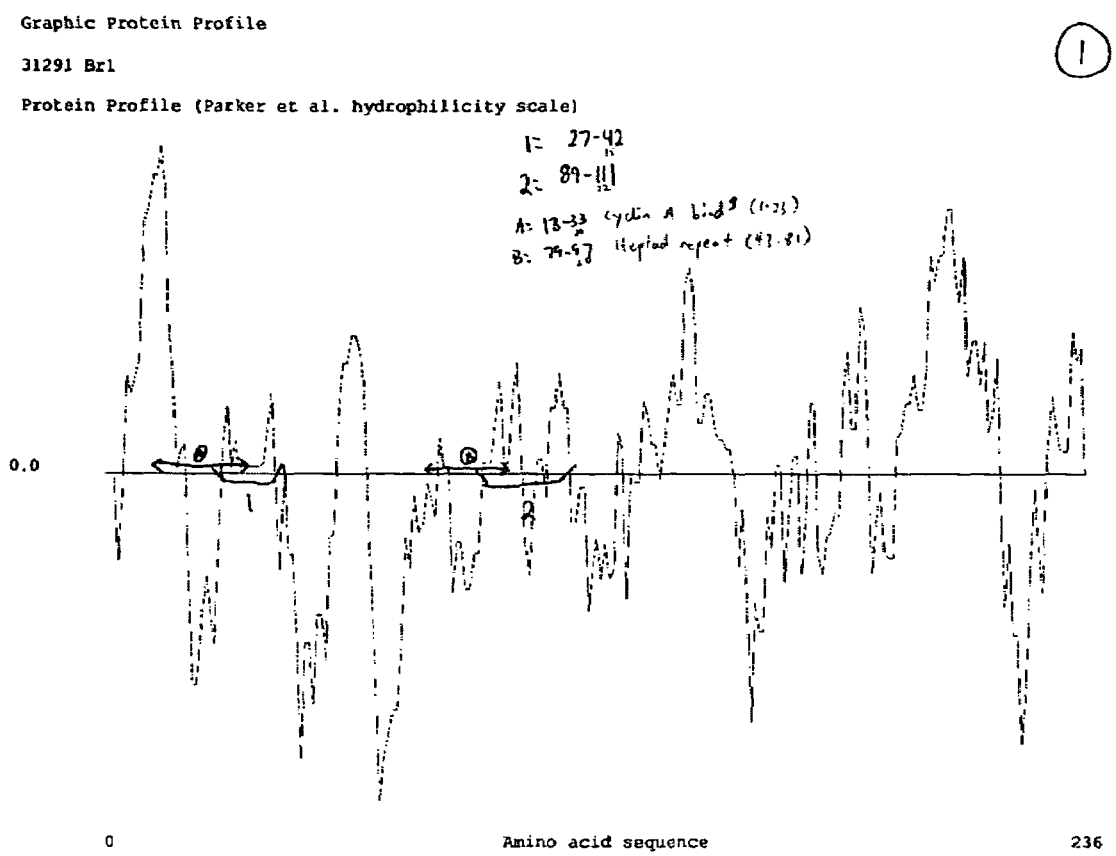
FIG. 18 is a plot of hydrophilicity versus residue number of human TRIP-Br1.
Figure 19:
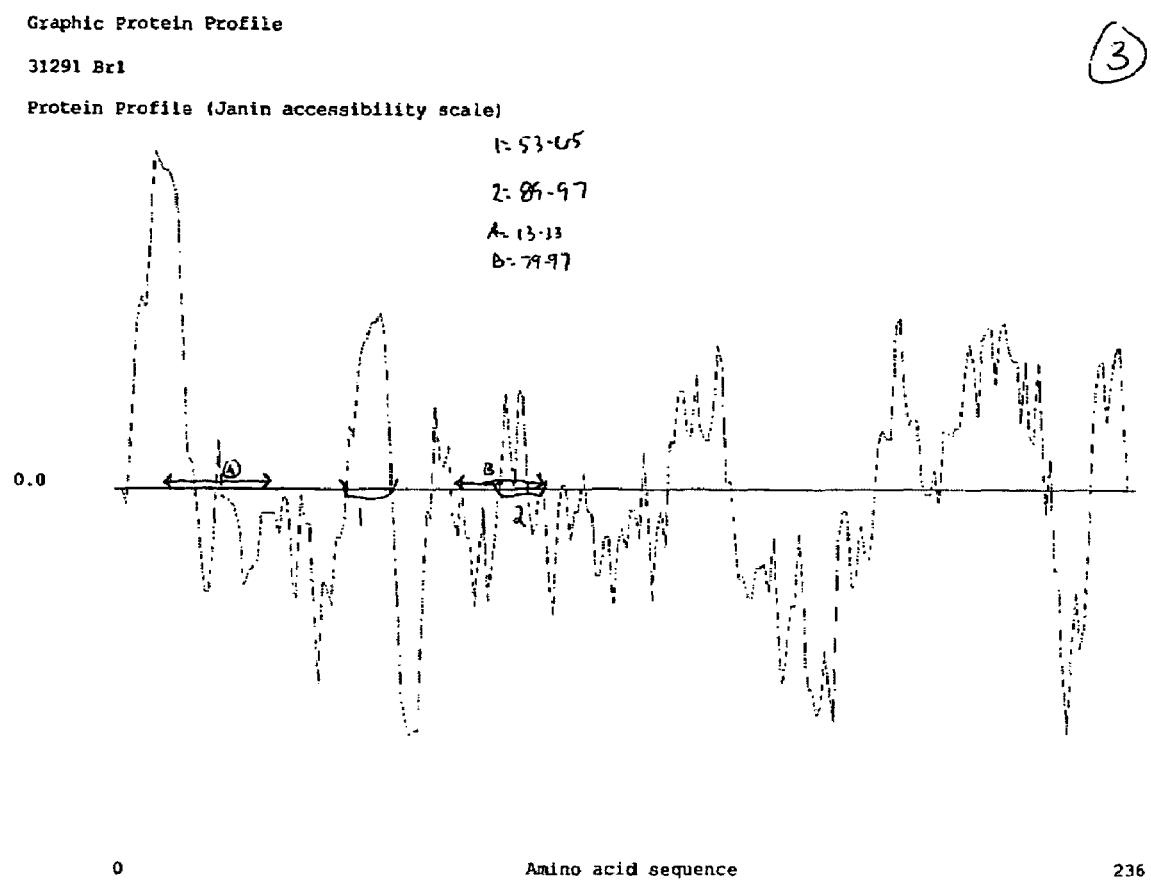
FIG. 19 is a plot of accessibility versus residue number of human TRIP-Br1.

Selection of Peptides. For the selection of possible peptides, we employed the free services of Alpha Diagnostic International, Inc. (ADI) offered on their website, http://www.4adi.com. Peptides 10 to 25 amino acid residues long were selected based on antigenicity, hydrophilicity and accessibility. Identified peptides were subjected to BLAST searches to confirm specificity. In addition, ADI subjects the peptides under analysis to Proteins Secondary Structure Analyses (PSSA) and multiple sequence alignment using ClustalW. The analyses of hTRIP-Br1's antigenicity, hydrophilicity and accessibility are shown in FIGS. 17, 18 and 19 respectively. Sequences which have high values on all 3 graphs were chosen. Two peptides were identified: TB1-27 and TB-98. Their details are as follows. TB1-27: 16 residues from residue 27 to 42. The sequence, starting from N-terminus is DPGHTAAVAQAPPAVAS [SEQ ID NO.: 10]. TB1-98: 15 residues from residue 98 to 112. The sequence, starting from the N-terminus is SVADNLLASSDAALS [SEQ ID NO.: 11].

The BLAST searches showed specificity to the human TRIP-Br1 and incomplete specificity to the murine homologue. No significant protein secondary structure was identified by PSSA. The result of the multiple sequence alignment is presented in FIG. 20, where the human TRIP-Br2, mouse TRIP-Br2, human TRIP-Br1 and mouse TRIP-Br1 full-length sequences shown are respectively SEQ ID NOS.: 12-15. Both peptides are significantly different from human TRIP-Br2, another member of the TRIP-Br family of proteins. However, they are highly homologous to the mouse TRIP-Br1. TB1-27 differs from the corresponding mTRIP-Br1 region by 4 residues, and TB1-98 by 2. This might be the reason for the poor antibody induction in mice.

Figure 21:
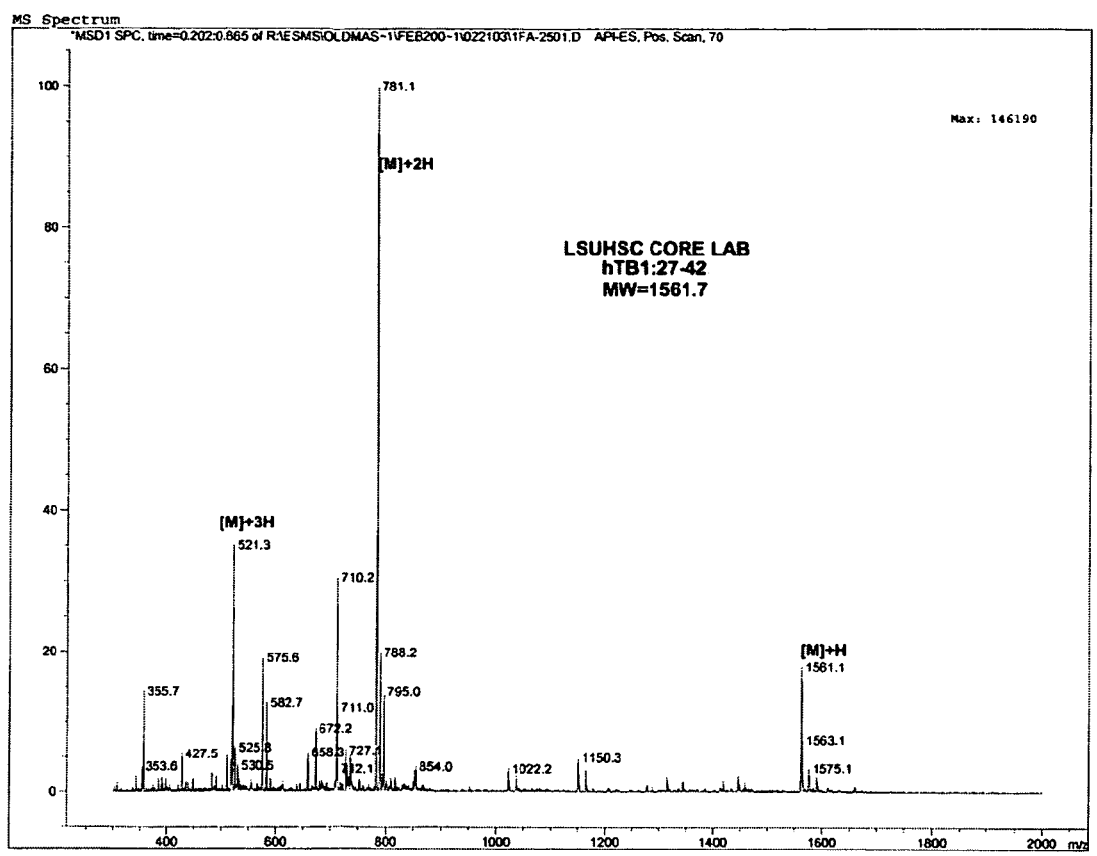
FIG. 21 is a mass spectrophotometry spectrum of the TB1-27 peptide.

Keyhole limpet hemocyanin (KLH)-conjugated TB1-27 and TB1-98 were acquired from Research Biolabs, Singapore. They were supplied at 1 mg/ml in phosphate buffered saline. The mass spectrophotometry spectrum of TB1-27 is shown in FIG. 21.

Immunization. Two BALB/c female mice were immunized for every peptide. Immunogens were prepared according to the protocol in the ImmunEasy™ Mouse Adjuvant Handbook (Qiagen). Ten μg of peptide was administered as a priming dose to each mouse. Subsequently, boosting doses of 5 μg of peptide was given every 2 weeks. In total, 5 shots were administered.

Hybridoma Cloning. The mice were sacrificed 3 days after the last boost. Their spleens were isolated under aseptic conditions and fused with a murine myeloma cell line, X63Ag. The ClonaCell-HY Hybridoma Cloning Kit (Stem-Cell Technologies) was used. The protocol provided was followed strictly. However, the splenocytes of mice immunized with the same peptide was combined for each cloning procedure.

One of the 2 mice injected with TB1-98 died before the final boost. The other looked sickly and splenocytes isolated from this animal did not fuse with X93Ag, hence no hybridoma clones were obtained with TB 1-98.

Analysis of Hybridoma Clones. The 420 hybridoma clones obtained with TB1-27 were analyzed by ELISA. Specificity was tested by overnight incubation of spent media in wells separately coated with TB1-27 and an unrelated KLH-conjugated peptide, Cyr61. 147 clones (35%) tested positive (i.e. bound to TB1-27 coated wells), of which 39 (9.3%) were specific (did not bind to Cyr61 coated wells).

The specificity of the 39 clones was further analyzed by Western blotting. U2OS cells were transfected with pcDNA3 vectors with FLAG-tagged human TRIP-Br1 or TRIP-Br2 inserts, using Polyfect (Qiagen). The cell lysates were separated on a 10% polyacrylamide gel which was then blotted onto Immobilon-P membranes (Millipore). Spent media were diluted 1:1 with blotting buffer and incubated with the blots overnight. Only 6 clones showed some specificity to the FLAG-TRIP-Br1 band (results not shown.). The rest either did not bind to the band or were highly non-specific.

However, upon further expansion of the clones, only the clone numbered 2 (TB1-27#2) survived. This is probably due to the nature of the Hybridoma Kit which allows splenocytes to proliferate for a limited time in the media supplied.

Production of Monoclonal Antibodies. TB1-27#2 was expanded in Medium A from the ClonaCell-HY Hybridoma Cloning Kit. Cells from confluent medium were spun down and transferred to CD Hybridoma Medium supplemented with GlutaMax™ I (Gibco, Invitrogen). The culture was monitored until maximum cell density was reached, before the addition of OptiMAb (Gibco, Invitrogen). The pH of the culture medium was adjusted to the range of pH 6.8 to 7.2 with sodium hydroxide. After 9 days, the cells were removed by centrifugation and the spent medium was harvested.

Characterization of TB1-27#2.: For isotype determination, the ImmunoPure Monoclonal Antibody Isotyping Kit (Pierce) was used. The results showed that TB1-27#2 belongs to the IgG2a subclass with kappa-light chains.

Figure 22:
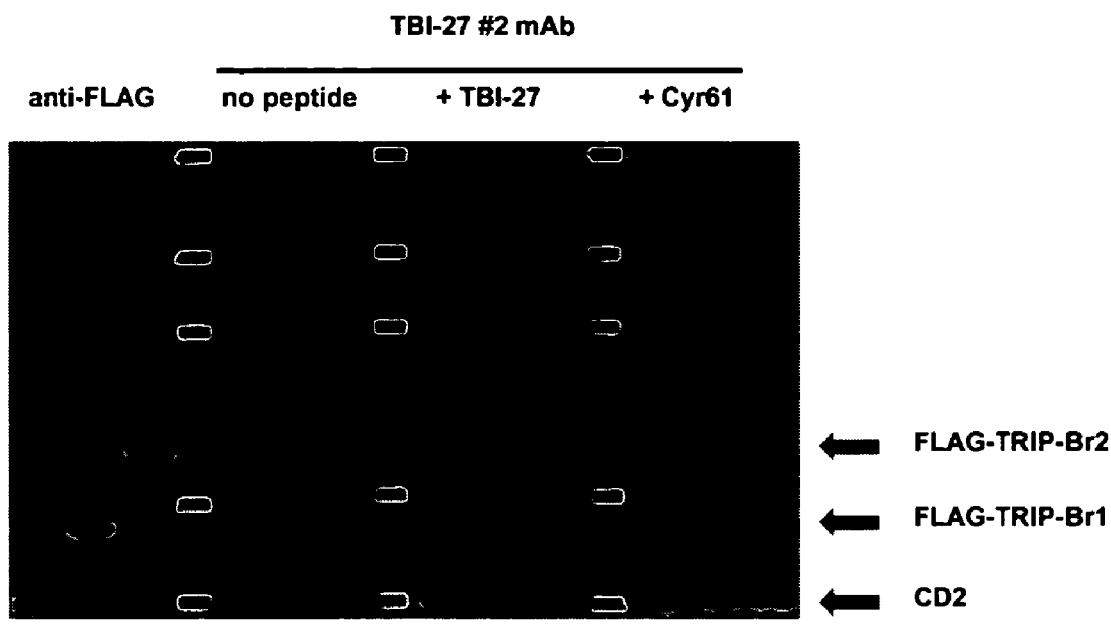
FIG. 22 is a western blot analysis of U2OS cells transfected with pcDNA3/FLAG-TRIP-Br1 or vectors, competed with TB1-27 or Cyr61 peptide.

For Western blot analysis, U2OS cells transfected with the pcDNA3 vector, pcDNA3 vector with TRIP-Br1 insert or TRIP-Br2 insert were harvested. The lysates were separated in a 10% acrylamide gel and blotted onto a transfer membrane. The blot was cut and probed with a mouse monoclonal anti-FLAG antibody or TB1-27#2. For 2 sections, TB1-27 and Cyr61 peptides were added in addition to TB1-27#2 as a source of competition. The results showed that TB1-27 was able to block the binding between the monoclonal antibody, TB1-27#2 whereas the unrelated Cyr61 peptide could not (FIG. 22; for each set, the first lane from left contains the cell lysate of U2OS cells transfected with the pcDNA3 vector; the second, U2OS cells transfected with pcDNA3/FLAG-TRIP-Br1 and the third, U2OS cells transfected with pcDNA3/FLAG-TRIP-Br2; the marker sizes are 210 kD, 125 kD, 101 kD, 56 kD and 36 kD; the CDK2 bands were used as loading control).

Figure 23:
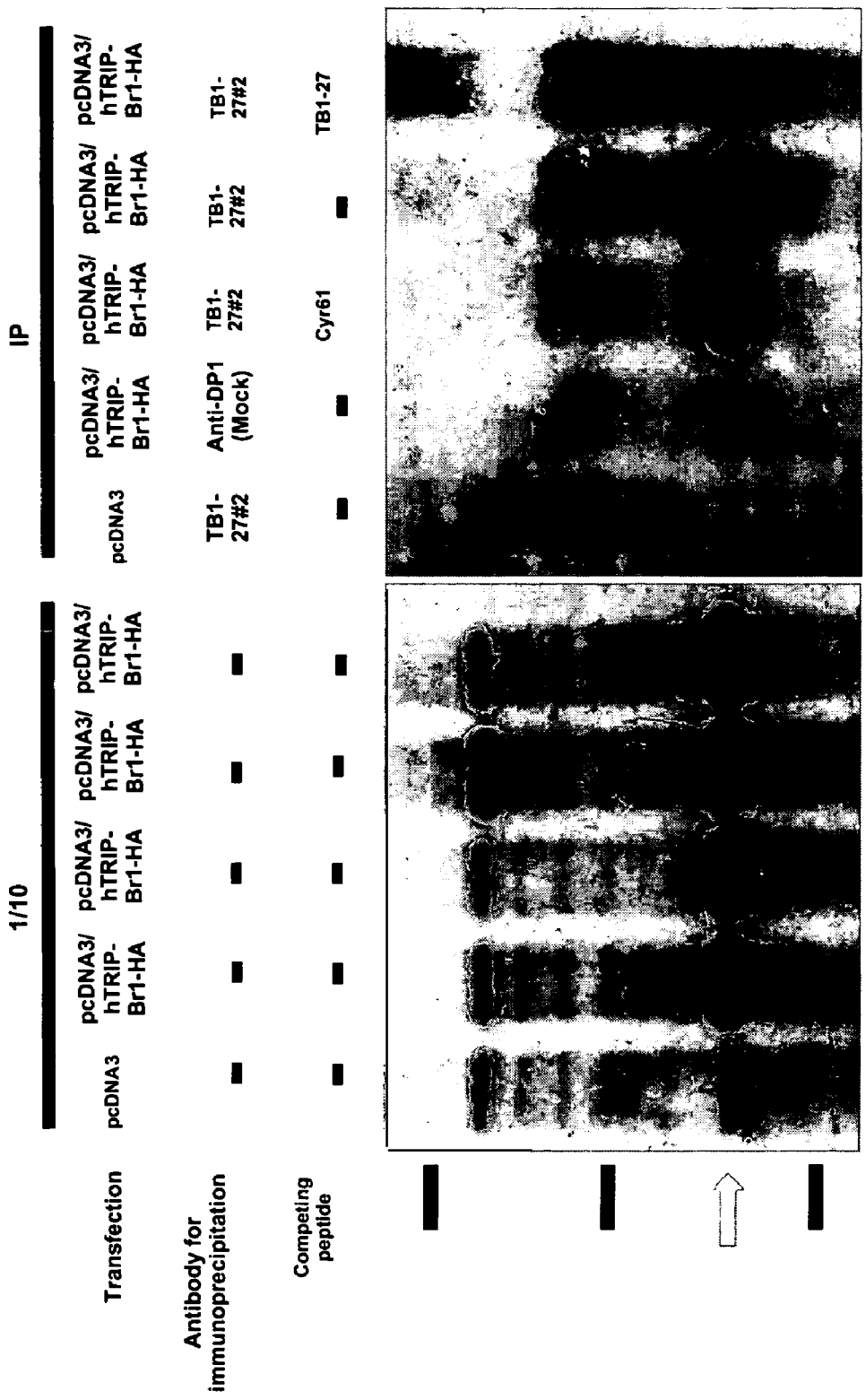
FIG. 23 is western blot analysis of an immunoprecipitation of U2OS cells expressing FLAG-TRIP-Br1, immunoprecipitated with a novel mouse anti-hTRIP-Br1 monoclonal antibody.

In an immunoprecipitation assay, fifty microliters of Protein A-agarose (Amersham) were incubated with 2 ml of TB1-27#2 spent media overnight. Each aliquot of agarose was washed and added to the lysates of variously transfected U2OS cells. The TB1-27 and Cyr61 peptides were separately added into 2 of the reactions while one of the reactions was probed with mouse monoclonal anti-His antibodies instead of TB2-27#2. The agarose was harvested and washed the next day, and the bound proteins analyzed by SDS-PAGE. The gel was blotted and detected with anti-FLAG antibodies. The results are shown in FIG. 23 (the left panel contains $1/10^{th}$ of the input of the pre-cleared U2OS cell lysate while the right panel contains the proteins eluted from the Protein A-agarose). As shown, TB1-27#2 is capable of immunoprecipitating the FLAG-TRIP-Br1 protein. This binding is also specific; the TB1-27 peptide abolished the binding, demonstrated by the lack of the FLAG-TRIP-Br1 band, whereas Cyr61 peptide had no such effect. Anti-DP-1 was used as a positive control for immunoprecipitation since it is known that TRIP-Br1 interacts directly with DP-1.

Example 4

Anti-Tumour Effects of Decoy Peptides in Chick Embryo Chorioallantoic Membrane (CAM) Model Materials and Methods Cell lines. Human nasopharyngeal cancer cell line CNE2 and human melanoma cell line Mewo were used for tumor inoculation.

Chicken embryo CAM preparation. To apply cells onto the CAM of 10-day old chick embryos, a 2-cm diameter wide window was opened in the flat pole of the eggshell with an electric drill equipped with a 0.3-mm thick×22-mm diameter Carborundum disc. The shell window was removed with forceps. The inner shell membrane was carefully punctured with a fine sterile forcep and removed to expose the underlying CAM. A small portion of the CAM was then gently traumatized by laying a strip of lens tissue (1-cm wide) on the surface of the CAM and then removing it immediately.

Inoculation, closure & incubation. The inoculum ($1\times10^6$ cells/egg for CNE2 cell line and $3\times10^6$ cells/egg for Mewo cell line in 50 µl of blank medium) was applied onto the small patch of traumatized CAM. Following inoculation, the window was covered with a 35 mm tissue culture dish and sealed with scotch tape. The embryos were returned to the incubator in an upright position and allowed to incubate for seven additional days, with daily monitoring.

Peptide treatment & assessment of growth inhibitory effects. The treatment was initiated two days after tumor inoculation.

The eggs were randomized into 4 treatment groups, with each group comprising at least 4 biological replicates. Group 1: Vehicle control (200 µl of sterile PBS); Group 2: Mock treatment control (50 µM of *SCR); Group 3: *Br1 (50 µM); Group 4: *Br2 (50 µM).

The various treatments were topically administered onto the tumor xenograft on the CAMs on a daily basis. Five days later, the embryos were terminated by hypothermia and fixed in 10% of formalin. The fixed CAMs were removed and the tumor xenografts were photographed, then dissected from the membrane and weighed. The experiment was repeated once.

Results

Figure 24:
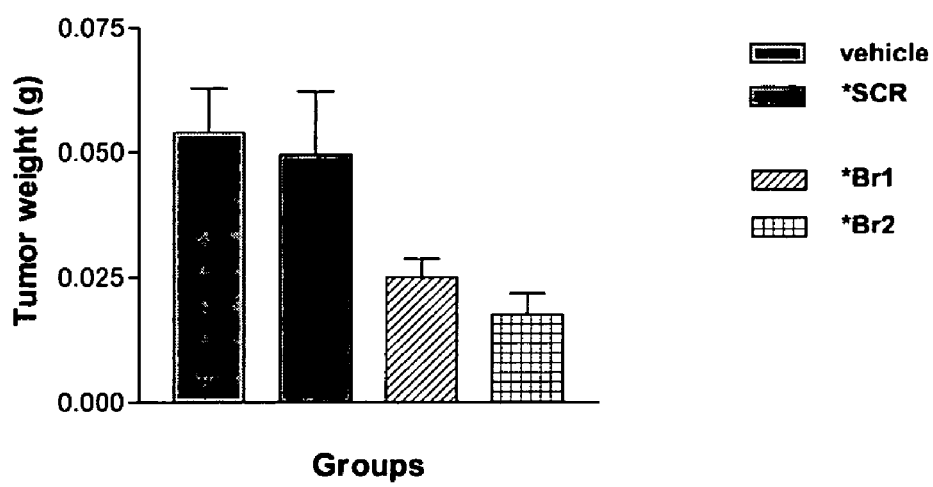
FIG. 24 is a graph showing tumour weight of CNE2 tumours treated with decoy peptides.

Topically administered *Br1 or *Br2, but not *SCR, significantly inhibited the growth of CNE2 tumor over a period of seven days ($p<0.05$, ANOVA, LSD, SPSS 12) (FIG. 24).

As can be understood by one skilled in the art, many modifications to the exemplary embodiments described herein are possible. The invention, rather, is intended to encompass all such modification within its scope, as defined by the claims.

What is claimed is:

1. A peptide modulator capable of modulating activity of TRIP-Br, the peptide modulator comprising a sequence having the formula UTGXLXDXXLZJOLFJDID, wherein variable X is any amino acid; variable U is Ser, Thr, Ala or no amino acid; variable Z is Asp or Glu; variable J is Asp or Glu, Ala or Gly; and variable O is Ile, Leu, Val, Ala or no amino acid.

2. The peptide modulator of claim 1, wherein the peptide modulator further comprises the amino acid sequence set forth as SEQ ID NO: 3.

3. The peptide modulator of claim 1 wherein the peptide modulator consists of the amino acid sequence of SEQ ID NO: 4 or SEQ ID NO: 5.

4. A pharmaceutical composition comprising the peptide modulator of claim 1.

5. The pharmaceutical composition of claim 4 wherein the peptide modulator further comprises the amino acid sequence set forth as SEQ ID NO: 3.

6. The pharmaceutical composition of claim 4 wherein the peptide modulator comprises the amino acid sequence of SEQ ID NO.: 4 or SEQ ID NO.: 5.

7. The peptide modulator of claim 1 wherein the peptide modulator comprises the amino acid sequence of SEQ ID NO:4 or SEQ ID NO:5.

8. The peptide modulator of claim 1 wherein the peptide modulator consists of a sequence having the formula UTGXLXDXXLZJOLFJDID, wherein variable X is any amino acid; variable U is Ser, Thr, Ala or no amino acid; variable Z is Asp or Glu; variable J is Asp or Glu, Ala or Gly; and variable O is Ile, Leu, Val, Ala or no amino acid.

9. The pharmaceutical composition of claim 4 wherein the peptide modulator consists of a sequence having the formula UTGXLXDXXLZJOLFJDID, wherein variable X is any amino acid; variable U is Ser, Thr, Ala or no amino acid; variable Z is Asp or Glu; variable J is Asp or Glu, Ala or Gly; and variable O is Ile, Leu, Val, Ala or no amino acid.

10. The peptide modulator of claim 8 consisting of a sequence having the amino acid sequence of SEQ ID NO: 1 or SEQ ID NO: 2.

11. The pharmaceutical composition of claim 9 wherein the peptide modulator consists of the amino acid sequence of SEQ ID NO: 1 or SEQ ID NO: 2.

* * * * *